United States Patent
Zegzouti et al.

(10) Patent No.: US 8,802,411 B2
(45) Date of Patent: *Aug. 12, 2014

(54) ADP DETECTION BASED LUMINESCENT PHOSPHOTRANSFERASE OR ATP HYDROLASE ASSAY

(75) Inventors: Hicham Zegzouti, Madison, WI (US); Said A. Goueli, Fitchburg, WI (US)

(73) Assignee: Promega Corporation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/455,587

(22) Filed: Apr. 25, 2012

(65) Prior Publication Data

US 2012/0258480 A1    Oct. 11, 2012

Related U.S. Application Data

(62) Division of application No. 12/460,573, filed on Jul. 20, 2009, now Pat. No. 8,183,007.

(60) Provisional application No. 61/182,372, filed on May 29, 2009, provisional application No. 61/170,308, filed on Apr. 17, 2009, provisional application No. 61/082,775, filed on Jul. 22, 2008.

(51) Int. Cl.
    *C12N 9/00* (2006.01)
    *C12Q 1/48* (2006.01)

(52) U.S. Cl.
    USPC ............................................. 435/183; 435/15

(58) Field of Classification Search
    USPC ........................................... 435/183, 18, 15
    See application file for complete search history.

(56) References Cited

U.S. PATENT DOCUMENTS

| | | | |
|---|---|---|---|
| 4,923,796 A | 5/1990 | Deneke et al. | |
| 5,316,907 A | 5/1994 | Lurie et al. | |
| 5,618,665 A * | 4/1997 | Lurie et al. | 435/4 |
| 5,837,465 A | 11/1998 | Squirrell et al. | |
| 6,132,983 A | 10/2000 | Lowe et al. | |
| 6,171,808 B1 | 1/2001 | Squirrell et al. | |
| 6,265,177 B1 | 7/2001 | Squirrell et al. | |
| 6,265,179 B1 * | 7/2001 | Zhou et al. | 435/28 |

(Continued)

FOREIGN PATENT DOCUMENTS

| | | |
|---|---|---|
| CN | 1164259 | 11/1997 |
| CN | 1395619 | 2/2003 |

(Continued)

OTHER PUBLICATIONS

Adenylate Cyclase. Wikipedia. Nov. 2007 [retrieved on Apr. 23, 2013]. Retrieved from the Internet: <URL:http://web.archive.org/web/20071117020856/http://en.wikipedia.org/wiki/Adenylate_cyclase>.*

(Continued)

*Primary Examiner* — Jon P Weber
*Assistant Examiner* — Kara Johnson
(74) *Attorney, Agent, or Firm* — Michael Best & Friedrich LLP

(57) ABSTRACT

The invention provides compositions and methods to determine or detect the activity of enzymes, including phosphotransferases such as kinases (e.g., protein, lipid, and sugar kinases) and ATP hydrolases such as ATPases, e.g., HSP90, that employ ATP as a substrate and form ADP as a product by monitoring changes in ADP. Methods, kits and compositions for monitoring changes in metabolites such as ADP are disclosed.

11 Claims, 40 Drawing Sheets

(56) References Cited

U.S. PATENT DOCUMENTS

| | | | |
|---|---|---|---|
| 6,599,711 | B2 | 7/2003 | Crouch et al. |
| 6,602,677 | B1 | 8/2003 | Wood et al. |
| 6,762,026 | B1* | 7/2004 | Sugiyama ............... 435/6.14 |
| 6,911,319 | B2 | 6/2005 | Crouch et al. |
| 7,247,435 | B2 | 7/2007 | Sugiyama |
| 7,332,278 | B2 | 2/2008 | Lowery et al. |
| 7,338,775 | B1 | 3/2008 | Ostanin et al. |
| 8,183,007 | B2 | 5/2012 | Zegzouti et al. |
| 2004/0101922 | A1 | 5/2004 | Somberg et al. |
| 2004/0253685 | A1 | 12/2004 | Sessa |
| 2005/0208608 | A1 | 9/2005 | Raven et al. |
| 2006/0199238 | A1 | 9/2006 | Charter et al. |
| 2007/0015790 | A1 | 1/2007 | Cali et al. |
| 2008/0050762 | A1* | 2/2008 | Corey et al. ............... 435/15 |
| 2009/0075309 | A1 | 3/2009 | Gambhir et al. |
| 2009/0093519 | A1* | 4/2009 | Schein et al. ............ 514/311 |
| 2013/0109037 | A1 | 5/2013 | Goueli et al. |

FOREIGN PATENT DOCUMENTS

| | | |
|---|---|---|
| WO | WO 99/14336 | 3/1999 |
| WO | WO 00/24878 | 5/2000 |
| WO | WO 01/20002 | 3/2001 |
| WO | WO 01/31028 | 5/2001 |
| WO | WO WO 03/040100 | 5/2003 |
| WO | WO 2004/027378 | 4/2004 |
| WO | WO 2004/027421 | 4/2004 |
| WO | 2013/063563 | 5/2013 |

OTHER PUBLICATIONS

Branchini, B.R. et al., "Yellow-green and red firefly bioluminescence from 5,5-dimethyloxyluciferin," J. Am. Chem. Soc. (2002) 124:2112-2113.

Branchini, B.R. et al., "Chemical synthesis of firefly luciferase analogs and inhibitors," Meth. Enzymol. (2000) 305:188-195.

Branchini, B.R. et al., "Naphthyl- and quinolylluciferin: green and red light emitting firefly luciferin analogues," Phohtochem. Photobiol. (1989) 49(5):689-695.

Gietzen, K. et al, "Inhibition of human erythrocyte Ca++-transport ATPase by phenothiazines and butyrophenones," Biochem. Biophys. Res. Commun. (1980) 94:674-681.

Gietzen, K. et al., "R 24571: a new powerful inhibitor of red blood cell Ca++-transport ATPase and of calmodulin-regulated functions," Biochem. Biophys. Res. Commun. (1981) 101:418-425.

Gietzen, K. et al., "A model for the regulation of the calmodulin-dependent enzymes erythrocyte Ca2+=transport ATPase and brain phosphodiesterase by activators and inhibitors," Biochem. J. (1982a) 207:541-548.

Gietzen, K. et al., "Effects of vinblastine and colchicine on calmodulin-dependent Ca2+-transport ATPase of human erythrocytes," IRCS Med. Sci. (1980) 8:396-397.

Gietzen, K. et al., "Compound 48/80: a powerful and specific inhibitor of calmodulin-dependent Ca2+-transport ATPase," IRCS Med. Sci. (1983) 11:12-13.

Gietzen, K. et al., "Effects of microtubular inhibitors on plasma membrane calcodulin-dependent Ca2+-transport ATPase," Mol. Pharmacol. (1982b) 22:413-420.

Gietzen, K., "Comparison of the calmodulin antagonists compound 48/80 and calmidazolium," Biochem. J. (1983) 216(3):611-616.

Glaser, P. et al., "The calmodulin-sensitive adenylate cyclase of *Bordetella pertussis:* cloning and expression in *Escherichia coli*," Mol. Microbiol. (1988) 2(1):19-30.

Hong, J. et al., "Anthrax edema factor potency depends on mode of cell entry," Biochem. Biophys. Res. Commun. (2005) 335(3):850-857.

Kobayashi, R. et al., "Ca2+-regulated modulator protein interacting agents: inhiitors of Ca2+=Mg2+-ATPase of human erythrocyte ghost," Biochem. Biophys. Res. Commun. (1979) 88:1037-1045.

Ladant, D. et al., "Characterization of the calmodulin-binding and of the catalytic domains of *Bordetella pertussis* adenylate cyclase," J. Biol. Chem. (1989) 264(7):4015-4020.

Lee, R.T. et al., "Substrate-binding properties of firefly luciferase. II. ATP-binding site," Arch. Biochem. Biophys. (1970) 141:38-45.

Levin, R. et al., "Mechanism by which psychotropic drugs inhibits adenosine cyclic 3'-5'-monophosphate phosphodiesterase of brain,"Mol. Pharmacol. (1976) 12:581-589.

Sala-Newby, G. et al., "Engineering firefly luciferase as an indicator of cyclic AMP-dependent protein kinase in living cells," FEBS Lett. (1992) 30:241-244.

Schmutz, D. et al., "Rapid-simple measurement of ATP-sulfurylase activity in crude plant extracts using an ATP meter for bioluminescence determination," Anal. Biochem. (1982) 121:151-155.

Schultz, V. et al., "Bioluminometric assay of ADP and ATP at high ATP/ADP ratios: assay of ADP after enzymatic removal of ATP," Anal. Biochem. (1993) 215(2):302-304.

Steghens, J-P. et al., "Firefly luciferase has two nucleotide binding sites: effect of nucleoside monophosphate and CoA on the light-emission spectra," Biochem. J. (1998) 336:109-113.

Volpi, M. et al., "Antagonism of calmodulin by local anesthetics. Inhibition of calmodulin-stimulated calcium transport of erythrocyte inside-out membrane vesicles," Mol. Pharmacol. (1981) 20:363-370.

Watanabe, K. et al. "Specific inhibitor of a calcium dependent activation of brain cyclic AMP phosphodiesterase activity by vinblastine,"Experientia (1979) 35:1487-1489.

Weiss, B. et al., "Pharmacological regulation of calmodulin,"Ann. N.Y. Acad. Sci. (1980) 356:319-345.

Wolff, D.J. et al., "Calcium-dependent cyclic nucleotide phosphodiesterase from brain: identification of phospholipids as calcium-independent activators," Arch. Biochem. Biophys. (1976) 173:720-731.

Yu, M. et al., "Rat liver ATP-sulfurylase: purification, kinetic characteristics, and interaction with arsenate, selenate, phosphate, and other inorganic oxyanions," Anal. Biochem. (1989) 269:156-174.

International Search Report and Written Opinion for Application No. PCT/US2009/051170 dated Oct. 28, 2009 (9 pages).

United States Patent Office Action for U.S. Appl. No. 12/460,573 dated Oct. 13, 2011 (7 pages).

United States Patent Office Notice of Allowance for U.S. Appl. No. 12/460,573 dated Feb. 9, 2012 (5 pages).

European Patent Application No. 09790643.2 dated Sep. 11, 2012 (4 pages).

"Technical Manual"; "TM#384" In: AMP-Glo TM Assay Instructions for Use of Products V5011, V5012 and V5013, Oct. 1, 2012, Promega, USA.

Berndsen et al., "A spectrophotometric assay for conjugation of ubiquitin and ubiquitin-like proteins," (2011) Anal. Biochem. 318: 102-110.

Boisclair et al., "Development of a Ubiquitin Transfer Assay for High Throughput Screening by Fluorescence Resonance Energy Transfer," (2000) J. Biomolec. Screen. 5: 319-328.

Brotz-Oesterhelt, et al., "Specific and Potent Inhibition of NAD+ -dependent DNA Ligase by Pyridochromanones," (2003) J. Biol. Chem. 278: 39435-39442.

Carlson et al., "A Toolbox Approach to High-Throughput TR-FRET-Based SUMOylation and DeSUMOylation Assays," (2009) Assay and Drug Dev. Technol., 7: 348-355.

Chen, JJ et al., "Mechanistic Studies of Substrate-assisted Inhibition of Ubiquitin-activating Enzyme by Adenosine Sulfa mate Analogues," (2011) J. Biol. Chem., pp. 40867-40877.

Golinska, M et al., "Adaptation to HIF-1 deficiency by upregulation of the AMP/ATP ratio and phosphofructokinase activation in hepatomas," 2011, BMC Cancer 11: 198, pp. 1-13.

Goueli, S. et al., "Abstract 164: High Throughput Homogenous Bioluminescent Assays For Monitoring The Concentrations of AMP ADP and ATP," America Association for Cancer Research, Annual Meeting, Mar. 31-Apr. 4, 2012, Chicago, Presented at the poster section 6, board 18, on Apr. 1, 2012, Retrieved from Internet <URL:http://www.promega.de/~/media/Files/Resources/Posters/High%20Throughput%20Homogeneous%20Bioluminescent%20Assays%20for%20Monitoring%20AMP%20ADP%20and%20ATP%20Poster.pdf>.

Gururaja et al, "A Homogeneous FRET Assay System for Multiubiquitin Chain Assembly and Disassembly," (2005) Meth. Enzymol. 399: 663-682.

(56) References Cited

OTHER PUBLICATIONS

Haas, et al., "The Mechanism of Ubiquitin Activating Enzyme, A Kinetic and Equilibrium Analysis," (1982) J. Biol. Chem. 257: 10329-10337.

Hendricks et al., "An enzyme-coupled colorimetric assay for S-adenosylmethionine-dependent methyltransferases," (2004) Anal. Biochem. 326: 100-105.

Kim et al., "Aminoacyl-tRNA synthetases and tumorigenesis: more than housekeeping," (2011) Nature Rev Cancer, 11: 708-718.

Kim et al., "Analysis of in vitro SUMOylation using bioluminescence resonance energy transfer (BRET)," (2009) Biochem. Biophys. Res. Commun.382: 530-534.

Komander, D, "The emerging complexity of protein ubiquitination," 2009, Biochem. Soc.Trans. 37: 937-953.

Lust, W. et al., "The enzymatic measurement of adenine nucleotides and P-creatine in picomole amounts," Analytical Biochemistry, vol. 110, No. 1, Jan. 1, 1981, pp. 258-266.

Marblestone, "Novel Approach for Characterizing Ubiquitin E3 Ligase Function," (2010) J. Biomol. Screening, 15: 1220-1228.

Perrett, D, "Comparative Performance of Ion Exchange and Ion-paired Reversed Phase High Performance Liquid Chromatography for the Determination of Nucleotides in Biological Samples," (1991) Biomed Chromatography 5: 207-211.

Resnick, S. et al., "In Vitro ATP Regeneration from Polyphosphate And AMP By Polyphosphate: AMP Phosphatransferase And Adenylate Kinase from Acinetobacter Johnsonll 210A," Applied And Environmental Microbiology, vol. 66, No. 5, May 1, 2000, pp. 2045-2051.

Ronner, P. et al., "Luminometric Assays of ATP, Phosphocreatine, and Creatine for Estimation of Free ADP and Free AMP," Analytical Biochemistry,vol. 275, No. 2, Nov. 15, 1999, pp. 208-216.

Rose et al., "A specific endpoint assay for ubiquitin (ubiquitin-activating enzyme)," (1987) Proc. Natl. Acad. Sci. USA 84: 1477-1481.

Shapiro et al., "High-Throughput Fluorescence Resonance Energy Transfer-Based Assay for DNA Ligase," 2011, 16: 486-493.

Tanaka, S. et al., "A sensitive method for detecting AMP by utilizingpolyphosphate-dependent ATP regeneration and bioluminescence reactions," Biomedical Engineering Journal, vol. 9 , No. 3, Dec. 1, 2001, pp. 193-197.

Taylor MR et al., "Kinetic Mechanism of Human DNA Ligase I Reveals Magnesium-dependent Changes in the Rate-limiting Step That Compromise Ligation Efficiency," (2011) J. Biol. Chem. 286: 23054-23062.

Tofaris, GK et al., "Ubiquitin ligase Nedd4 promotes α-synuclein degradation by the endosomal-lysosomal pathway," (2011) PNAS, 108: 17004-9.

Wang, R et al., "Formulating a fluorogenic assay to evaluate S-adenosyl-L-methionine analogues as protein methyltransferase cofactors," Mol. BioSyst., 2011, 7, 2970-2981.

Wee, "Steady-State Kinetic Analysis of Human Ubiquitin-Activating Enzyme (EI) Using a Fluorescently Labeled Ubiquitin Substrate," (2000) J Protein Chem., 19: 489-498.

Weiss, B. et al., "Rapid microassay of adenosine 3',5'-monophosphatephosphodiesterase activity," Analytical Biochemistry, vol. 45, No. 1, Jan. 1, 1972, pp. 222-235.

Weissman et al., "The predator becomes the prey: regulating the ubiquitin system by ubiquitylation and degradation," 2011, Nature Rev Mol Cell Biology 12:605-620.

Wilkie and Plater, "Novel Assays Harness the Drug Discovery Potential of Complex Ubiquitination Pathways," (2011) Millipore Corp., 8 pages.

Chinese Patent Office Action for Application No. 200980138112.0 dated Sep. 18, 2013 (Original and English Translation, 11 pages).

International Search Report and Written Opinion for Application No. PCT/US2012/062397 dated Jun. 5, 2013.

Chinese Patent Office Action for Application No. 200980138112.0 dated Mar. 5, 2013 (Original and English Translation, 20 pages).

\* cited by examiner

MQQSHQAGYANAADRESGIPAAVLDGIKAVAKEKNATLMFRLVN
PHSTSLIAEGVATKGLGVHAKSSDWGLQAGYIPVNPNLSKLFGRAPEVIARADNDVNS
SLAHGHTAVDLTLSKERLDYLRQAGLVTGMADGVVASNHAGYEQFEFRVKETSDGRYA
VQYRRKGGDDFEAVKVIGNAAGIPLTADIDMFAIMPHLSNFRDSARSSVTSGDSVTDY
LARTRRAASEATGGLDRERIDLLWKIARAGARSAVGTEARRQFRYDGDMNIGVITDFE
LEVRNALNRRAHAVGAQDVVQHGTEQNNPFPEADEKIFVVSATGESQMLTRGQLKEYI
GQQRGEGYVFYENRAYGVAGKSLFDDGLGAAPGVPSGRSKFSPDVLETVPASPGLRRP
SLGAVERQDSGYDSLDGVGSRSFSLGEVSDMAAVEAAELEMTRQVLHAGARQDDAEPG
VSGASAHWGQRALQGAQAVAAAQRLVHAIALMTQFGRAGSTNTPQEAASLSAAVFGLG
EASSAVAETVSGFFRGSSRWAGGFGVAGGAMALGGGIAAAVGAGMSLTDDAPAGQKAA
AGAEIALQLTGGTVELASSIALALAAARGVTSGLQVAGASAGAAAGALAAALSPMEIY
GLVQQSHYADQLDKLAQESSAYGYEGDALLAQLYRDKTAAEGAVAGVSAVLSTVGAAV
SIAAAASVVGAPVAVVTSLLTGALNGILRGVQQPIIEKLANDYARKIDELGGPQAYFE
KNLQARHEQLANSDGLRKMLADLQAGWNASSVIGVQTTEISKSALELAAITGNADNLK
SVDVFVDRFVQGERVAGQPVVLDVAAGGIDIASRKGERPALTFITPLAAPGEEQRRRT
KTGKSEFTTFVEIVGKQDRWRIRDGAADTTIDLAKVVSQLVDANGVLKHSIKLDVIGG
DGDDVVLANASRIHYDGGAGTNTVSYAALGRQDSITVSADGERFNVRKQLNNANVYRE
GVATQTTAYGKRTENVQYRHVELARVGQVVEVDTLEHVQHIIGGAGNDSITGNAHDNF
LAGGSGDDRLDGGAGNDTLVGGEGQNTVIGGAGDDVFLQDLGVWSNQLDGGAGVDTVK
YNVHQPSEERLERMGDTGIHADLQKGTVEKWPALNLFSVDHVKNIENLHGSRLNDRIA
GDDQDNELWGHDGNDTIRGRGGDDILRGGLGLDTLYGEDGNDIFLQDDETVSDDIDGG
AGLDTVDYSAMIHPGRIVAPHEYGFGIEADLSREWVRKASALGVDYYDNVRNVENVIG
TSMKDVLIGDAQANTLMGQGGDDTVRGGDGDDLLFGGDGNDMLYGDAGNDTLYGGLGD
DTLEGGAGNDWFGQTQAREHDVLRGGDGVDTVDYSQTGAHAGIAAGRIGLGILADLGA
GRVDKLGEAGSSAYDTVSGIENVVGTELADRITGDAQANVLRGAGGADVLAGGEGDDV
LLGGDGDDQLSGDAGRDRLYGEAGDDWFFQDAANAGNLLDGGDGRDTVDFSGPGRGLD
AGAKGVFLSLGKGFASLMDEPETSNVLRNIENAVGSARDDVLIGDAGANVLNGLAGND
VLSGGAGDDVLLGDEGSDLLSGDAGNDDLFGGQGDDTYLFGVGYGHDTIYESGGGHDT
IRINAGADQLWFARQGNDLEIRILGTDDALTVHDWYRDADHRVEIIHAANQAVDQAGI
EKLVEAMAQYPDPGAAAAAPPAARVPDTLMQSLAVNWR (SEQ ID NO:1)

```
encoded by
   1 tgcgatcatt cggcatgtac ggtccagctg cgcgcgagcg gcggccgcgt ccagcgcgcg
  61 gcctcggtac tccttgacgc gcgcggtgtc gccgccgcgc cgaacgcgca gcaacggcc
 121 cacgctgtcg gggtgccgtt cggccagcgc gcggcgcagc gcacgattgt cgtcgcgcga
 181 gaatggcgcg atccagtcga tgatccacag tcggtcgccg cagttccagg cattcccgcc
 241 cagcgacgag ggcgccatga cataggagag ttcggtgtcg gcgtccatta gggcccagct
 301 gcagtatgca accggcacgt cattgcatcg cagcagaatg tattggccca gttgaatcgg
 361 cgcgagcgct gttgcgtgcg agcagatgca ccggccagtc gcggtgcatg ggagagttca
 421 tccacagcca ggcaatattg cccagtgccg cgaagtcgtc ggtgggattg aggagggagg
 481 gcgcttgggc ggacggaagc atgacatcgg tgcatggtgg agcgggggc atattccgtg
 541 ttgggtgcgc gcatggcaag ccgccggcgc atcatggttg cgccggaatg gcttttctta
 601 catgtttcca ggatatgtcc gtatttcggg cgatgcctcg gtcgcggcgc ctgcttttgt
 661 cgaacatgtg caatgttgtt gtcgcgatcg cgttggcgct tgctcgctta tttatctccc
 721 ttgaagcctt gttcttcttt tcattagaaa gaaatatgcg ctttgtgttt aggatgattt
 781 tcctgtccga gtagggtgga tccaaatttt ccggattggt gggaatttgt gcattttcac
 841 tgcgaatgtt ggaataattt cgcccatcgt catacgacat gctggatgtt tggttcttgc
 901 agaaggatga ggttctgagc gctacacacc ggttgcgtcg gtcgaatcc gttcaatcga
 961 ctacttatcg acagatccac atgcagcaat cgcatcaggc tggttacgca aacgccgccg
1021 accgggagtc tggcatcccc gcagccgtac tcgatggcat caaggccgtg gcgaaggaaa
1081 aaaacgccac attgatgttc cgcctggtca accccattc caccagcctg attgccgaag
1141 gggtggccac caaaggattg ggcgtgcacg ccaagtcgtc cgattggggg ttgcaggcgg
1201 gctacattcc cgtcaacccg aatctttcca aactgttcgg ccgtgcgccc gaggtgatcg
1261 cgcgggccga caacgacgtc aacagcagcc tggcgcatgg ccataccgcg gtcgacctga
1321 cgctgtcgaa agagcggctt gactatctgc ggcaagcggg cctggtcacc ggcatggccg
```

Fig. 33A

```
1381 atggcgtggt cgcgagcaac cacgcaggct acgagcagtt cgagtttcgc gtgaaggaaa
1441 cctcggacgg gcgctatgcc gtgcagtatc gccgcaaggg cggcgacgat ttcgaggcgg
1501 tcaaggtgat cggcaatgcc gccggtattc cactgacggc ggatatcgac atgttcgcca
1561 ttatgccgca tctgtccaac ttccgcgact cggcgcgcag ttcggtgacc agcggcgatt
1621 cggtgaccga ttacctggcg cgcacgcggc gggccgccag cgaggccacg ggcggcctgg
1681 atcgcgaacg catcgacttg ttgtggaaaa tcgctcgcgc cggcgcccgt tccgcagtgg
1741 gcaccgaggc gcgtcgccag ttccgctacg acggcgacat gaatatcggc gtgatcaccg
1801 atttcgagct ggaagtgcgc aatgcgctga acaggcgggc gcacgccgtc ggcgcgcagg
1861 acgtggtcca gcatggcact gagcagaaca atcctttccc ggaggcagat gagaagattt
1921 tcgtcgtatc ggccaccggt gaaagccaga tgctcacgcg cgggcaactg aaggaataca
1981 ttggccagca gcgcggcgag ggctatgtct tctacgagaa ccgtgcatac ggcgtggcgg
2041 ggaaaagcct gttcgacgat gggctgggag ccgcgcccgg cgtgccgagc ggacgttcga
2101 agttctcgcc ggatgtactg gaaacggtgc cggcgtcacc cggattgcgg cggccgtcgc
2161 tgggcgcagt ggaacgccag gattccggct atgacagcct tgatggggtg ggatcgcgat
2221 cgttctcgtt gggcgaggtg tccgacatgg ccgccgtgga agcggcggaa ctggaaatga
2281 cccggcaagt cttgcacgcc ggggcgcggc aggacgatgc cgagccgggc gtgagcggtg
2341 cgtcggcgca ctgggggcag cgggcgctgc agggcgccca ggcggtggcg gcggcgcagc
2401 ggctggttca tgccattgcc ctgatgacgc aattcggccg ggccggttcc accaacacgc
2461 cgcaggaagc ggcctcgttg tcgcggccg tgttcggctt gggcgaggcc agcagcgccg
2521 tggccgaaac cgtgagcggt ttttccgcg ggtcttcgcg ctgggccggc ggtttcggcg
2581 tggctggcgg cgcgatggcg ctgggaggcg gcatcgccgc ggccgttggc gccgggatgt
2641 cgttgaccga tgacgcgccg gccggacaga aggccgccgc cggcgccgag atcgcgctgc
2701 agttgacagg tggaacggtc gagctggctt cttccatcgc gttggcgctg ccgcggcgc
2761 gcggcgtgac cagcggcttg caggtggccg gggcgtcggc cggggcggct gccggcgcat
2821 tggccgcggc gctcagtccc atggagatct acggcctggt gcagcaatcg cactatgcgg
2941 tggcccagct gtatcgcgac aagacggccg ccgagggcgc cgtcgccggc gtctccgccg
3001 tcctgagcac ggtggggcg gcggtgtcga tcgccgcggc ggccagcgtg gtaggggccc
3061 cggtggcggt ggtcacttcc ttgctgaccg gggctctcaa cggcatcctg cgcggcgtgc
3121 agcagcccat catcgaaaag ctggccaacg attacgctca caagatcgac gagctgggcg
3181 ggccgcaagc gtacttcgag aaaaacctgc aggcgcgtca cgaacaactg gccaattcgg
3241 acggcctacg gaaaatgctg gccgacctgc aggccggttg gaacgccagc agcgtgatcg
3301 gggtgcagac gacagagatc tccaagtcgg cgctcgaact ggccgccatt accggcaacg
3361 cggacaacct gaaatccgtc gacgtgttcg tggaccgctt cgtccagggc gagcgggtgg
3421 ccggccagcc ggtggtcctc gacgtcgccg ccggcggcat cgatatcgcc agccgcaagg
3481 gcgagcggcc ggcgctgacg ttcatcacgc cgctggccgc gccaggagaa gagcagcgcc
3541 ggcgcacgaa aacgggcaag agcgaattca ccacattcgt cgagatcgtg ggcaagcagg
3601 accgctggcg catccgggac ggcgcggccg acaccaccat cgatctggcc aaggtggtgt
3661 cgcaactggt cgacgccaat ggcgtgctca agcacagcat caaactggat gtgatcggcg
3721 gagatggcga tgacgtcgtg cttccaatg cttcgcgcat ccattatgac ggcggcgcgg
3781 gcaccaacac ggtcagctat gccgccctgg gtcgacagga ttccattacc gtgtccgccg
3841 acggggaacg tttcaacgtg cgcaagcagt tgaacaacgc caacgtgtat cgcgaaggcg
3901 tggctaccca gacaaccgcc tacggcaagc gcacggagaa tgtccaatac cgccatgtcg
3961 agctggccg tgtcgggcaa gtggtggagg tcgacacgct cgagcatgtg cagcacatca
4021 tcggcgggc cggcaacgat tcgatcaccg gcaatgcgca cgacaacttc ctagccggcg
4081 ggtcgggcga cgacaggctg gatggcggcg ccggcaacga caccctggtt ggcggcgagg
4141 gccaaaacac ggtcatcggc ggcgccggcg acgacgtatt cctgcaggac ctgggggtat
4201 ggagcaacca gctcgatggc ggcgcgggcg tcgataccgt gaagtacaac gtgcaccagc
4261 cttccgagga gcgcctcgaa gcatggcg acacgggcat ccatgccgat cttcaaaagg
4321 gcacggtcga gaagtggccg gccctgaacc tgttcagcgt cgaccatgtc aagaatatcg
4381 agaatctgca cggctcccgc ctaaacgacc gcatcgccgg cgacgaccag gacaacgagc
4441 tctggggcca cgatggcaac gacacgatac gcggccgggg cggcgacgac atcctgcgcg
4501 gcggcctggg cctgacacg ctgtatggcg aggacggcaa cgacatcttc ctgcaggacg
4561 acgagaccgt cagcgatgac atcgacggcg gcgcggggct ggacaccgtc gactactccg
4621 ccatgatcca tccaggcagg atcgttgcgc cgcatgaata cggcttcggg atcgaggcgg
4681 acctgtccag ggaatgggtg cgcaaggcgt ccgcgctggg cgtggactat tacgataatg
4741 tccgcaatgt cgaaaacgtc atcggtacga gcatgaagga tgtgctcatc ggcgacgcgc
4801 aagccaatac cctgatgggc cagggcggcg acgataccgt cgcggcggc gacggcgatg
```

Fig. 33B

```
4861 atctgctgtt cggcggcgac ggcaacgaca tgctgtatgg cgacgccggc aacgacaccc
4921 tctacggggg gctgggcgac gataccc ttg aaggcggcgc gggcaacgat tggttcggcc
4981 agacgcaggc gcgcgagcat gacgtgctgc gcggcggaga tggggtggat accgtcgatt
5041 acagccagac cggcgcgcat gccggcattg ccgcgggtcg catcgggctg ggcatcctgg
5101 ctgacctggg cgccggccgc gtcgacaagc tgggcgaggc cggcagcagc gcctacgata
5161 cggtttccgg tatcgagaac gtggtgggca cggaactggc cgaccgcatc acgggcgatg
5221 cgcaggccaa cgtgctgcgc ggcgcgggtg gcgccgacgt gcttgcgggc ggcgagggcg
5281 acgatgtgct gctgggcggc gacggcgacg accagctgtc gggcgacgcc ggacgcgatc
5341 gcttgtacgg cgaagccggt gacgactggt tcttccagga tgccgccaat gccggcaatc
5401 tgctcgacgg cggcgacggc cgcgataccg tggatttcag cggcccgggc cggggcctcg
5461 acgccggcgc aaagggcgta ttcctgagct tgggcaaggg gttcgccagc ctgatggacg
5521 aacccgaaac cagcaacgtg ttgcgcaata tcgagaacgc cgtgggcagc gcgcgtgatg
5581 acgtgctgat cggcgacgca ggcgccaacg tcctcaatgg cctggcgggc aacgacgtgc
5641 tgtccggcgg cgctgcgac gatgtgctgc tgggcgacga gggctcggac ctgctcagcg
5701 gcgatgcggg caacgacgat ctgttcggcg ggcagggcga tgatacttat ctgttcgggg
5761 tcgggtacgg gcacgacacg atctacgaat cgggcggcgg ccatgacacc atccgcatca
5821 acgcggggc ggaccagctg tggttcgcg gccagggcaa cgacctggag atccgcattc
5881 tcggcaccga cgatgcactt accgtgcacg actggtatcg cgacgccgat caccgggtgg
5941 aaatcatcca tgccgccaac caggcggtag accaggcagg catcgaaaag ctggtcgagg
6001 caatggcgca gtatccggac cccggcgcgg cggcggctgc ccgccggcg gcgcgcgtgc
6061 cggacacgct gatgcagtcc ctggctgtca actggcgctg aagcgccgtg aatcacggcc
6121 cgcctgcctc gcgcggcggc gccgtctctt tgcgttcttc tccgaggtat ttcccatcat
6181 gacgtcgccc gcggcgcaat gcgccagcgt gcccgattcc gggttgctct gcctggtcat
6241 gctggctcgc tatcacggat tggcagccga tcccgagcag ttgcggcatg agttcgccga
6301 gaggcattct gtagcgaaac gatacagcct ggcggcgcgc cgggtcggcc tgaaagtgcg
6361 gcggcaccga cccgcgccgg cgcggctgcc acgcgcgccg ctgccggcca tcgcgctgga
6421 ccggtagggc ggctactttg tt (SEQ ID NO:14)
```

MTRNKFIPNKFSIISFSVLLFAISSSQAIEVNAMNEHYTESDIK
RNHKTEKNKTEKEKFKDSINNLVKTEFTNETLDKIQQTQDLLKKIPKDVLEIYSELGG
EIYFTDIDLVEHKELQDLSEBEKNSMNSRGEKVPFASRFVFEKKRETPKLIINIKDYA
INSEQSKEVYYEIGKGISLDIISKDKSLDPEFLNLIKSLSDDSDSSDLLFSQKFKEKL
ELNNKSIDINFIKENLTEFQHAFSLAFSYYFAPDHRTVLELYAPDMFEYMNKLEKGGF
EKISESLKKEGVEKDRIDVLKGEKALKASGLVPEHADAFKKIARELNTYILFRPVNKL
ATNLIKSGVATKGLNEHGKSSDWGPVAGYIPFDQDLSKKHGQQLAVEKGNLENKKSIT
EHEGEIGKIPLKLDHLRIEELKENGIILKGKKEIDNGKKYYLLESNNQVYEFRISDEN
NEVQYKTKEGKITVLGEKFNWRNIEVMAKNVEGVLKPLTADYDLFALAPSLTEIKKQI
PTKRMDKVVNTPNSLEKQKGVTNLLIKYGIERKPDSTKGTLSNWQKQMLDRLNEAVKY
TGYTGGDVVNHGTEQDNEEFPEKDNEIFIINPEGEFILTKNWEMTGRFIEKNITGKDY
LYYFNRSYNKIAPGNKAYIEWTDPITKAKINTIPTSAEFIKNLSSIRRSSNVGVYKDS
GDKDEFAKKESVKKIAGYLSDYYNSANHIFSQEKKRKISIFRGIQAYNEIENVLKSKQ
IAPEYKNYFQYLKERITNQVQLLLTHQKSNIEFKLLYKQLNFTENETDNFEVFQKIID
EK (SEQ ID NO:2)

encoded by
```
   1 ttacttttt atatactgaa ttaaaaagtc caagcactta tatcgtaata gatgctttct
  61 attgaccta tagtccttga agttacgact gaccaattat gagacgtttg cgctaacctg
 121 ctgaattcaa aatcggactt agaaatacac atatagaaat aaacaaccta atccatgtca
 181 ctgtaccgtt ttttactaa ataaacgaaa tcagtgtaaa aatgaacagc tgaactttat
```

Fig. 33C

```
    241 caacttagaa tctcttttt tactttaaat gcctagctgt ttttctaat
gtttgtattt
    301 ctaaatatat ttaaatatga attgtagctg tgtgccaaga gttataatta
atttaaataa
    361 gattatattt gtaaataaaa ttgtaattta acatgtagaa taaagagatt
tttagtttta
    421 ttaacaggat gaaaatccat aaaaccgtaa atgtgatttc taaattagtt
taaaataaaa
    481 aacaaggatt tgctcagact tgagatgaat atctaaatat caagaaccaa
aggaggttta
    541 agaatgacta gaaataaatt tatacctaat aagtttagta ttatatcctt
ttcagtatta
    601 ctatttgcta tatcctcctc acaggctata gaagtaaatg ctatgaatga
acattacact
    661 gagagtgata ttaaaagaaa ccataaaact gaaaaaata aaactgaaaa
agaaaaattt
    721 aaagacagta ttaataactt agttaaaaca gaatttacca atgaaacttt
agataaaata
    781 cagcagacac aagacttatt aaaaaagata cctaaggatg tacttgaaat
ttatagtgaa
    841 ttaggaggag aaatctattt tacagatata gatttagtag aacataagga
gttacaagat
    901 ttaagtgaag aagagaaaaa tagtatgaat agtagaggtg aaaaagttcc
gtttgcatcc
    961 cgttttgtat ttgaaaagaa aagggaaaca cctaaattaa ttataaatat
caaagattat
    1021 gcaattaata gtgaacaaag taaagaagta tattatgaaa ttggaaaggg
gatttctctt
    1081 gatattataa gtaaggataa atctctagat ccagagtttt taaatttaat
taagagtttta
    1141 agcgatgata gtgatagtag cgaccttta tttagtcaaa aatttaaaga
gaagctagaa
    1201 ttgaataata aaagtataga tataaatttt ataaaagaaa atttaactga
atttcagcat
    1261 gcgttttctt tagcgttttc ttattatttt gcacctgacc atagaacggt
attagagtta
    1321 tatgcccccg acatgtttga gtatatgaat aagttagaaa aaggggggatt
tgagaaaata
    1381 agtgaaagtt tgaagaaaga aggtgtggaa aaagatagga ttgatgtgct
gaaaggagaa
    1441 aaagcactta agcttcagg tttagtacca gaacatgcag atgcttttaa
aaaaattgct
    1501 agagaattaa atacatatat tctttttagg cctgttaata agttagctac
aaaccttatt
    1561 aaaagtggtg tggctacaaa gggattgaat gaacatggaa agagttcgga
ttggggccct
    1621 gtagctggat acataccatt tgatcaagat ttatctaaga agcatggtca
acaattagct
    1681 gtcgagaaag gaaatttaga aaataaaaaa tcaattacag agcatgaagg
tgaaataggt
    1741 aaaataccat taaagttaga ccatttaaga atagaagagt taaaggaaaa
tgggataatt
    1801 ttgaagggta aaaagaaat tgataatggt aaaaaatatt atttgttaga
atcgaataat
    1861 caggtatatg aatttagaat tagcgatgaa acaacgaag tacaatacaa
gacaaaagaa
```

Fig. 33D

```
     1921 ggtaaaatta ctgttttagg ggaaaaattc aattggagaa atatagaagt
gatggctaaa
     1981 aatgtagaag gggtcttgaa gccgttaaca gctgactatg atttatttgc
acttgcccca
     2041 agtttaacag aaataaaaaa acaaataccc acaaaaagaa tggataaagt
agttaacacc
     2101 ccaaattcat tagaaaagca aaaggtgtt actaatttat tgattaaata
tggaattgag
     2161 aggaaaccgg attcaactaa gggaacttta tcaaattggc aaaaacaaat
gcttgatcgt
     2221 ttgaatgaag cagtcaaata tacaggatat acagggggg atgtggttaa
ccatggcaca
     2281 gagcaagata atgaagagtt tcctgaaaaa gataacgaaa tttttataat
taatccagaa
     2341 ggtgaattta tattaactaa aaattgggag atgacaggta gatttataga
aaaaaacatt
     2401 acgggaaaag attatttata ttattttaac cgttcttata ataaaatagc
tcctggtaat
     2461 aaagcttata ttgagtggac tgatccgatt acaaaagcca aaataaatac
catccctacg
     2521 tcagcagagt ttataaaaaa cttatccagt atcagaagat cttcaaatgt
aggagtttat
     2581 aaagatagtg gcgacaaaga cgaatttgca aaaaaagaaa gcgtgaaaaa
aattgcagga
     2641 tatttgtcag actattacaa ttcagcaaat catatttttt ctcaggaaaa
aaagcgtaaa
     2701 atatcaatat ttcgtggaat ccaagcctat aatgaaattg aaaatgttct
aaaatctaaa
     2761 caaatagcac cagaatacaa aaattatttt caatatttaa aggaaaggat
taccaatcaa
     2821 gttcaattgc ttctaacaca tcaaaaatct aatattgaat ttaaattatt
gtataaacaa
     2881 ttaaacttta cagaaaatga aacggataat tttgaggtct tccaaaaaat
tattgatgaa
     2941 aaataaatat atataattgt ttttctgaaa attcatcatt ttaaagaaga
cactaggaat
     3001 taaatagatg tattgaatag ttatagtaat ggtcttgtat ggacataccg
cttatacttt
     3061 gggaggtagt agatattaaa caacatatag caaatgaact ggagtgtaga
tcaaaagaaa
     3121 ttttttctaaa aaatatctca tctttaataa aaaatggcac tgtatataaa
gcagcaacag
     3181 ataaaattat tacctatatg caaaagattt aaatattgac cttgtaatag
gcatggaatc
     3241 tcgagggttt attttggtt gcccagtttc atatgctttg ggaataggtt
ttataccggt
     3301 tcgtaaatta gggaccctgg ttggatttga taatgagaac gtaaaagata
ttctaacaat
     3361 aaataatgat gcgattaacc aggccacgtg tgttaatact gatgtatgtg
taactactgg (SEQ ID NO:15)
``` mtrnkfipnk fsiisfsvll faisssqaie vnamnehyte sdikrnhkte knktekekfk
dsinnlvkte ftnetldkiq qtqdllkkip kdvleiysel ggeiyftdid lvehkelqdl
seeeknsmns rgekvpfasr fvfekkretp kliinikdya inseqskevy yeigkgisld
iiskdksldp eflnliksls ddsdssdllf sqkfkeklel nnksidinfi kenltefqha
fslafsyyfa pdhrtvlely apdmfeymnk lekggfekis eslkkegvek dridvlkgek

Fig. 33E

```
alkasglvpe hadafkkiar elntyilfrp vnklatnlik sgvatkglnv hgkssdwgpv
agyipfdqdl skkhgqqlav ekgnlenkks itehegeigk iplkldhlri eelkengiil
kgkkeidngk kyyllesnnq vyefrisden nevqyktkeg kitvlgekfn wrnievmakn
vegvlkplta dydlfalaps lteikkqipq kewdkvvntp nslekqkgvt nllikygier
kpdstkgtls nwqkqmldrl neavkytgyt ggdvvnhgte qdneefpekd neifiinpeg
efiltknwem tgrfieknit gkdylyyfnr synkiapgnk ayiewtdpit kakintipts
aefiknlssi rrssnvgvy

```
igtsmkdvli gdaqantlmg qggddtvrgg dgddllfggd gndmlygdag ndtlygglgd
dtleggagnd wfgqtqareh dvlrggdgvd tvdysqtgah agiaagrigl giladlgagr
vdklgeagss aydtvsgien vvgteladri tgdaqanvlr gaggadvlag gegddvllgg
dgddqlsgda grdrlygeag ddwffqdaan agnlldggdg rdtvdfsgpg rgldagakgv
flslgkgfas lmdepetsnv lrnienavgs arddvligda ganvlnglag ndvlsggagd
dvllgdegsd llsgdagndd lfggqgddty lfgvgyghdt iyesggghdt irinagadql
wfarqgndle irilgtddal tvhdwyrdad hrveiihaan qavdqagiek lveamaqypd
pgaaaaappa arvpdtlmqs lavnwr    (SEQ ID NO:6)

mqqshqagya naadresgip aavldgikav akeknatlmf rlvnphstsl iaegvatkgl
gvhakssdwg lqagyipvnp nlsklfgrap eviaradndv nsslahghta vdltlskerl
dylrqaglvt gmadgvvasn hagyeqfefr vketsdgrya vqyrrkggdd feavkvigna
agipltadid mfaimphlsn frdsarssvt sgdsvtdyla rtrraaseat ggldreridl
lwkiaragar savgtearrq frydgdmnig vitdfelevr nalnrrahav gaqdvvqhgt
eqnnpfpead ekifvvsatg esqmltrgql keyigqqrge gyvfyenray gvagkslfdd
glgaapgvpg grsksspdvl etvpaspglr rpslgaverq dsgydsldgv gsrsfslgev
sdmaaveaae lemtrqvlha garqddaepg vsgasahwgq ralqgaqava aaqrlvhaia
lmtqfgrags tntpqeaasl saavfglgea ssavaetvsg ffrgssrwag gfgvaggama
lgggiaaavg agmsltddap agqkaaagae ialqltggtv elassialal aaargvtsgl
qvagasagaa agalaaalsp meiyglvqqs hyadqldkla qessaygyeg dallaqlyrd
ktaaegavag vsavlstvga avsiaaaasv vgapvavvts lltgalngil rgvqqpiiek
landyarkid elggpqayfe knlqarheql ansdglrkml adlqagwnas svigvqttei
sksalelaai tgnadnlksa dvfvdrfiqg ervagqpvvl dvaaggidia srkgerpalt
fitplaapge eqrrrtktgk sefttfveiv gkqdrwrird gaadttidla kvvsqlvdan
gvlkhsikle viggdgddvv lanasrihyd ggagtntvsy aalgrqdsit vsadgerfnv
rkqlnnanvy regvatqkta ygkrtenvqy rhvelarvgq lvevdtlehv qhiiggagnd
sitgnahdnf laggagddrl dggagndtlv ggeghntvvg gagddvflqd lgvwsnqldg
gagvdtvkyn vhqpseerle rmgdtgihad lqkgtvekwp alnlfsvdhv knienlhgss
lndsiagddr dnelwgddgn dtihgrggdd ilrgglgldt lygedgndif lqddetvsdd
idggagldtv dysamihagk ivapheygfg ieadlsegwv rkaarrgmdy ydsvrsvenv
igtsmkdvli gdaqantlmg qggddtvrgg dgddllfggd gndmlygdag ndtlygglgd
dtleggagnd wfgqtpareh dvlrggagvd tvdysqagah agvatgrigl giladlgagr
vdklgeagss aydtvsgien vvgteladri tgdaqanvlr gaggadvlag gegddvllgg
dgddqlsgda grdrlygeag ddwffqdaan agnlldggdg ndtvdfsgpg rgldagakgv
flslgkgfas lmdepetsnv lrhienavgs vrddvligda ganvlnglag ndvlsggagd
dvllgdegsd llsgdagndd lfggqgddty lfgagyghdt iyesggghdt irinagadql
wfarqgndle irilgtddal tvhdwyrdad hrveaihaan qaidpagiek lveamaqypd
pgaaaaappa arvpdtlmqs lavnwr    (SEQ ID NO:7)

mpfsnshntq klrfpaedef pdlsshnnhm akvltpelya elrakctpsg ftlddaiqtg
vdnpghpyim tvgavagdee sydvfkdlfd piieerhggy qpsdehktdl npdnlqggdd
ldpnyvlssr vrtgrsirgf clpphcsrge rraieklave alssldgdls gryyalksmt
eaeqqqlidd hflfdkpvsp lllasgmard wpdargiwhn dnktflvwin eedhlrvism
qkggnmkevf trfctgltqi etlfksknye fmwnphlgyi ltcpsnlgtg lragvhiklp
hlgkhekfse vlkrlrlqkr gtggvdtaav ggvfdvsnad rlgfsevelv qmvvdgvkll
iemeqrleqg qaiddlmpaq k    (SEQ ID NO:8)

mpfgnthnkf klnykpqeey pdlskhnnhm akvltpdlyn klrdketpsg ftlddviqtg
vdnpghpfim tvgcvagdee sytvfkdlfd piiqdrhggy kptdkhktdl nhenlkggdd
ldpnyvlssr vrtgrsikgy tlpphcsrge rraveklsve alnsltgefk gkyyplksmt
eqeqqqlidd hflfdkpvsp lllasgmard wpdargiwhn dnksflvwvn eedhlrvism
ekggnmkevf rrfcvglqki eeifkkaghp fmwnehlgyv ltcpsnlgtg lrggvhvkla
nlskhpkfee iltrlrlqkr gtggvdtaav gavfdisnad rlgsseveqv qlvvdgvklm
vemekklekg qsiddmipaq k    (SEQ ID NO:9)

mpfsnshnal klrfpaedef pdlsahnnhm akvltpelya elrakstpsg ftlddviqtg
```

Fig. 33G

```
vdnpghpyim tvgcvagdee syevfkdlfd piiedrhggy kpsdehktdl npdnlqggdd
ldpnyvlssr vrtgrsirgf clpphcsrge rraieklave alssldgdla gryyalksmt
eaeqqqlidd hflfdkpvsp llsasgmard wpdargiwhn dnktflvwvn eedhlrvism
qkggnmkevf trfctgltqi etlfkskdye fmwnphlgyi ltcpsnlgtg lragvhiklp
nlgkhekfse vlkrlrlqkr gtggvdtaav ggvfdvsnad rlgfsevelv qmvvdgvkll
iemeqrleqg qaiddlmpaq k  (SEQ ID NO:10)

mftkivatlg pstdrlpdit allskvhgvr inmshaspse vearvnavrk yeetsgryia
iiadlrgpsv rtglmrplqi tagarvsfkl aekgdgfvpv prreffevie egdevlmldg
klvlriisaa qtsaeaesls sgvissnkai vvkgkeyhie qpveediral qtlsrfrddv
dyvalslvrd gadvrkmrsv veeagltsgi makietksav dkieeiinaa dyiviargdl
alhygleyip kvqrllvers lsagrpvava tqlldsmqtn ttptraevnd vyttaslgvd
slwltnetas gehpleavdw lrrivsqvef grlkaaspad ardrfakavv dmaedmggei
avysmtgtla kriakfrpmt tvyvgvnerr larmlelred vgahmgprac gragaylrgg
preaplqilr qsldshvwaq rrhtyy  (SEQ ID NO:11)

mskphseagt afiqtqqlha amadtflehm crldidsppi tarntgiict igpasrsvet
lkemiksgmn varlnfshgt heyhaetikn vrtatesfas dpilyrpvav aldtkgpeir
tglikgsgta evelkkgatl kitldnayme kcdenilwld yknickvvev gskiyvddgl
islqvkqgka dflvteveng gslgskkgvn lpgaavdlpa vsekdiqdlk fgveqdvdmv
fasfirkasd vhevrkvlge kgknikiisk ienhegvrrf deileasdgi mvargdlgie
ipaekvflaq kmmigrcnra gkpvicatqm lesmikkppp traegsdvan avldgadcim
lsgetakgdy pleavrmqhl iareaeaaiy hlqlfeelrr lapitsdpte atavgaveas
fkccsgaiiv ltksgrsahq varyrprapi iavtrnpqta rqahlyrgif pvlckdpvqe
awaedvdlrv nfamnvgkar gffkkgdvvi vltgwrpgsg ftntmrvvpv p (SEQ ID NO:12)

meeklkktki ifvvggpgsg kgtqcekivq kygythlstg dllrsevssg sargkklsei
mekgqlvple tvldmlrdam vakvntskgf lidgyprevq qgeeferrig qptlllyvda
gpetmtqrll krgetsgrvd dneetikkrl etyykatepv iafyekrgiv rkvnaegsvd
svfsqvcthl dalk  (SEQ ID NO:13)
```

Fig. 33H

… # ADP DETECTION BASED LUMINESCENT PHOSPHOTRANSFERASE OR ATP HYDROLASE ASSAY

CROSS-REFERENCE TO RELATED APPLICATIONS

This application is a divisional of U.S. application Ser. No. 12/460,573 filed Jul. 20, 2009, which claims priority to U.S. Provisional Application Nos. 61/182,372 filed May 29, 2009, 61/170,308 filed Apr. 17, 2009 and 61/082,775 filed Jul. 22, 2008, the disclosures of which are incorporated by reference herein.

BACKGROUND

Due to their physiological relevance, variety and ubiquitousness, transferases, especially kinases, have become one of the most important and widely studied families of enzymes in biochemical and medical research. Studies have shown that protein and lipid kinases are key regulators of many cell functions, including signal transduction, transcriptional regulation, cell motility, cell division and cellular responses to drugs, toxins, and pathogens.

Protein kinases play crucial roles in the modulation of a wide variety of cellular events. These enzymes act by transferring phosphate residues to certain amino acids in intracellular polypeptides to bring about the activation of these protein substrates and set in motion a cascade of activation controlling events including growth, differentiation and division of cells. Protein kinases have been extensively studied in the field of tumour biology. A lack of controlled activity of kinases in cells is believed to lead to the formation of tumours. The pharmaceutical industry is constantly in search of drugs that target these kinases to help with the treatment of a wide variety of tumours. There are over 500 protein kinases (about 2 to 2.5% of the human genome) that are involved in the regulation of cell functions. They occur as both transmembrane and cytosolic enzymes, and they phosphorylate serine, threonine and tyrosine amino acid residues. Based on these substrate specificities, the kinases are divided into two groups, the serine/threonine kinases and tyrosine kinases.

Serine/threonine kinases include cyclic AMP and cyclic GMP dependent protein kinases, calcium and phospholipid dependent protein kinase, calcium and calmodulin-dependent protein kinases, casein kinases, cell cycle protein kinases and others. These kinases are usually cytoplasmic or associated with the particulate fractions of cells, possibly by anchoring proteins.

Tyrosine kinases phosphorylate tyrosine residues. These particular kinases are present in much smaller numbers but play an equally important role in cell regulation. These kinases include several soluble enzymes such as the src family of protein kinases and receptors for growth factors such as epidermal growth factor receptor, insulin receptor, platelet derived growth factor receptor, and others. Studies have indicated that many tyrosine kinases are transmembrane proteins with their receptor domains located on the outside of the cell and their kinase domains on the inside.

Lipid kinases also play important roles in the intracellular signal transduction and have been grouped into four major classes. Exemplary lipid kinases include PI3 kinases and phosphatidylinositol 4-kinases.

Sugar kinases and other phosphotransferases also play a major role in cellular metabolism, proliferation and apoptosis.

With phosphorylation events involved in so many cell functions and diseases, identifying kinase activity is tremendously important. Current types of assays used to measure kinase activity include Fluorescence Resonance Energy Transfer (FRET) assays, Fluorescent Polarization (FP) assays, and assays based on radioactivity such as Scintillation Proximity Assay (SPA). FRET assays used to detect kinase activity utilize a protein or peptide substrate that is linked to a fluorescent molecule and another fluorescently labeled probe. The two fluorescent molecules are in close proximity only when the substrate is phosphorylated and recognized by the labeled probe. Thus, when phosphorylated by a kinase, the energy of the label is passed to the fluorescent molecule (the acceptor) through resonance. The ability of a higher energy donor fluorophore to transfer energy directly to a lower energy acceptor molecule causes sensitized fluorescence of the acceptor molecule and simultaneously quenches the donor fluorescence. In this case, the fluorescence of the donor is "quenched" by the proximity to the acceptor and the energy of the donor is transferred to the acceptor in a non-radioactive manner. The efficiency of energy transfer is dependent on the distance between the donor and acceptor chromophores according to the Forster equation. In most cases, no FRET is observed at distances of greater than 100 angstroms, and thus the presence of FRET is a good indicator of close proximity. Accordingly, in a FRET assay to detect kinase activity that employs a protein or peptide substrate that is linked to a fluorescent molecule and another fluorescently labeled probe, if the kinase is inhibited, the two fluorescent molecules remain separated and no FRET occurs.

FRET based assays have a number of drawbacks including a large number of false hits, e.g., due to fluorescent interference with the compounds being tested, a narrow dynamic range, and performance issues associated with the antibody employed in the assay.

FP assays are based on binding of a high affinity binding reagent, such as an antibody, a chelating atom, or the like, to a fluorescent labeled molecule. For example, an antibody that binds to a phosphorylated fluorescent labeled peptide but not a non-phosphorylated fluorescent labeled peptide can be used for a kinase assay. Other methods utilize a fluorescent labeled antibody that binds ADP, the other kinase reaction product, in monitoring kinase activity. When the fluorescent label is excited with plane polarized light, it emits light in the same polarized plane as long as the fluorescent label remains stationary throughout the excited state (duration of the excited state varies with fluorophore, and is 4 nanoseconds for fluoroscein). If polarized light is used to excite the fluorophore, the emission light intensity can be monitored in both the plane parallel to the plane of polarization (the excitation plane) and in the plane perpendicular to the plane of polarization. An FP assay requires a high affinity binding reagent, e.g., an antibody, capable of binding with high specificity to the fluorescent labeled molecule. The time consuming and costly optimization of an antibody binding with specific fluorescent labeled molecules such as peptides is required where antibodies are used. Additionally, in the FP assay there is the potential for phosphorylated protein and other reaction components, e.g., lipids and detergents, to interfere with the polarization.

Kinase assays that use radioactive labels include SPA. In SPA, modified ligand-specific or ligand-capturing molecules are coupled to fluoromicrospheres, which are solid-phase support particles or beads impregnated with substances that emit energy when excited by radioactively labeled molecules. When added to a modified ligand such as radio-labeled phosphopeptide in a mixture with nonphosphorylated peptide, only the phosphopeptide is captured on a fluoromicrosphere, bringing any bound radiolabeled peptide close enough to allow the radiation energy emitted to activate the fluoromicrosphere and emit light energy. If the concentration of fluoromicrospheres is optimized, only the signal from the radiolabeled ligand bound to the target is detected, eliminating the need for any separation of bound and free ligand. The level of light energy emitted may be measured in a liquid scintillation counter and is indicative of the extent to which the ligand is bound to the target. A SPA requires the fluoromicrospheres to settle by gravity or be centrifuged, adding an additional step and time to the assay. In addition, due to the high energy of $^{32}P$ used in this assay, most of the radioactivity passes through without being captured by the fluoromicrospheres.

Other methods also have been developed for detecting kinase activity that are based on luminescence detection, either by bioluminescence or chemiluminescences. Generally, these methods rely on specific substrates and antibodies, the use of microchips and fluorescent label probes, substrate concentration in a sample, the use of multiple steps and reagents (U.S. Pat. No. 6,599,711) or are limited to specific kinases (Sala-Newby et al., 1992).

Many currently available kinase assays perform well with enzymes that consume a high amount of ATP during the reaction, but are not sensitive enough to detect the small changes in ATP amount that define kinases with low ATP turnover, like growth factor receptor kinases. On the contrary, the available assays that could analyze this type of enzyme are specific for a subset of kinases and/or not sensitive enough to be used with a broad range of kinases.

SUMMARY OF THE INVENTION

The invention provides compositions and methods to determine or detect the activity of enzymes, including phosphotransferases such as kinases (e.g., protein, lipid, and sugar kinases) and ATP hydrolases such as ATPases, e.g., HSP90, that employ ATP as a substrate and form ADP as a product by monitoring changes in ADP. In order to monitor ADP formation, ADP is converted to ATP and an ATP-dependent bioluminescent reaction, such as a luciferase/luciferin reaction, is employed to detect ATP. Prior to the bioluminescent reaction which requires ATP, e.g., a luciferase-mediated reaction, and the conversion of ADP to ATP by a nucleotide kinase such as an ADP to ATP converting enzyme, the ATP remaining after the kinase or ATPase reaction is substantially reduced, e.g., to less than 2,%, 1%, 0.75%, 0.5%, 0.25%, 0.1%, 0.075%, 0.05%. 0.025%, 0.02%, 0.01%, 0.001%, 0.0001% or less of the ADP formed or amount of ATP initially present in the reaction mixture, or eliminated. In one embodiment, an adenylate cyclase such as a bacterial adenylate cyclase is employed to convert the residual ATP to cAMP, a product that does not have or does not have a significant effect on an ADP converting enzyme reaction or on an ATP-dependent bioluminescent reaction. Once the residual ATP is reduced to a minimum or eliminated, the ADP formed in the kinase or ATPase reaction is converted to ATP using an enzyme capable of converting ADP to ATP, such as adenylate kinase (myokinase), creatine kinase, or pyruvate kinase and the like. In some embodiments, the activity of the enzyme that converts the ATP to the non-ADP product is inhibited prior to converting the ADP in the solution to ATP or performing the bioluminescent reaction. When this is the case, the enzyme that converts the ATP to the non-ADP product will not interfere with production of ATP from the ADP or the detection of the ATP with the bioluminescent reaction. The newly formed ATP is then measured using light generated by the bioluminescent reaction, e.g., measured with a luminometer. In general, the methods to convert the ADP to ATP and then the ATP to light include adding a composition comprising a bioluminescence generating enzyme such as a luciferase, e.g., a native or recombinant luciferase such as a firefly or click beetle luciferase, a bioluminogenic substrate such as luciferin or a luciferin derivative that is a substrate of the luciferase, an ADP to ATP converting enzyme such as a kinase and optionally (if needed) a substrate for the ADP to ATP converting enzyme, to a reaction mixture having ADP generated by a kinase or ATPase reaction. The composition may be admixed before use by adding a solution comprising reagents other than luciferase to lyophilized luciferase. In another embodiment, the composition may be admixed before use by adding a solution comprising reagents other than luciferase and luciferin or luciferin derivative to lyophilized luciferase and lyophilized luciferin or a derivative thereof.

Those skilled in the art recognize that the bioluminescent reaction indicates the presence or absence of ADP in the solution or provides a measure of the ADP in the solution. When a measure of the ADP in the solution is desired, the results from the bioluminescent reaction may be compared against one or more standards or control reactions.

The invention also provides compositions and kits that are used to detect phosphotransferase activity, such as kinase activity, or ATP hydrolase activity, such as ATPase activity, in a sample. In one embodiment, the invention provides a composition or kit comprising an isolated enzyme that converts ATP to a non-ADP substrate, for example, adenylate cyclase which converts ATP to cAMP and a pyrophosphatase. The kit may further include one or more of a kinase enzyme, a substrate for the kinase enzyme, an enzyme that converts ADP to ATP, for example, pyruvate kinase, a phosphate donor that can be used by the enzyme that converts ADP to ATP, for example, phosphoenol pyruvate, a luciferase enzyme and/or a substrate for the luciferase enzyme, for example luciferin or a derivative thereof, The kit can optionally include one or more of an inhibitor of a phosphotransferase or an ATP hydrolase that converts ATP to ADP, or an effective amount of an activator of the adenylate cyclase.

Exemplary adenylate cyclases that may be used in the methods, kits or compositions described herein include but are not limited to bacterial adenylate cyclases such as those from *Bortedella pertussis*, *Bacillus anthracis*, *Pseudomonas aeruginosa*, *Haemophilus influenzae*, *Escherchia coli*, *Bdellovibrio* spp., *Vibrio* spp., *Yersinia* spp., *Erwinia* spp., *Enterobacter* spp., or *Shewanella* spp., or a fragment of a full length bacterial adenylate cyclase with adenylate cyclase activity, e.g., a recombinant fragment of a bacterial adenylate cyclase with adenylate cyclase activity (e.g., see FIG. 4), a eukaryotic adenylate cyclase such as a calmodulin activated eukaryotic adenylate cyclase, an algal adenylate cyclase such as a *Spirulina platenis* adenylate cyclase, porcine, non-human primate, canine, bovine, rodent, or human adenylate cyclase, e.g., ADCY1, ADCY2, ADCY3, ADCY4, ADCY5, ADCY6, ADCY7, ADCY8, ADCY9 or ADCY10, or adenylate cyclase isoforms I, III and VIII, which are stimulated by $Ca^{2+}$/calmodulin, or isoforms V and VI which are inhibited by $Ca^{2+}$ in a calmodulin-independent manner, or a fragment thereof with adenylate cyclase activity.

In one embodiment, the composition or kit comprises one or more inhibitors of a kinase. In one embodiment, the composition or kit comprises one or more inhibitors of ATPase. In another embodiment, if the composition does not include an inhibitor(s) of a phosphotransferase, such as a kinase, or an ATP hydrolase, such as an ATPase, the activity of the phosphotransferase or ATP hydrolase may be inactivated by other means, e.g., using heat, prior to adding the adenylate cyclase. However, the inactivation of the phosphotransferase or ATP hydrolase may not be needed in order to carry out the present invention. In one embodiment, the composition or kit comprises isolated bacterial adenylate cyclase, such as one that is activatable, e.g., by an activator such as calmodulin. In one embodiment, the composition or kit comprises an isolated calmodulin stimulatable bacterial adenylate cyclase, staurosporin, a pyrophosphatase, and optionally calmodulin. A suitable pyrophosphatase includes yeast pyrophosphatase. In another embodiment, the composition or kit comprises one or more inhibitors of a kinase or ATPase, a pyrophosphatase and an activator of adenylate cyclase. In one embodiment, a kit may comprise a first composition comprising one or more of one or more inhibitors of a kinase or ATPase, a pyrophosphatase and an activator of adenylate cyclase and a second composition comprising an adenylate cyclase. Kits may include each reagent in a separate container or may combine two or more reagents in a container.

Also provided is a composition or kit comprising an inhibitor (i.e., an ATP binding site competitor, e.g., an ATP analog, or a catalytic domain inhibitor such as PMEA (9-(2-phosphorylmethoxyethyl)-adenine) or PMEApp analogs) of an adenylate cyclase and optionally an isolated ADP to ATP converting enzyme that converts ADP to ATP. In one embodiment, the composition or kit comprises an inhibitor of an activated bacterial adenylate cyclase, e.g., an inhibitor of a calmodulin activated bacterial adenylate cyclase or a fragment thereof with adenylate cyclase activity and at least one ADP to ATP converting enzyme, such as adenylate kinase, creatine kinase, or pyruvate kinase. In one embodiment, the composition or kit comprises an inhibitor of an adenylate cyclase and a substrate for isolated ADP to ATP converting enzyme. In one embodiment, the composition or kit further comprises the isolated ADP to ATP converting enzyme. In one embodiment, the composition or kit further comprises a bioluminescent enzyme such as luciferase, and a substrate for the bioluminescent enzyme, e.g., D-luciferin.

In addition, the invention provides a composition which comprises an ADP to ATP converting enzyme, an agent for a bioluminescent enzyme-mediated reaction which include a detergent in an amount that inactivates adenylate cyclase and optionally a substrate for the ADP to ATP converting enzyme.

Further provided is a method to convert ATP in a mixture comprising ADP and ATP, to cAMP and PPi or cAMP and Pi. In one embodiment, the method includes providing a first reaction mixture for a phosphotransferase, e.g., a kinase, or an ATP hydrolase, e.g., an ATPase, that converts ATP to ADP, comprising ATP and a sample suspected of having the phosphotransferase or ATP hydrolase and contacting the first reaction mixture with an amount of an isolated active adenylate cyclase and a pyrophosphatase, and optionally one or more inhibitors of the phosphotransferase or ATP hydrolase, effective to yield a second reaction mixture comprising cAMP, Pi, and if the phosphotransferase or ATP hydrolase is present in the sample, ADP. In one embodiment, the method includes providing a first reaction mixture for a kinase or ATPase that converts ATP to ADP comprising ATP and a sample suspected of having the kinase or ATPase and contacting the first reaction mixture with an amount of an isolated active adenylate cyclase and optionally one or more inhibitors of the kinase or ATPase effective to yield a second reaction mixture comprising cAMP, PPi, and if the kinase or ATPase is present in the sample, ADP. The amount of Pi or PPi generated does not substantially inhibit an ADP to ATP converting enzyme reaction or an ATP-dependent bioluminescent enzyme reaction. In one embodiment, the second reaction mixture is contacted with an inhibitor of the adenylate cyclase, an ADP to ATP converting enzyme, optionally a substrate for the ADP to ATP converting enzyme, and also optionally a bioluminescent enzyme and a substrate therefore to yield a third reaction mixture. After addition of a bioluminescent enzyme and a substrate therefore, such as luciferase and luciferin, either at the same time as the inhibitor of the adenylate cyclase and the ADP to ATP converting enzyme, or after addition the inhibitor of the adenylate cyclase and the ADP to ATP converting enzyme, luminescence in the third reaction mixture is detected. In one embodiment, the reaction mixtures for converting ADP to ATP and the bioluminescent enzyme are combined in one solution. Control reactions include reactions that do not include a phosphotransferase or ATP hydrolase.

In addition, the invention provides a method to identify modulators of a phosphotransferase such as a kinase or an ATP hydrolase, e.g., ATPase, that convert ATP to ADP. The method includes providing a first reaction mixture comprising one or more test agents, one or more phosphotransferases or ATP hydrolases that convert ATP to ADP, e.g., one or more isolated kinases or cells expressing recombinant kinase or a lysate thereof, and ATP, contacting the first reaction mixture with an amount of at least one isolated active adenylate cyclase and at least one pyrophosphatase, and optionally one or more inhibitors of the one or more phosphotransferases or ATP hydrolases, to yield a second reaction mixture comprising cAMP, Pi and the ADP. The second reaction mixture is contacted with one or more inhibitors of the adenylate cyclase, one or more ADP to ATP converting enzymes, a bioluminescent enzyme and a substrate therefore, such as luciferase and luciferin, to yield a third reaction mixture. After addition of the bioluminescent enzyme and a substrate therefor, either at the same time as the inhibitor of the adenylate cyclase and the ADP to ATP converting enzyme, or after addition of the inhibitor of the adenylate cyclase and the ADP to ATP converting enzyme, luminescence in the third reaction mixture is detected. In one embodiment, the reaction mixture for converting ADP to ATP and the bioluminescent enzyme reactions are combined in one solution. Control reactions include reactions that do not include a phosphotransferase or ATP hydrolase or may include a known inhibitor or activator of the phosphotransferase or ATP hydrolase.

For example, the agent(s) to be tested in the method may be identified as a kinase or ATPase inhibitor if the activity of the kinase or the ATPase in the presence of the agent(s) is lower than the activity of the kinase or ATPase in the absence of the agent(s). In one embodiment, the agent to be tested is identified as a kinase or ATPase inhibitor if the activity of the kinase or ATPase in the presence of the agent(s) is less than 95% of the activity of the kinase or ATPase in the absence of the agent(s). In one embodiment, the agent to be tested is identified as a kinase or ATPase inhibitor if the activity of the kinase or ATPase in the presence of the agent(s) is less than 80%, 70%, 60%, 50%, 40%, 30%, 20%, 10%, 5%, 2%, 1% or less of the activity of the kinase or ATPase in the absence of the agent(s). In yet another embodiment, the agent to be tested is identified as a kinase or ATPase inhibitor if the activity of the kinase or ATPase in the presence of the agent(s) is less than 50% of the activity of the kinase or ATPase in the absence of the agent(s).

In another example, the agent to be tested is identified as a kinase or ATPase activator if the activity of the kinase or the ATPase in the presence of the agent(s) is higher than the activity of the kinase or the ATPase in the absence of the agent(s). In one embodiment, the agent to be tested is identified as a kinase or ATPase activator if the activity of the kinase or ATPase in the presence of the agent(s) is more than 10% greater that the activity of the kinase or ATPase in the absence of the agent(s). In one embodiment, the agent to be tested is identified as a kinase or ATPase activator if the activity of the kinase or ATPase in the presence of the agent(s) is more than 20%, 30%, 40%, 50%, 75%, 100% or 200% greater than the activity of the kinase or ATPase in the absence of the agent(s). In a further embodiment, the agent to be tested is identified as a kinase or ATPase activator if the kinase or ATPase in the presence of the agent(s) at least 50% greater than the activity of the kinase or ATPase in the absence of the agent(s).

The invention thus provides methods, compositions and kits that are used for detection of phosphotransferase, e.g., kinase, or ATP hydrolase, e.g., ATPase, activity in a sample. In some embodiments, the methods, compositions and kits are antibody free, and the homogeneous methods described herein are fast, sensitive, simple, and non-radioactive. The methods are convenient and can be used with any instrumentation platform. Reagents required can be designed with relative ease and may be synthesized readily. The reagents may facilitate measurement of activity in many samples in a high throughput format over a long period of time due to the high signal stability generated by a luminogenic reaction, thus eliminating the need for luminometers with reagent injectors and allowing for batch-mode processing of multiple samples.

In one embodiment, the present methods can be performed in a single well in a multi-well plate making them suitable for use as high throughput screening methods. The method may be employed with various amounts of ATP, kinase or ATPase, test agents, or any combination thereof, and at different reaction temperatures. The method of the present invention can be utilized to detect activity over a wide range of ADP or ATP concentrations, generally from about 1 µM or less to about 5 mM or more of ADP or ATP. In some embodiments, ADP or ATP concentration as low as 0.5 µM, 0.25 µM, 0.1 µM, 0.01 µM, 1 nM, 0.1 nM, 0.01 nM, 1 picoM or less may be detected using the methods, compositions or kits described herein. In some embodiments, 20 nM of ADP in 10 micoliters of solution (0.2 pM ADP) can be detected. For instance, the method may be used to detect kinase activity at low concentration levels of ATP, generally below 5 µM of ATP, as well as in the range of about 1 mM to about 5 mM of ATP. Although the methods of the invention may be used with a sample containing virtually any amount of ADP or ATP.

The kits of the invention are designed to detect and quantitate phosphotransferase, e.g., kinase, or ATP hydrolase, e.g., ATPase, activity in a sample or to determine the effects of test agents, e.g., those in a library such as a combinational library, on phosphotransferase, e.g., kinase, or ATP hydrolase, e.g., ATPase, activity. In one embodiment, a kit that is used to detect kinase or ATPase activity in a sample may comprise lyophilized luciferase, or lyophilized luciferase and luciferin, in one container, while another container contains reconstitution buffer with one or more ADP to ATP converting enzymes or a substrate therefore, or an inhibitor of adenylate cyclase, or a combination thereof. The kit may also supply magnesium or other cations such as manganese or calcium. To facilitate the use of control experiments with known concentrations of ADP or ATP, or a kinase or ATPase, a container that has ADP, ATP, isolated kinase or isolated ATPase, may also be supplied in such kits. The kit may also supply a compound that inhibits kinase or ATPase activity (e.g., staurosporine), e.g., in solution. A composition comprising the kinase or ATPase inhibitor may comprise more than one inhibitor. The kit may supply one or more isolated ADP to ATP converting enzymes and optionally substrates therefore, which are phosphate group donors (e.g., phosphocreatine, phosphoenolpyruvate or polyphosphate), or other isolated enzymes, such as isolated adenylate cyclases, or pyrophosphatase.

In one embodiment, the kit comprises a container comprising a buffered solution, e.g., about pH 6.0 to about pH 8.0, having isolated adenylate cyclase, optionally one or more kinase or ATPase inhibitors, and optionally a pyrophosphatase. The kit may additionally comprise a separate container comprising lyophilized luciferase, or optionally comprise a separate container comprising an inhibitor of adenylate cyclase, a kinase and optionally a substrate for the ADP to ATP converting enzyme. In one embodiment, the container comprising lyophilized luciferase further comprises lyophilized luciferin or a derivative thereof that is a luciferase substrate. Optionally, the kit further comprises instructions for use of the kit for the purpose of measuring ADP.

BRIEF DESCRIPTION OF THE FIGURES

FIGS. 33A-33H provide exemplary sequences for adenylate cyclases (SEQ ID NOs: 1-9; NCBI Accession Nos. Y00545, M24074, YP016473, NP652900, AP003604, AA01202, P15318 and Q57506), and ADP to ATP converting enzymes (SEQ ID NOs: 10-15; NP_067248, NP_031736, AAC31758, AAF06820 and NP_077352).

DETAILED DESCRIPTION OF THE INVENTION

Definitions

Figure 1:
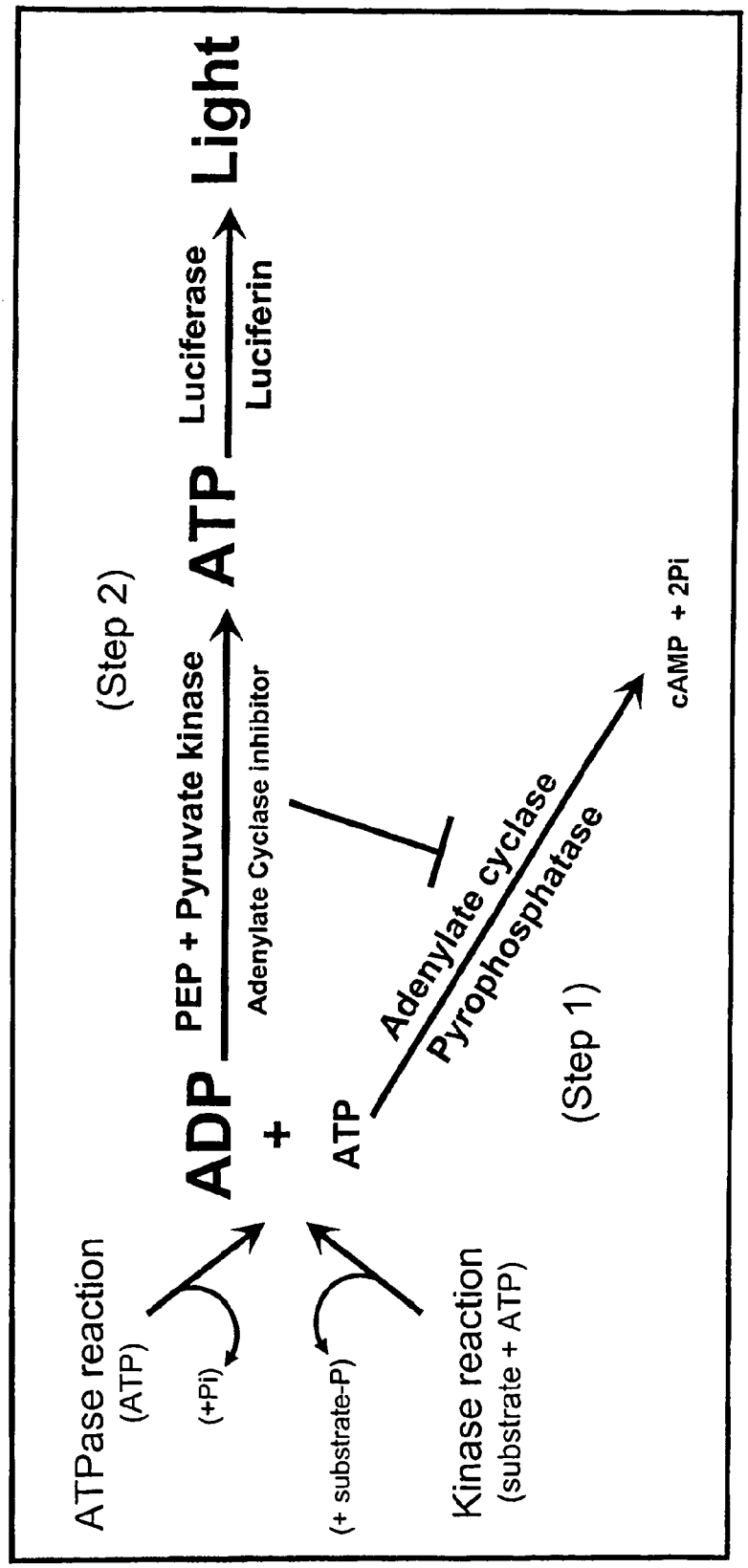
FIG. 1 is a scheme of the ADP detection assay where adenylate cyclase (AC) is used prior to the detection step to remove the ATP remaining after the ADP-forming reaction.

Unless defined otherwise, all technical and scientific terms have the same meaning as is commonly understood by one of skill in the art to which this invention belongs. All cited patents and publications are incorporated by reference in their entirety unless otherwise noted.

An "isolated" or "purified" enzyme such as an adenylate cyclase, kinase, ATPase or luciferase is one that has been identified and separated and/or recovered from a component of its natural environment.

The term "sample" as used herein, is used in its broadest sense. A sample is a composition suspected of kinase or ATPase activity that is analyzed using the invention. While often a sample is known to contain or suspected of containing kinase or ATPase activity, optionally in a growth media, or a cell lysate, a sample may also be a solid surface (e.g., a swab, membrane, filter, particle) suspected of containing kinase or ATPase activity. It is contemplated that for such a solid sample, an aqueous sample is made by adding the solid to the reagent composition of the invention or to another aqueous solution to which the reagent composition of the invention is added.

The term "detection," as used herein, refers to quantitatively or qualitatively determining the presence or absence of a component within the sample.

"Percent (%) amino acid sequence identity" is defined as the percentage of amino acid residues in one sequence that are identical to, with, or against amino acid residues in a second sequence in the region of overlap when the two sequences are optimally aligned. To determine percent amino acid identity, sequences are locally aligned and if necessary, gaps are introduced to achieve the maximum percent sequence identity; conservative substitutions are not counted when calculating sequence identity. Amino acid sequence alignment procedures to determine percent identity are well known to those of skill in the art. Publicly available computer software such as BLAST software (NCBI at www.ncbi.nlm.nih.gov/BLAST/) may be used to align peptide sequences. Those skilled in the art can determine appropriate algorithms and parameters for measuring alignment, including any algorithms and parameters needed to achieve optimal alignment of two amino acid sequences.

When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as:

$$\% \text{ amino acid sequence identity} = (X/Y) \cdot 100$$

where X is the number of amino acid residues scored as identical matches in the optimal alignment of A and B by the sequence alignment program or algorithm and Y is the total number of amino acid positions aligned.

The term "luminescent", as used herein, includes bio-luminescence (i.e., light produced by a living organism), chemiluminescence (light produced when a chemical reaction proceeds), and electrochemical-luminescence. When the enzyme involved has evolved in an organism by natural selection for the purpose of generating light, or the enzyme involved is a mutated derivative of such an enzyme, the luminescent reactions are also called "bioluminescent reactions" and the enzyme involved is also called a "bioluminescent enzyme." Examples of bioluminescent enzymes include, without limitation, firefly luciferase, *Renilla* luciferase, *Cypridina* luciferase, *Aequorin* photoprotein, *Gaussia* luciferase, *Oplophorus* luciferase, *Obelin* photoprotein, and the like.

The term "luminogenic molecule" as used herein refers to a molecule capable of creating light via a chemical or biochemical reaction (e.g., luciferin, coelenterazine, or a functional analog thereof). Suitable luminogenic molecules or substrates for luciferase enzymes include luciferins, coelenterazines and functional analogs of luciferins and coelenterazines. In some embodiments, functional analogs of luciferins and coelenterazines include modified luciferins and coelenterazines, including derivatives of these compounds. Exemplary compounds include those disclosed in WO 03/040100, WO 2004/027378 and US published application 2009-0075309.

Generally, a luminogenic molecule is either a high energy molecular species (e.g., a stabilized dioxetane), or it is transformed into a high energy molecular species by a chemical reaction. The chemical reaction is usually oxidation by oxygen, superoxide, or peroxide. In each case, the energy within the luminogenic molecule is released by the chemical reaction. Although at least some of this energy is released as photons of light, the energy can also be released in other forms, such as heat. The luminogenic molecules that do not yield light disperse their energy through alternative modes, often termed "dark pathways".

The term "luciferin derivative" as used herein refers to a type of luminogenic molecule or compound having a substantial structure of D-luciferin and is a luciferase substrate, e.g., aminoluciferin, or luciferase substrates disclosed in U.S. application Ser. No. 11/444,145, Branchini et al. (1989), e.g., naphthyl and quinolyl derivatives, Branchini et al. (2002), and Branchini (2000), the disclosures of which are incorporated by reference herein.

The term "inhibitor" refers to a molecule, compound, or substance that is capable of substantially reducing or stopping enzyme activity in a sample by any mechanism including, without limitation, direct or indirect inactivation, inhibition, denaturation, or sequestering.

As used herein the phrase "reducing substantially all ATP in the solution to a non ADP substrate" means that the amount of ATP in solution is reduced to an amount that allows for detecting the presence or absence of or determining the amount of the ATP produced from ADP in the solution. In some embodiments, the amount of ATP in the solution is reduced to less than 2%, for example 1%, 0.75%, 0.5%. 0.25%, 0.1%, 0.075%, 0.05%. 0.025%, 0.02%, 0.01%, 0.001%, or 0.0001% or less, of the original amount of ATP in the solution.

As used herein the phrase "removing substantially all PPi" means that the amount of PPi in solution is reduced to an amount so that the bioluminescent reaction can detect the presence or absence of or determine the amount of ATP produced from ADP in the solution. In some embodiments, the amount of PPi in the solution is reduced to less than 5%, for example 4%, 3%, 2,%, 1%, 0.75%, 0.5%. 0.25%, 0.1%, 0.075%, 0.05%, 0.025%, 0.02%, 0.01%, 0.001%, or 0.0001% or less, of the original amount of PPi in the solution. In some embodiments, the PPi will be removed using an enzyme such as a pyrophosphatase.

Exemplary Compositions and Methods of the Invention

The present invention provides compositions and methods of using these compositions to measure kinase or ATPase activity in a sample by detecting ADP formation by the kinase or ATPase after inhibiting the kinase or ATPase and converting any remaining ATP to cAMP. The ADP formed is then converted to ATP which is employed in a bioluminescent reaction, for instance, in conjunction with a luciferase-mediated reaction, optionally in a single step, that is then followed by detection of the resulting luminescence. In one embodiment, the luminescence resulting from the use of the compositions of the invention with a sample has an extended duration, i.e., diminished by less than about 50% per hour relative to the luminescence just after the last composition is combined with the sample.

A sample for use in the methods may comprise cells, a cell lysate, a subcellular fraction of a lysate, such as a membrane fraction or an acellular sample, and includes physiological samples. Cells within the scope of the invention include prokaryotic and eukaryotic cells, including plant cells and vertebrate cells, for instance, mammalian cells including, but not limited to, human, non-primate human, bovine, equine, ovine, swine, caprine, feline, canine, mink, rodent or avian cells. A sample comprising cells may be treated so as to permeabilize or lyse the cells in the sample. Methods for permeabilization, lysis or disruption of cells or subcellular fractions thereof are well known in the art. A wide variety of equipment is available for mechanical disruption including sonicators (ultrasonic generators), a dounce, mortar and pestle, or French presses. Cells can be disrupted (yielding cell lysates) by osmotic shock, by treatments such as a series of freeze-thaw cycles or a rapid alteration of the ionic strength of the environment, or by the use of agents that directly disrupt cell membranes such as enzymes like lysozyme or chemical agents such as detergents or surfactants, such as zwitterionic and nonionic detergents, or cationic detergents DTAB or CTAB, and antibacterials such as polymixin B and chlorhexidine.

The cells in a sample, e.g., a sample which includes eukaryotic cells such as yeast, avian, plant, insect or mammalian cells, including but not limited to human, simian, murine, canine, bovine, equine, feline, ovine, caprine or swine cells, prokaryotic cells, cells from two or more different organisms, or cell lysates, may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a kinase or ATPase to be detected by the methods of the invention, a moiety which alters the level or activity of the kinase or ATPase to be detected, and/or a gene product unrelated to the molecule or moiety that alters the level or activity of the kinase or ATPase.

In one embodiment, the present invention reduces to two steps the manipulations needed for measuring kinase or ATPase activity in a sample prior to luminescence measurement. In such a method, at least a portion of the products of a kinase or ATPase reaction is combined with the necessary components for adenylate cyclase and pyrophosphatase reactions where the ATP remaining after the kinase or ATPase reaction is converted to cAMP, and the pyrophosphate is degraded. At least a portion of products of the reaction mixture having cAMP is mixed with all of the necessary components for an ADP to ATP converting enzyme reaction and a bioluminescent reaction, e.g., components including an inhibitor of the adenylate cyclase, one or more ADP to ATP converting enzyme and optionally a substrate therefore, and the ATP-dependent bioluminescence generating enzyme (e.g., luciferase), and a corresponding luminogenic molecule.

In a three-step method, at least a portion of the products of a kinase or ATPase reaction which includes ADP and ATP is mixed with the necessary components for the adenylate cyclase and pyrophosphatase reactions, generating cAMP and phosphate. At least a portion of the products of that reaction is mixed with the necessary components for an ADP to ATP converting enzyme reaction. At least a portion of the products of the ADP to ATP converting enzyme reaction is mixed with the necessary components for an ATP-dependent bioluminescent enzyme-mediated reaction.

Exemplary kinases and ATPases for detection, or for use in screening for modulators of kinases or ATPases, are provided below.

TABLE 1

| enzyme | Substrate |
| --- | --- |
| hexokinase | ATP/hexoses |
| glucokinase | ATP/glucose |
| fructokinase | ATP/fructose |
| galactokinase | ATP/galactose |
| mannokinase | ATP/mannose |
| glucosamine kinase | ATP/2-amino-2-desoxy-D-glucose |
| phosphoglucokinase | ATP/lucose-1-P |
| phosphofructokinase | ATP/fructose-6-P |
| gluconokinase | ATP/D-gluconate |
| Adenosine kinase | ATP/adenosine |
| NAD kinase | ATP/NAD |
| glycerol kinase | ATP/glycerol |
| glycerate kinase | ATP/glycerate |
| choline kinase | ATP/choline |

TABLE 1-continued

| enzyme | Substrate |
| --- | --- |
| pyruvate kinase | ATP/pyruvate |
| glucuronokinase | ATP/glucuronate |
| galacturonokinase | ATP/galacturonate |
| arabinokinase | ATP/arabinose |
| mannitol kinase | ATP/mannitol |
| inosine kinase | ATP/inosine |
| acetate kinase | ATP/acetate |
| carbamate kinase | ATP/$NH_3$/$CO_2$ |
| aspartate kinase | ATP/aspartate |
| carbamoyl phosphate synthase | 2 ATP/$NH_3$/$CO_2$/$H_2O$ |
| formate kinase | ATP/fromate |
| carbamoyl phosphate synthase | 2 ATP/glutamine/$CO_2$/$H_2O$ |
| guanidinoacetate kinase | ATP/guanidine acetate |
| creatine kinase | ATP/creatine |
| arginine kinase | ATP/L-arginine |
| ammonia kinase | ATP/$NH_3$ |
| polyphosphate kinase | ATP (phosphate)n |
| adenylate kinase | ATP/AMP |
| nucleoside monophosphate kinase | ATP/nucleoside monophosphate |
| nucleoside diphosphate kinase | ATP/nucleoside diphosphate |
| guanylate kinase | ATP/GMP |
| cytidylate kinase | ATP/CMP |
| succinyl-CoA-synthetase | ATP/succinate/CoA |
| glutaryl-CoA-synthetase | ATP/glutarate/CoA |
| Malyl-CoA-synthetase | ATP/malate/CoA |
| glutamine synthetase | ATP/glutamate/$NH_3$ |
| asparagine synthetase | ATP/aspartate/$NH_3$ |
| γ-glutamyl-cysteine synthetase | ATP/glutamate/cysteine |
| glutathione synthetase | ATP/γ-glutamyl-cysteine/glycine |
| D-alanylalanine synthetase | ATP/2 D-alanine |
| urea carboxylase | ATP/urea/$CO_2$ |
| pyruvate carboxylase | ATP/pyruvate/$H_2O$/$CO_2$ |
| 5'-nucleosidase | ATP/ASN/$NH_3$/glutamate |
| adenosine desaminase | ATP/ASN/ISN/NH3/glutamate |

In one embodiment, kinases to be detected, or used in assays to detect modulators thereof include, but are not limited to ABL1, ABL2/ARG, AKT1, AKT2, AKT3, ALK, ALK4, ALK5, TGFBR1, ARAF, ARK5, ASK1, Aurora A, Aurora B, Aurora C, AXL, BLK, BMX, BRAF, BRK, BRSK1, BRSK2, BTK, CAMK1a alpha, CAMK1d, CAMKIIa alpha, CAMKIIb beta, CAMKIId delta, CAMKIIg gamma, CAMK4, CAMKK2, CDK1/cyclinB, CDK2/cyclinA, CDK2/cyclinE, CDK3/cyclinE, CDK4-cyclinD1, CDK5/p25, CDK5/p35, CDK6/cyclinD1, CDK6/cyclinD3, CDK7/cyclin H/MNAT1, CDK9/CyclinK, CDK9/CyclinT1, CHK1, CHK2, CK1 (Yeast), CK1d (Rat), CK1a1 alpha, CK1d, CK1e, CK1g1/CSNK1G1, CK1g2, CK1g3/CSNK1G3, CK2 alpha, CK2a2, c-KIT, CLK1 CD, CLK3, c-MER, c-MET, COT1/MAP3K8, CSK, c-SRC, CTK/MATK/HYL, DAPK1, DAPK2, DCAMKL2, DDR2, DMPK, DNA-PK, DRAK1, DYRK1/DYRK1A, DYRK1B, DYRK2, DYRK3, DYRK4, EEF2K, EGFR, EPHA1, EPHA2, EPHA3, EPHA4, EPHA5, EPHA7, EPHA8, EPHB1, EPHB2, EPHB3, EPHB4, ErbB2/HER2, ErbB4/HER4, ERK1, FAK, FER, FES/FPS, FGFR1, FGFR2, FGFR3, FGFR4, FGR, FLT1/VEGFR-1, FLT3, FLT4, FMS, FRK_PTK5, FYN, GCK/MAP4K2, GRK2, GRK3, GRK4, GRK5, GRK6, GRK7, GSK3a, GSK3B, HCK, HGK/MAP4K4, HIPK1, HIPK2, HIPK3, HIPK4, IGF1R, IKK alpha, IKK beta, IR, IRAK1, IRAK4, IRR, ITK, JAK1, JAK3, JNK1 alpha 1, JNK2 alpha 2, JNK3, KDR/VEGFR-2, LCK, LKB1 (STK11), LIMK1, LOK/STK10, LYN, MAPKAPK2, MAPKAPK3, MAPKAPK5/PRAK, MARK1, MARK2, MARK3, MEK1, MELK, MINK, MLCK/MYLK, MLCK2/MYLK2, MLK1, MNK2, MRCKA/CDC42BPA, MRCKB/CDC42BPB, MSK1, MSK2, MSSK1/STK23, MST1, MST2, MST3/STK24, MST4, mTOR, MUSK, NEK1, NEK2, NEK3, NEK4, NEK6, NEK9, NEK11, NIK MAP3K14, NLK, P38 alpha, P38 beta, P38 delta, P38 gamma, P70s6k, PAK1, PAK2, PAK3, PAK4, PAK5, PAK6, PASK, PBK/TOPK, PDGFR alpha, PDGFR beta, PDPK1, PHK gamma2, P13Ka (p110a/p85a), P13Kb (p110b/p85a), (p110d/p85a), P13Kg (p120g), PIM1, PIM2, PKA, PKC alpha, PKC beta1, PKC beta2, PKC delta, PKC epsilon, PKC eta, PKC GAMMA, PKCiota, PKCmu, PKCtheta, PKCzeta (PKCz), PKD2, PKG1 alpha, PCG1 beta, PKG2/PRKG2, PKN2/PRK2, PLK1, PLK2, PLK3, PRKD3/PKCnu, PRKX, PYK2, RAF1, RET, RIPK2, ROCK1, ROCK2, RON, ROS, RSK1, RSK2, RSK3, RSK4/RPS6KA6, SGK1, SGK2, SGK3/SGKL, SIK2/SNF1LK2, STK22D, STK33, SRPK1, SRPK2, SYK, TAK1, TAOK2/TAO1, TAOK3/JIK, TBK1, TEC, TIE2, TRKA, TRKB, TRKC, TSSK2, TTK, TYK1/LTK, TYK2, TYRO3_SKY, VRK1, WEE1, WNK2, WNK3, YES, ZAK/MLTK, ZAP70, and ZIPK/DAPK3.

For instance, exemplary kinase/substrate combinations for use in the methods of the invention include JNK-1/c-jun, JNK-2/c-jun, MAP Kinase-1 (ERK-1)/myelin basic protein, MAP Kinase-2 (ERK-2)/myelin basic protein, PKA/Kemptide, MEK-1/inactive MAP Kinase-2 (ERK-2), JNK2α2/ATF-2, JNK2α2/c-jun, SAPK-3/myelin basic protein, SAPK-4/myelin basic protein and ref-1/inactive MEK-1.

Exemplary ATPases for detection or for use in screening methods include but are not limited to F-ATPases (F1F0-ATPases), V-ATPases (V1V0-ATPases), A-ATPases (A1A0-ATPases), P-ATPases (E1E2-ATPases), and E-ATPases. Exemplary human ATPases are Na+/K+ transporting enzymes such as those encoded by: ATP1A1, ATP1A2, ATP1A3, ATP1A4, ATP1B1, ATP1B2, ATP1B3, or ATP1B4; Ca++ transporting enzymes such as those encoded by: ATP2A1, ATP2A2, ATP2A3, ATP2B1, ATP2B2, ATP2B3, ATP2B4, or ATP2C1; Mg++ transporting enzymes such as those encoded by: ATP3; H+/K+ exchanging enzymes such as those encoded by: ATP4A, or ATP4B; H+ transporting, mitochondrial enzymes such as those encoded by: ATP5A1, ATP5B, ATP5C1, ATP5C2, ATP5D, ATP5E, ATP5F1, ATP5G1, ATP5G2, ATP5G3, ATP5H, ATP5I, ATP5J, ATP5J2, ATP5L, ATP5L2, ATP5O, or ATPATP5S; H+ transporting, lysosomal enzymes such as those encoded by: ATP6AP1, ATP6AP2, ATP6V1A, ATP6V1B1, ATP6V1B2, ATP6V1C1, ATP6V1C2, ATP6V1D, ATP6V1E1, ATP6V1E2, ATP6V1F, ATP6V1G1, ATP6V1G2, ATP6V1G3, ATP6V1H, ATP6V0A1, ATP6V0A2, ATP6V0A4, ATP6V0B, ATP6V0C, ATP6V0D1, ATP6V0D2, or ATP6V0E; Cu++ transporting enzymes such as those encoded by: ATP7A or ATP7B; Class 1, type 8 enzymes such as those encoded by: ATP8A1, ATP8B1, ATP8B2, ATP8B3, or ATP8B4; Class II, type 9 enzymes such as those encoded by: ATP9A or ATP9B; Class V, type 10 enzymes such as those encoded by: ATP10A, ATP10B, or ATP10D; Class IV, type 11 enzymes such as those encoded by: ATP11A, ATP11B, or ATP11C; H+/K+ transporting, non-gastric enzymes such as those encoded by: ATP12A; and type 13 enzymes such as those encoded by: ATP13A1, ATP13A2, ATP13A3, ATP13A4, or ATP13A5.

For instance, any heat shock protein with ATPase activity, e.g., HSP70 or HSP90, may be detected or used in the methods of the invention. Inhibition of HSP90 ATPase activity results in degradation of the protein and its client kinases. Thus, developing inhibitors for HSP90 is an active area of research in the pharmaceutical industry.

In one embodiment of the method of detecting kinase activity comprises contacting a sample suspected of having a kinase with a kinase substrate, and ATP for a first predetermined time period to allow for sufficient opportunity for the kinase to interact with the kinase substrate. The method can be used with a wide variety of substrates such as amino acids, peptides, proteins (including fusion proteins and other kinases), sugars and lipids. The resulting kinase reaction mixture is then contacted with a second composition for a second predetermined time period. The second composition comprises an activated adenylate cyclase and a pyrophosphatase, and optionally a kinase inhibitor. The resulting second reaction mixture is then contacted with a third composition comprising an ADP to ATP converting enzyme, a bioluminescence generating enzyme, a luminogenic molecule, and optionally an adenylate cyclase inhibitor and/or a substrate for the ADP to ATP converting enzyme. Thereafter, the bioluminescence produced in the resulting third reaction mixture is detected. The bioluminescence is produced by the conversion of the luminogenic molecule into a luminescent compound by a bioluminescence generating enzyme such as luciferase. This method can be used to measure a distinct end-point of a kinase or ATPase reaction. In one embodiment, a reagent composition allows for the simultaneous inhibition of adenylate cyclase activity and generation of a luminescent signal that is directly proportional to the amount of ADP present.

The luminescence generated by a luciferase reaction is typically detected with a luminometer although other detection means may be used. The presence of light greater than background level indicates the presence of ATP in the sample. The background level of luminescence is typically measured in the same matrix, but in the absence of the sample. Suitable control reactions are readily designed by one of skill in the art. Luciferases may allow for multiple analyses of a sample over time or analysis of many samples over time. Optionally, the luciferases used in the compositions and methods of the invention have enhanced thermostability properties.

Quantifying the amount of emitted light also quantifies the amount of ATP and thus the amount of ADP produced by the kinase or ATPase in a sample. Thus, quantitation of ATP allows for quantitation of kinase or ATPase activity. Quantitative ATP values are realized, for example, when the quantity of light emitted from a test sample, in which ADP is converted to ATP via the methods of the invention which monitor ADP formation by converting it to ATP, is compared to the quantity of light emitted from a control sample or to a standard curve determined by using known amounts of ATP and the same luciferase and reaction conditions (i.e., temperature, pH, etc.). It is understood that quantification involves subtraction of background values. Qualitative ATP values are realized when the luminescence emitted from one sample is compared to the luminescence emitted from another sample without a need to know the absolute amount of ATP converted from ADP present in the samples, e.g., a comparison of samples in the presence or absence of a test agent. Many such experiments can readily be designed by one of ordinary skill in the art.

Any inhibitor of a kinase or ATPase, or a combination of inhibitors, may be employed in an amount sufficient to inhibit kinase or ATPase activity in the reaction mixture with the sample by at least about 5%, e.g., at least about 10%, 20%, 30%, 40%, 50%, 60%, 70%, 80%, 90%, 95%, 99% or more or any increment therein, relative to a corresponding reaction without the inhibitor(s). ATPase inhibitors include but are not limited to local anesthetics, chondropsin, nicotinamide derivative, bafilomycin, indole-clase, archazolid, apicularen, macrocyclic carbon suboxide factors, substituted thieno[3,4-d]imidazoles, and geldanamycin and derivatives thereof. For instance, geldanamycin is an inhibitor of HSP90 although derivatives of geldanamycin such as a derivative of 17-allylamino-geldanamycin (17-AAG) have better solubility, oral delivery, potent activity and pharmacokinetic properties.

Exemplary kinase inhibitors include but are not limited to AMP, DAPP, dichloroacetic acid, staurosporine, UCN-01, and calphostin C, 4-anilino-3-quinolmecarbonitriles, AC220, heterocyclic ureas, NaF, detergents with charged groups such as cationic detergents (e.g., DTAB (dodecyltrimethylammonium bromide), CTAB (cetyltrimethylammonium) and BDDABr (benzyldimethyldodecylammonium bromide)), anionic detergents (e.g., SDS and deoxycholate), zwitterionic detergents (e.g., sulfobetaine 3-10), imidazole derivatives, AMG706, zactima, MP-412, BAY 43-9006, CEP-701 (lestaurtinib), XL647, XL999, MLN518 (formerly known as CT53518), PKC412, ST1571, AMN107, AEE 788, OSI-930, OSI-817, SU11248, and AG-013736. Other inhibitors useful to inhibit a kinase or ATPase include but are not limited to SU11248, sorafenib, zactima, lapatinib, imatinib, gefitinib, sunitinib, erlotinib, nilotinib, lapatinib, STI571, dasatinib, staurosporine, Ro31-8220, GW5074, H-89, wortmannin, quercetin, LY294002, glucose 6-phosphate (for hexokinase), or D-erythro-N,N-dimethylsphingosine (for sphingosine kinase).

Exemplary adenylate cyclases include but are not limited to those from *Vibrio cholerae*, e.g., cya, *Bacillus anthracis*, or *Bortedella pertussis*, e.g., pertussis toxin. The calmodulin-dependent fraction of adenylate cyclases can be inhibited by phenothiazines and butyrophenones (Levin & Weiss, 1976; Gietzen et al., 1980), naphthalene sulphonamides (Kobayashi et al., 1979), Vinca alkaloids (Watanabe et al., 1979; Gietzen & Bader, 1980), local anaesthetics (Volpi et al., 1981), calmidazolium (Gietzen et al., 1981), formerly referred to as R 24571, and compound 48/80 (Gietzen et al., 1983) (see also Wolff & Brostrom (1976) and Gietzen et al. (1982a)). Generally, activators of calmodulin-dependent enzymes (calmodulin, oleic acid or phosphatidyl-serine) can be considered as anionic amphiphiles, whereas calmodulin antagonists are cationic amphiphiles at physiological pH. Calmodulin-stimulation of an enzyme may occur by calmodulin forming a complex with the cationic amphiphilic antagonist, as a result of their complementary structural features, via ionic and hydrophobic interactions (Weiss et al., 1980), and in addition, several calmodulin antagonists exert their inhibitory effect via direct interaction with the calmodulin effector enzyme (Gietzen et al., 1982a,b). Moreover, almost all described inhibitors are more or less unspecific in that they also inhibit the basal activity of calmodulin-dependent enzymes.

Exemplary adenylate cyclase activators include but are not limited to calmodulin, adenosine, or carbacyclin.

Exemplary adenylate cyclase inhibitors include but are not limited to calmodulin antagonists such as calmidazolium, $N^6$-cyclo hexyl adenosine, adenosine, 2',5'dideoxyadenosine, $E_6$ berbamine, trifluoroperazine, compound 48/80, MDL-12, 330A, SQ 22536, 9-cyclopentyladenine, pyrocatechol, 2',5'-dideoxyadenosine 3'-monophosphate, 2',5'-dideoxyadenosine 3'-diphosphate, 2',5'-dideoxyadenosine 3'-triphosphate, 2',5'-dideoxyadenosine, or 2'/3'-O—(N-methylanthraniloyl) guanosine-5'-(γ-thio)triphosphate triethylammonium salt.

The compositions of the invention that contain one or more enzymes may also comprise an enzyme stabilizing agent. The enzyme stabilizing agent can be any compound that stabilizes the enzyme, e.g., from degradation. Suitable enzyme stabilizing agents include proteins (such as bovine serum albumin, gelatin or Prionex®) or detergents (such as non-ionic detergents, e.g., THESIT).

Further, the present invention is useful for determining the effect of small molecules (including organic and inorganic molecules and synthetic and naturally occurring molecules)

on kinase or ATPase activity, which in turn allows the assessment of whether the small molecule may function as a pharmaceutical drug. The methods may include controls in which samples are contacted with control substances whose effects on kinase or ATPase activity are known. Also, controls may include samples in which the adenylate cyclase, ADP to ATP converting enzyme or ATP-dependent bioluminescent enzyme and the test agent(s) are present together to assure that the agent(s) do not directly affect adenylate cyclase, ADP to ATP converting enzyme and ATP-dependent bioluminescent enzyme activity.

Those skilled in the art recognize that the methods compositions and kits described herein can be used to measure the activity of enzymes that convert ATP to ADP, such as kinases or ATP hydrolases. Additionally, the described methods can be used to determine how much the enzyme is inhibited by a known or putative inhibitor, particularly when the results of such a reaction are compared against one or more standards or control reactions. Accordingly, the present methods, compositions and kits can be used to identify inhibitors of enzymes.

Thus, the invention is directed to methods that determine the effect of one or more test agents on a first sample containing kinase or ATPase enzyme by contacting the first sample with a concentration of one or more test agents and then at a later time contacting the first sample with a reagent composition of the invention, detecting and comparing the amount of luminescence in the first sample to an amount of luminescence in a second sample containing kinase or ATPase. The second sample may be contacted with a concentration of one or more test agents that is less than the concentration contacting the first sample or may or may not contain the one or more test agents. A lesser amount of luminescence detected from the first sample compared to the second sample may indicate that the one or more test agents comprise an inhibitory agent. In this way, inhibitory reagents may be discovered. Similarly, the invention is useful for discovering kinase or ATPase activity enhancing reagents. Using the above example, a lesser amount of luminescence detected from the second sample compared to the first sample may indicate that the one or more test agents comprise a kinase or ATPase enhancement agent. The invention is useful for comparing the effects of different test agents at the same concentration on kinase or ATPase activity. The invention is also useful for comparing the effect of one or more test agents on different types of kinase or ATPase. One of skill in the art may develop many other such assays for which the invention is useful.

In one embodiment, the invention provides a method for screening one or more test agents for their effect on kinase or ATPase activity. The method includes providing one or more test agents for screening and incubating a first reaction mixture comprising one or more kinases or ATPases, ATP, and the one or more test agents for a first predetermined time period under conditions effective to allow for conversion of ATP to ADP by the one or more kinases or ATPases. The first reaction mixture is then contacted with a first reagent having an amount of an isolated active adenylate cyclase and a pyrophosphatase, and optionally an amount of one or more inhibitors of the kinases or ATPases, to form a second reaction mixture which is incubated for a second predetermined time period under conditions effective to allow for conversion of ATP to cAMP. The second reaction mixture is contacted with a second reagent to yield a third reaction mixture, wherein the second reagent includes one or more inhibitors of the adenylate cyclase, one or more ADP to ATP converting enzymes, a luminogenic molecule and a bioluminescence generating enzyme for a third predetermined time period under conditions effective to allow for a bioluminescent reaction. Then, the effect of the one or more test agents on kinase or ATPase activity is determined by measuring and comparing luminescence of the third reaction mixture relative to a control mixture without the test agent(s). In one embodiment, the effect of the one more tests agents on kinase activity is determined, e.g., protein kinase activity, lipid kinase activity, polynucleotide kinase activity, or sugar kinase activity. In one embodiment, the luminogenic molecule comprises D-luciferin or a luciferin derivative, and the bioluminescent enzyme comprises a luciferase.

In one embodiment, the reaction mixture for a kinase or ATPase reaction under optimal enzyme reaction conditions includes a test agent, e.g., one that may inhibit the kinase or ATPase. A buffer containing an active adenylate cyclase, e.g., from *B. pertussis*, is added to the reaction mixture to convert the remaining ATP into cAMP and pyrophosphate. Optionally, the buffer may contain an inhibitor of the kinase or ATPase to terminate the kinase or ATPase reaction. Also optionally, the buffer may contain a pyrophosphatase. In one embodiment, pyrophosphatase is present in the solution for the reaction that converts ATP to cAMP, and the bioluminescence generating enzyme is luciferase. In such a reaction, the light generated from the luciferase reaction is unaffected since pyrophosphate is a known inhibitor of luciferase. ADP formed in the kinase or ATPase reactions is converted to ATP using an ADP to ATP converting enzyme such as adenylate kinase, creatine kinase, pyruvate kinase, and the like. To prevent the adenylate cyclase from using the newly formed ATP, the ADP to ATP converting reaction is performed in the presence of an adenylate cyclase inhibitor, e.g., a calmodulin antagonist. Optionally, the ADP to ATP converting reaction may contain a substrate for the ADP to ATP converting enzyme, such as a substrate for adenylate kinase, creatine kinase or pyruvate kinase. The ATP formed is measured by the addition of reagents for an ATP dependent bioluminescent enzyme mediated reaction (e.g., a luciferase/luciferin reaction). The RLU generated is proportional to the ADP concentration produced in the kinase or ATPase reaction, and thereby is a measure of those enzyme activities.

One composition of the present invention comprises one or more adenylate cyclase inhibitors, e.g., one or more detergents such as those disclosed in U.S. publication number 2004/0101922, and one or more ADP to ATP converting enzymes, which optionally includes a substrate(s) for the ADP to ATP converting enzymes and also optionally a non-endogenous ATP-dependent bioluminescence generating enzyme and a substrate therefore. The composition is capable of maintaining at least about 30% enzymatic activity for at least about one hour, e.g., for at least about 2 hours up to about 4 hours. In one embodiment, the non-endogenous ATP-dependent enzymes are luciferases.

Luciferase enzymes produce catalytic products that provide a detectable light product, sensitivity, and allow easy measurement of ATP. However, any bioluminescence generating-enzyme that is ATP-dependent may be used in the methods and compositions of the present invention.

At their most basic level, luciferases are defined by their ability to produce luminescence. More specifically, a luciferase is an enzyme that catalyzes the oxidation of a substrate, luciferin, to produce oxiluciferin and photons.

To date, five classes of luciferases have been identified. Of these, beetle luciferases, such as that of the common firefly (family Lampyridae), form a distinct class with unique evolutionary origins. Beetle luciferases are often referred to as firefly luciferases in the literature; however, firefly luciferases are actually a subgroup of the beetle luciferase class. Beetle luciferases may be purified from the lanterns of the beetles themselves or from protein expression systems well known in the art.

Beetle luciferases, particularly firefly luciferase from the North American firefly *Photinus pyralis*, are well known in the art. The *P. pyralis* luciferase (LucPpy) consists of approximately 550 amino acids of $M_r$ 61 kDa as calculated by the protein encoded by the nucleotide sequence of the gene. However, other firefly luciferases are known, such as *Photuris pennsylvanica* firely luciferase (LucPpe2; 545 amino acid residues; GenBank 2190534). Mutant luciferases derived from LucPpe2 (e.g., LucPpe2m78 (also known as 78-0B10); LucPpe2m90 (also known as 90-1B5); LucPpe2m133 (also known as 133-1B2); LucPpe2m146 (also known as 146-1H2) may be employed, however, any luciferase that meets the limitations set forth herein may be used in the composition, method and kits of the invention. The method of making mutant luciferases from LucPpe is disclosed in PCT/US99/30925.

Isolated and/or purified luciferases are typically used in the present invention. Luciferases that may be used in the methods, compositions and kits described herein include those found in WO 1999/14336, WO 2001/20002, WO 2004/027378, EP 1 124 944, EP 1 224 294, U.S. Pat. Nos. 5,837,465, 6,171,808, 6,132,983, and 6,265,177.

Luciferases can be isolated from biological specimens that produce luciferase or from a cell that expresses an exogenous polynucleotide encoding a desired luciferase. Such techniques are well known to those of skill in the art (see U.S. Pat. No. 6,602,677).

The naturally-occurring substrate for beetle luciferases is firefly luciferin, a polytherocyclic organic acid, D-(−)-2-(6'-hydroxy-2'-benzoth-iazolyl)-$\Delta^2$-thiazolin-4-carboxylic acid (luciferin). Luciferin may be isolated from nature (e.g., from fireflies) or synthesized. Synthetic luciferin can have the same structure as the naturally occurring luciferin or can be derivatized, so long as it functions analogously. Examples of derivatives of luciferin include D-luciferin methyl ester and other esters of luciferase that are hydrolyzed or acted upon by esterases in a sample to yield luciferin, and naphthyl- and quinolyl-luciferin (Branchini et al., 1989). There are multiple commercial sources for luciferin (e.g., Promega Corp. Madison, Wis.; Molecular Probes, Eugene, Oreg.).

The beetle luciferase-catalyzed reaction that yields luminescence (the luciferase-luciferin reaction) involves firefly luciferin, adenosine triphosphate (ATP), magnesium, and molecular oxygen. In the initial reaction, the firefly luciferin and ATP react to form luciferyl adenylate with the elimination of inorganic pyrophosphate. The luciferyl adenylate remains tightly bound to the catalytic site of luciferase. When this form of the enzyme is exposed to molecular oxygen, the enzyme-bound luciferyl adenylate is oxidized to yield oxyluciferin in an electronically excited state. The excited oxidized luciferin emits light on returning to the ground state:

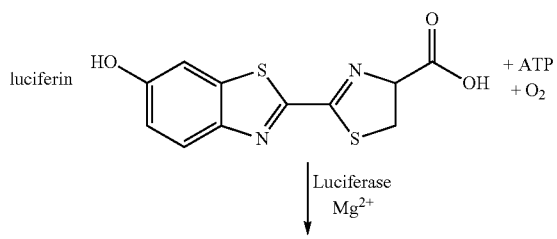

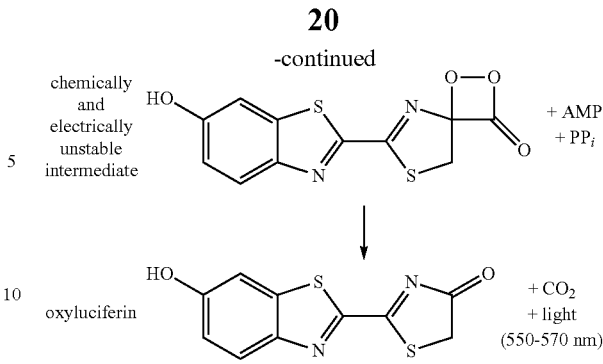

It is contemplated that the ATP function of the reaction can be performed by an ATP analogue (e.g., dATP). It is also contemplated that other ions can serve as substitutes for magnesium ions (e.g., $Mn^{2+}$ or $Ca^{2+}$). Additionally, oxygen is a reactant of the reaction. Therefore, the reaction should not be conducted under anaerobic conditions. However, it is not generally necessary in practicing the invention to provide oxygen over and above that present in the air. Reactions can take place in closed vessels, provided there is sufficient oxygen in the reaction solution.

Most luciferase-luciferin reactions generate a flash of light that is short lived. However, some of the luciferases for use with the invention, e.g., mutants of LucPpe2 such as LucPpe2m146 and LucPpe2m90 luciferases, under the conditions of the invention generate a "glow-type" luminescent signal with less than 50% loss of luminescence per hour after the reagent composition is combined with the sample.

Any luciferase that retains the ability to generate luminescence when used in a reagent composition of the present invention can be used in the present invention.

As is understood by those skilled in the art, all enzyme reactions described herein, including in the claims, expressly or inherently include all enzymes, substrates and conditions necessary for the enzymatic reaction to occur, unless specifically stated otherwise.

Variant Enzymes

A full length luciferase, phosphotransferase such as a kinase or ATP hydrolase such as an ATPase, adenylate cyclase or ADP to ATP converting enzyme variant will have at least about 80% amino acid sequence identity, at least about 81% amino acid sequence identity, such as at least about 82%, 83%, 84%, 85%, 86%, 87%, 88%, 89%, 90%, 91%, 92%, 93%, 94%, 95%, 96%, 97%, 98%, or 99% amino acid sequence identity with a corresponding full-length native luciferase, phosphotransferase or ATP hydrolase, adenylate cyclase, e.g., one having at least 90% amino acid sequence identity to Accession No. Y00545 or M24074, or ADP to ATP converting enzyme sequence and retain the ability to generate luminescence, transfer phosphate groups, form cAMP from ATP or form ATP from ADP, respectively. Ordinarily, variant fragments are at least about 50 amino acids in length, often at least about 60 amino acids in length, more often at least about 70, 80, 90, 100, 150, 200, 300, 400, 500 or 550 amino acids in length, or more and retain the ability to generate luminescence, transfer phosphate groups, form cAMP from ATP or form ATP from ADP. A full length luciferase, phosphotransferase ATP hydrolase, adenylate cyclase or ADP to ATP converting enzyme, fragment thereof, or variant thereof may be fused to heterologous amino acid sequences and still be functional in the invention.

For example, full length beetle luciferase, kinase, ATPase, adenylate cyclase or ADP to ATP converting enzyme, fragments thereof or variants thereof used in the compositions and methods of the present invention may be purified from a native source or prepared by a number of techniques, including (1) chemical synthesis, (2) enzymatic (protease) digestion of luciferase, and (3) recombinant DNA methods. Chemical synthesis methods are well known in the art, as are methods that employ proteases to cleave specific sites. To produce the enzymes, variant enzymes or fragments thereof, DNA encoding the enzymes, variants and fragments can be prepared and then expressed in a host organism, such as E. coli. Methods such as endonuclease digestion or polymerase chain reaction (PCR) allow one of skill in the art to generate an unlimited supply of well-defined fragments. The activity of a variant or fragment may vary from that of the native enzyme.

Any type of amino acid substitution, insertion or deletion, or combination thereof may be used to generate a variant luciferase, adenylate cyclase, kinase, ATPase or ADP to ATP converting enzyme. However, a luciferase, adenylate cyclase, kinase, ATPase, or ADP converting enzyme with a conservative amino acid substitution is more likely to retain activity. Useful conservative substitutions are shown in Table A "Exemplary substitutions." Conservative substitutions whereby an amino acid of one class is replaced with another amino acid of the same type fall within the scope of the invention if the substitution does not impair enzyme activity.

TABLE A

| Original residue | Exemplary substitutions | Preferred substitutions |
| --- | --- | --- |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that effect (1) the structure of the polypeptide backbone, such as a β-sheet or α-helical conformation, (2) the charge or (3) hydrophobicity, or (4) the bulk of the side chain of the target site might modify luciferase function. Residues are divided into groups based on common side-chain properties as denoted in Table B. Non-conservative substitutions entail exchanging a member of one of these classes for another class.

TABLE B

| Amino acid classes | |
| --- | --- |
| Class | Amino acids |
| Hydrophobic | Norleucine, Met, Ala, Val, Leu, Ile |
| neutral hydrophilic | Cys, Ser, Thr |
| Acidic | Asp, Glu |
| Basic | Asn, Gln, His, Lys, Arg |
| Disrupt chain conformation | Gly, Pro |
| Aromatic | Trp, Tyr, Phe |

Variant luciferase, adenylate cyclase, kinase, ATPase, or ADP converting enzyme genes or gene fragments can be made using methods known in the art such as oligonucleotide-mediated (site-directed) mutagenesis, alanine scanning, and PCR mutagenesis. Site-directed mutagenesis) cassette mutagenesis, restriction selection mutagenesis, PCR mutagenesis or other known techniques can be performed on the cloned DNA to produce the variant DNA.

Kits

When the invention is supplied as a kit, the different components of the composition may be packaged in separate containers and admixed prior to use, as described herein. Such separate packaging of the components permits long-term storage without loss of enzyme activity. When various parts of the kit are admixed, they form a "reagent composition", which, in one embodiment, has enhanced stability (i.e., a reagent composition is capable of maintaining at least about 30%, more preferably at least about 60% activity for at least one hour, even more preferably at least 70%, 80%, 90%, 95%, 99% or greater activity for at least one hour, such as at least two hours and or for at least four hours relative to the reagent composition's activity when it is first created, i.e., within the first 1 to 5 minutes. Instructional materials may also be enclosed in the kit, as well as materials that may act as standards or controls, depending on the purpose of the kit.

Reagent Compositions

In one embodiment, the following components of a reagent composition of the invention may be supplied as separate parts that are admixed shortly before use: 1) a luciferase, 2) one or more ADP to ATP converting enzymes, 3) optionally an adenylate cyclase inhibitor, 4) optionally a substrate for the ADP to ATP converting enzyme, and 5) a substrate for luciferase. In one embodiment, the following components of a reagent composition may be supplied as separate parts that are admixed shortly before use: 1) one or more ADP to ATP converting enzymes, 2) an adenylate cyclase inhibitor, and 3) optionally a substrate for the ADP to ATP converting enzyme. In one embodiment, the following components of a reagent composition may be supplied as separate parts that are admixed shortly before use: 1) an adenylate cyclase, 2) a pyrophosphatase, 3) optionally one or more kinase or ATPase inhibitors, and 4) optionally an activator of the adenylate cyclase. The luciferase component may further comprise luciferin and in one embodiment, is lyophilized. The luciferase component optionally comprises excipients for lyophilization, protein (luciferase) stabilizer, magnesium (or alternative cation), and a magnesium chelator (or alternative cation chelator). The composition may further comprise a buffer, divalent cation metal chelators, magnesium (or alternative cation), a defoaming agent, and an enzyme stabilizer (e.g., THESIT). Suitable kit components, compositions and buffers that may be used in the described methods can also be obtained commercially. For example, Kinase-Glo®, Kinase-Glo® Plus, or Kinase-Glo® Max buffers and/or Kinase-Glo®, Kinase-Glo® Plus, or Kinase-Glo® Max substrates available from Promega® in Kinase-Glo®, Kinase-Glo® Plus, or Kinase-Glo® Max Luminesecnt Kinase Assay kits may be used as described herein. The kit components, compositions and buffers may also be modified by the addition of suitable components, including enzymes, such as pyruvate kinase, components, such as phosphoenol pyruvate, salts, chelators, etc. The different components may comprise subsets of these parts and may be combined in any way that either facilitates the application of the invention or prolongs storage life.

Other Kit Components

Kits may also include reagents in separate containers that facilitate the execution of a specific test, such as cell viability, cytotoxicity, or cell proliferation. For example, ATP or ADP may be supplied so that standard curves may be determined or to be used as internal controls. Substances that are known to be kinase or ATPase inhibitors or activators may be included for use as a positive control in detection of kinase or ATPase activity or for determining the effects of test agents on kinase or ATPase activity. The kit may supply multiwell plates and/or one or more kinases or ATPases, adenylate cyclases, or ADP to ATP converting enzymes. The kit may optionally include substrates for the kinase or ATPase, buffer, and an activator or inhibitor of the adenylate cyclase.

Containers or Vessels

The reagents included in the kits can be supplied in containers of any sort such that the life of the different components are preserved, and are not adsorbed or altered by the materials of the container. For example, sealed glass ampules may contain lyophilized luciferase or buffer that has been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port such as a bottle having a stopper that can be pierced by a hypodermic injection needle. Other containers may have two compartments that are separated by a readily removable membrane that upon removal permits the components to mix. Removable membranes may be glass, plastic, rubber, etc.

Instructional Materials

Kits may also be supplied with instructional materials. Instructions may be printed on paper or other substrate and/or may be supplied as an electronic-readable medium such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail. In one embodiment, the instructions instruct the user to combine the luciferase with the ADP converting enzyme and inhibitor of adenylate cyclase before adding the resulting reagent composition to a sample.

Uses for ATP-Dependent Luciferase-Luciferin Reactions

Because the beetle luciferase-luciferin reaction is ATP-dependent, luciferase can be used to assay for ATP. The reaction is remarkably sensitive, allowing ATP to be detected in a sample containing as little as $10^{-16}$ moles ATP or less.

The methods, compositions and kits of the invention provide for the simple qualitative or quantitative detection of ADP generated from a kinase or ATPase reaction via subsequent ATP formation. In one embodiment, a simple qualitative experiment in which luminescence is generated in a sample indicates the presence of a kinase or ATPase. Luminescence is generated using a reagent composition comprising luciferase such as a mutant of LucPpe2. In addition, the reagent composition may further comprise one or more of the following components: luciferin, which may be reconstituted from a lyophilized preparation (alternatively, an appropriate luciferin-analogue substrate), inhibitor(s) of ADP to ATP converting enzymes, divalent cation (e.g. magnesium), enzyme stabilizing agents, and buffer.

The compositions, methods and kits of the invention permit a user to quantify the amount of ADP produced by a kinase or ATPase, or the presence of a kinase or ATPase, in a sample by converting the ADP to ATP and quantifying the amount of luminescence produced after adding an ATP-dependent bioluminescent enzyme. The invention is applied to a sample of interest, and also to samples containing known amounts of ADP, kinase or ATPase (controls). The signal generated from applying the invention to a sample of unknown ADP, kinase or ATPase concentration is correlated to signals generated either by internal controls (the addition of a known amount of ADP, kinase or ATPase to a sample and measuring the subsequent luminescence) or external standard curves, generated by measuring the luminescence of several samples of known ADP, kinase or ATPase concentrations and plotting them graphically. Such methods are known to skilled artisans.

The invention will be further described by the following nonlimiting example.

EXAMPLE

Materials

Pyruvate kinase from rabbit muscle (Sigma Catalog number P9136), myokinase from chicken muscle (Sigma Catalog number M5520), myokinase from rabbit muscle (Sigma Catalog number M3003), creatine phosphokinase from bovine heart (Sigma Catalog number C7886), creatine phosphokinase from rabbit brain (Sigma Catalog number C6638), and creatine phosphokinase from rabbit muscle (Sigma Catalog number C3755) were obtained from Sigma.

Methods

Adenylate Cyclase Assay and Inhibition.

Activity of various adenylyl cyclases (ACs) was measured at 30° C. for 30 minutes in the presence of 60 mM Tris pH 7.5, 10 mM $MgCl_2$, 40 nM calmodulin and variable ATP concentrations. Except for those experiments related to AC titration, 100 ng of the AC was used. When used, the calmodulin antagonists were prepared according to the manufacturer's recommendation and were added directly to the AC reaction when direct inhibition was assessed or to the reaction converting ADP to ATP to assess AC inhibition during ATP formation.

Kinase and ATPase Reactions.

Unless otherwise indicated, kinase or ATPase reactions were performed in 40 μL Buffer A (40 mM Tris pH 7.5, 20 mM $MgCl_2$ and 0.1 mg/mL BSA) in the presence of the kinase or ATPase, ATP, and substrate for the kinase or ATPase. Substrate concentrations and reaction times used are as indicated. Tyrosine kinase reactions were performed in Buffer A supplemented with 2 mM DTT, 2 mM $MnCl_2$ and 100 μM sodium ortho-vanadate. Sphingosine kinase reactions were performed in Buffer A supplemented with 0.5 mM DTT. Hsp70 ATPase reaction was performed in Buffer A supplemented with 7.5 mM KCl and 100 μM DTT. Na+/K+ ATPase reaction was performed in a buffer containing 20 mM Tris pH 7.8, 0.56 mM EDTA, 5 mM $MgCl_2$, 3 mM KCl, and 133 mM NaCl. PgpATPase reaction was performed in a Pgp buffer (Promega Corp). SV40 Large T antigen helicase reaction was performed in a buffer containing 20 mM Tris pH 7.8, 10 mM $MgCl_2$, 50 mM NaCl, and 1 mM DTT. ATP dependent DNase reaction was performed in a buffer containing 33 mM Tris-acetate (pH 7.8), 66 mM potassium acetate, 10 mM magnesium acetate, and 0.5 mM DTT.

ADP Detection Assay.

Figure 3:
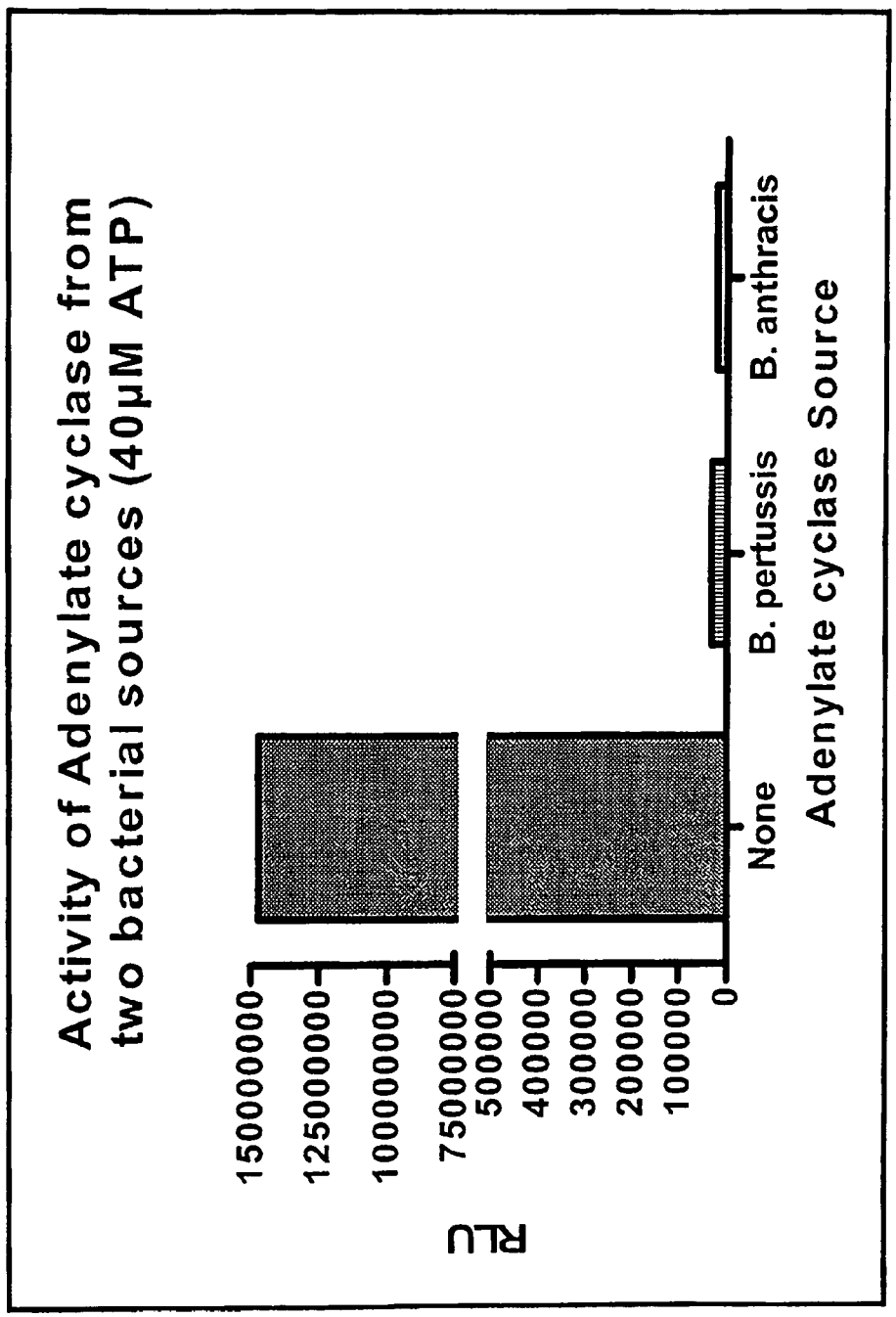
FIG. 3 illustrates ATP depletion with two bacterial ACs, *Bordetella pertussis* and *Bacillus anthracis*.
Figure 4:
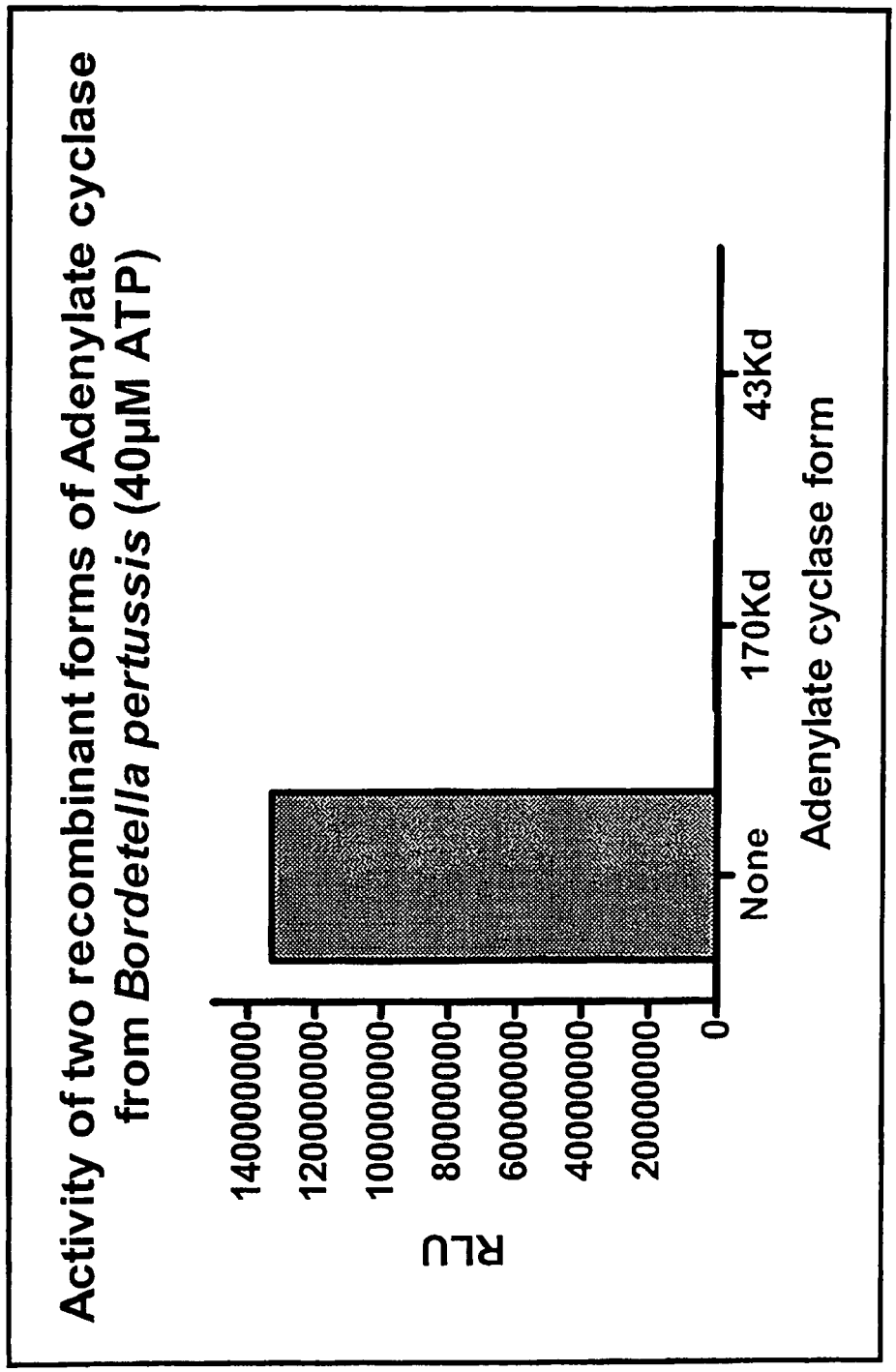
FIG. 4 illustrates that the recombinant full length AC (170 Kd) and catalytic domain (43 Kd) have similar activity.

The assay is performed in multi well plates generally in two steps:

1) ATP Depletion:

40 μL of Reagent 1 (120 mM Tris pH 7.5, 40 nM calmodulin, 20 U/mL pyrophosphatase, 100 ng adenylate cyclase and optionally 300-500 nM staurosporine) was added to the kinase reaction and incubated for 30 minutes. When PI3 lipid kinase, ATPase, sphingosine kinase or hexokinase activities were assayed, staurosporine in Reagent 1 was optionally replaced by 500 nM wortmanin, 75 μM quercetin, 150 μM D-erythro-N,N-dimethylsphingosine or 2 mM glucose-6-phosphate, respectively, to stop the reactions. The ATP depletion assay was also performed using *Bordetella pertussis* full length AC toxin, AC fragment only, or *Bacillus anthracis* Edema factor in the assay (FIGS. 3 and 4).

2) ADP to ATP Conversion and Detection:

80 μL of Reagent 2 (800 μM phosphoenolpyruvate and 800 mU pyruvate kinase in 80 μL Kinase-Glo® Max (Promega Corp.)) were added simultaneously to the kinase or ATPase reaction and incubated for 30-60 minutes at room temperature. The data were collected using a plate reading luminometer (GloMax® 96 Microplate Luminometer).

When the assay was performed in 3 steps, the following modification was introduced. After the ATP depletion step, 20 μL of pyruvate kinase (PK) reagent (40 mM Tris pH 7.0, 335 mM KCl, 500 μM calmidazolium, 500 μM phosphoenolpyruvate, 15 mM EDTA, 0.3 mg/mL BSA and 300-600 mU pyruvate kinase) was added, the reaction incubated for 5-10 minutes, and 100 μL Kinase-Glo® Max (Promega Corp.) was added to detect the ATP produced. After a 10 minute incubation, the plate was read on a plate reading luminometer (GloMax 96 Microplate Luminometer; Promega Corp.).

Figure 29:
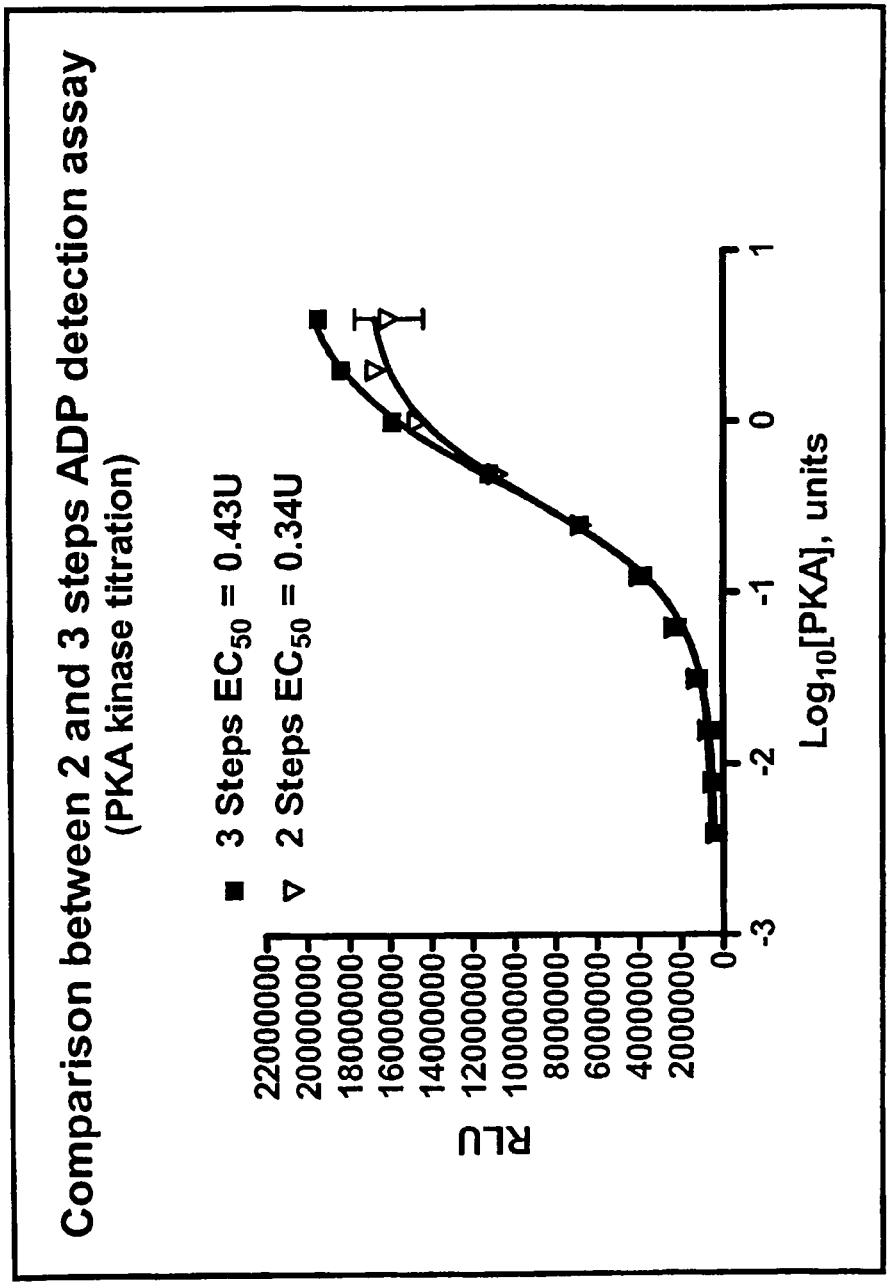
FIG. 29 illustrates the capability of the assay to be performed in 2 or 3 steps with similar results.
Figure 30:
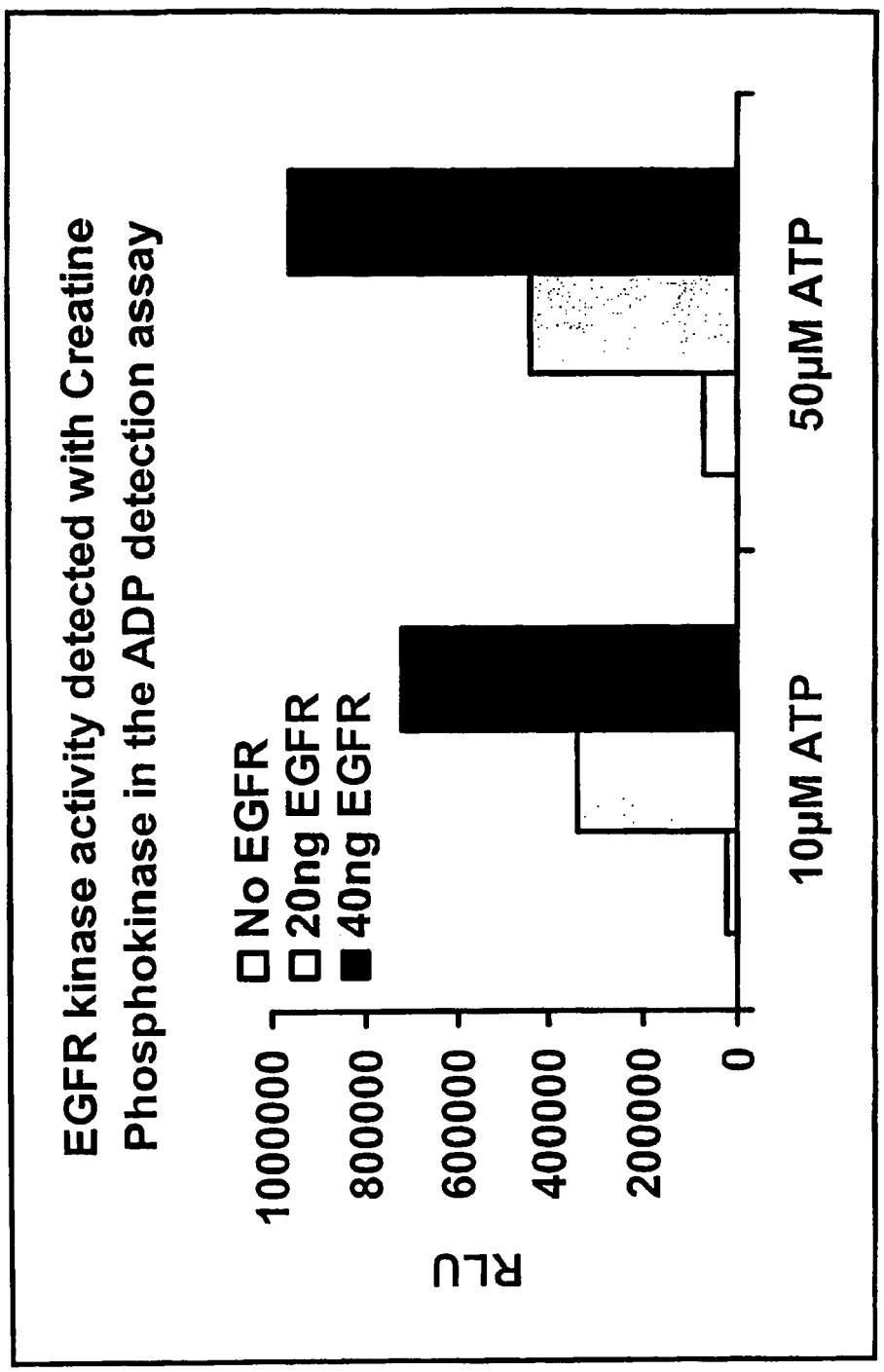
FIG. 30 illustrates the use of creatine phosphokinase in the ADP to ATP conversion step.

In addition to using pyruvate kinase to convert ADP to ATP, adenylate kinase and phosphocreatine kinase were also used to carry out this conversion (FIGS. 29 and 30). For these reactions, either a 125 mU adenylate kinase or 500 mU creatine phosphokinase/250 μM phosphocreatine was used in Buffer B (50 mM Tris pH 7.5, 10 mM $MgCl_2$, and 500 μM calmidazolium) and incubated for 30 minutes at room temperature with the ADP depletion mixture.

Free ATP Depletion Assay.

Two fold serial ATP dilutions were made in 25 μL LB media alone or LB media containing *E. coli* bacteria. Twenty-five micro-liters of ATP depletion Buffer supplemented or not with 100 ng AC, was added to the ATP-Bacteria mixture and incubated for 40 minutes. To detect the remaining cellular or free ATP, 50 μL of BacTiter-Glo (Promega) were added to the mixture and luminescence was recorded according to the manufacturer's procedure. The ATP depletion Buffer contained 80 mM Tris, pH 7.5, 40 nM calmodulin, 10 mM $MgCl_2$, 2 U/mL pyrophosphatase and 0.1 mg/mL BSA.

An exemplary assay was conducted as follows. After providing or conducting a kinase or ATPase reaction which includes ATP, the remaining ATP is eliminated by adding a first reagent (e.g., Reagent 1) that includes an active adenylate cyclase enzyme (AC), one or more a kinase or ATPase inhibitors (e.g., staurosporine) to stop the kinase or ATPase reaction, a buffer and optionally pyrophosphatase (to eliminate any produced pyrophosphate if pyrophosphate is not compatible with subsequent reactions, e.g., pyrophosphate inhibits a luciferase-based reaction) and incubating the reaction, e.g., for about 30 minutes. Optionally, the first reagent may also include an AC that is not activated. Optionally, an activator of the AC, for instance, calmodulin may be added to or along with the first reagent.

Next, the ADP produced by the kinase or ATPase reaction is converted to ATP by adding, a second reagent (e.g., Reagent 2, which includes a buffer, an inhibitor of AC (such as calmidazolium or another calmodulin antagonist), and one or more ADP to ATP converting enzymes and incubating the reaction. Optionally, the second reagent may include a substrate for the ADP to ATP converting enzyme, e.g., phosphoenolpyruvate (PEP) or phosphocreatine (PC). In one embodiment, the ADP to ATP converting enzyme includes pyruvate kinase or creatine phosphokinase which employ PEP or PC, respectively. Alternatively, adenylate kinase can be used to convert ADP to ATP without the need for a phosphate donor.

To measure the newly formed ATP, a third reagent including components for a luciferase/luciferin reaction, was added (e.g., Reagent 3). The relative luminescence units (RLU) produced by this reaction are proportional to the kinase or ATPase activity being measured. Combining the second and third reagent can result in an assay that is highly compatible with high-throughput screening procedures.

Results

Figure 2:
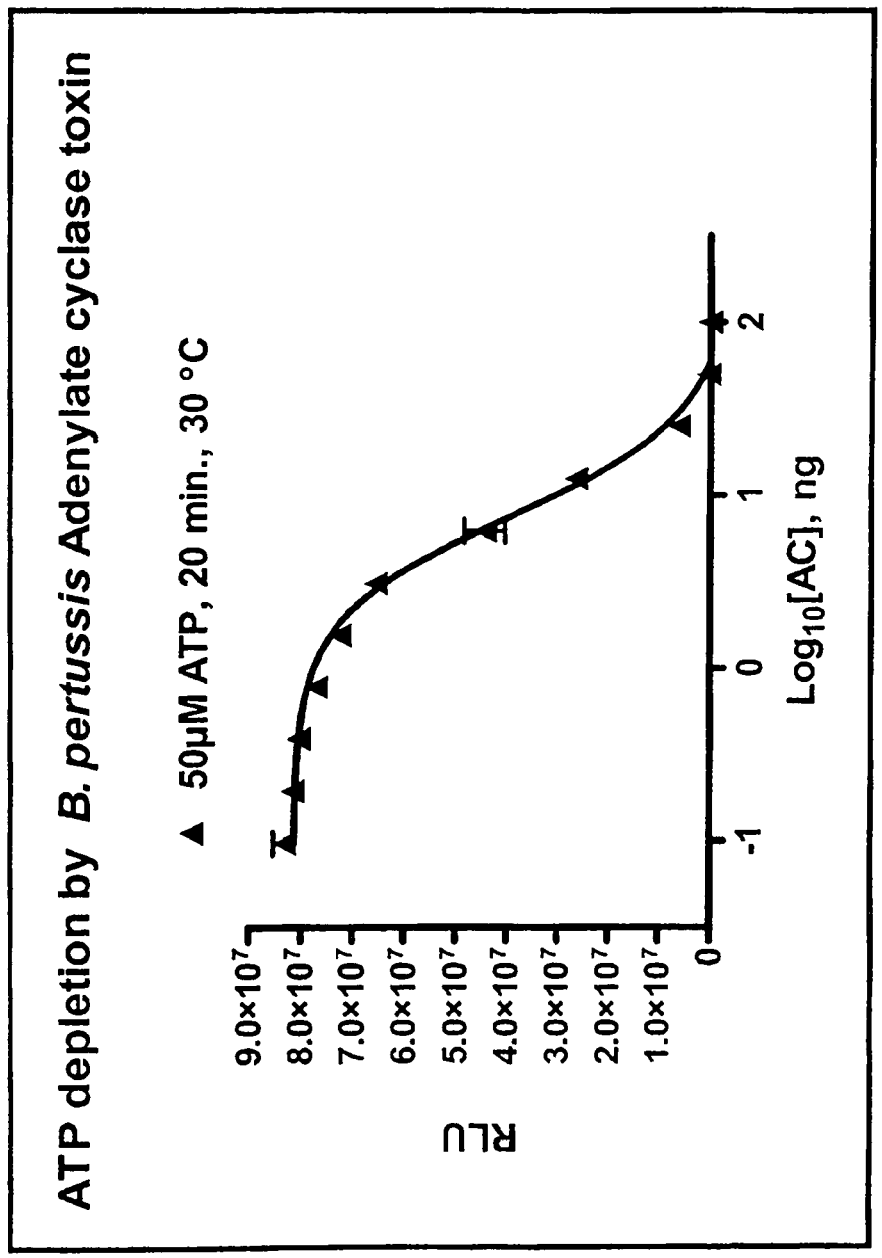
FIG. 2 illustrates the potency of AC to deplete all ATP present in the reaction.

FIG. 2 illustrates that AC from *B. pertussis* can deplete ATP from a kinase or ATPase reaction to a background level using a composition of the invention.

FIG. 3 illustrates that ATP depletion may be performed with different sources of adenylate cyclase such as *B. pertussis* and *B. anthracis*.

FIG. 4 illustrates that ATP depletion may be performed with full-length (170 kD) or with only the catalytic domain (43 kD) of *B. pertussis* adenylate cyclase.

Figure 5:
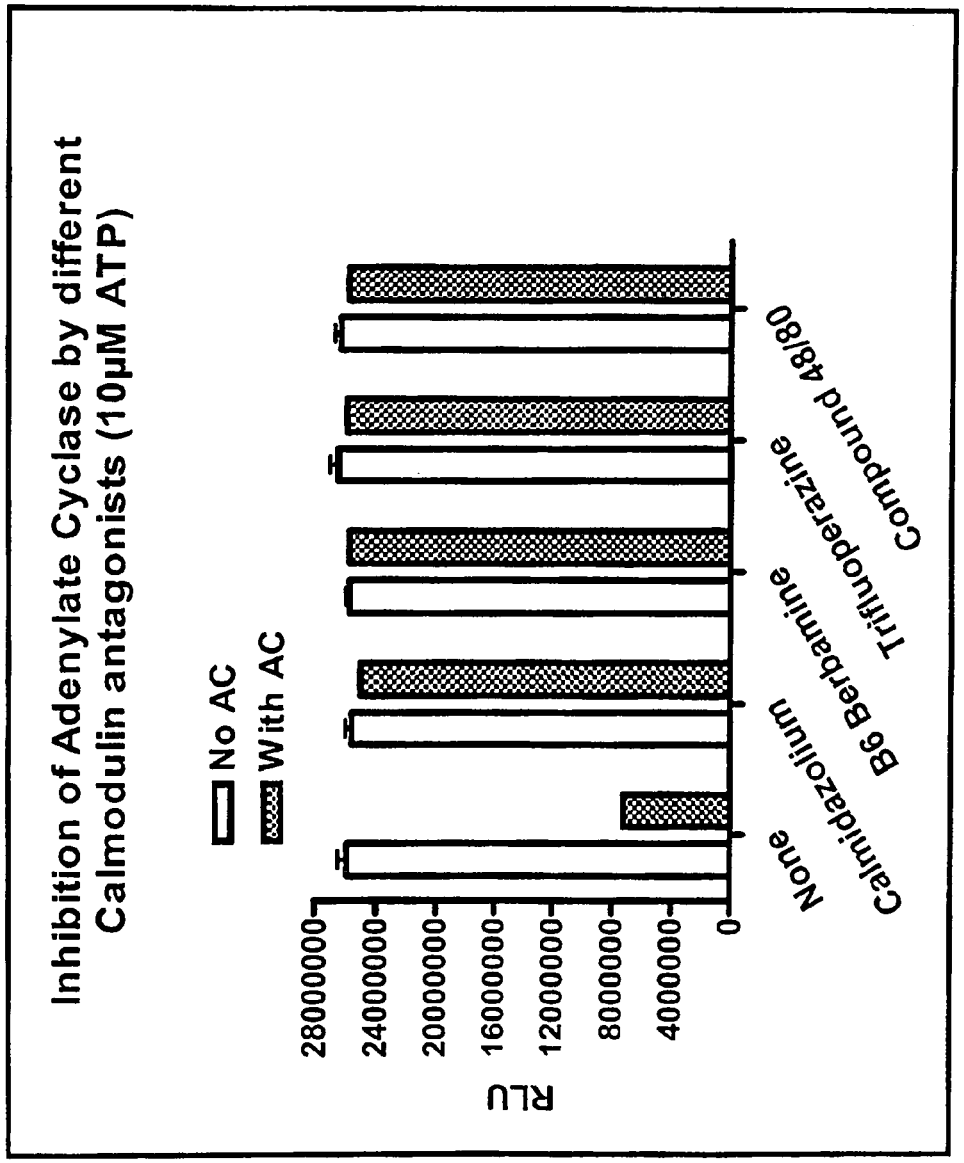
FIG. 5 illustrates the inhibition of AC by 4 calmodulin antagonists.

FIG. 5 illustrates that different calmodulin antagonists (e.g., calmidazolium, B6 barbamine, trifluoroperazine and compound 48/80) may be used as inhibitors of adenylate cyclase when converting ADP to ATP.

Figure 6:
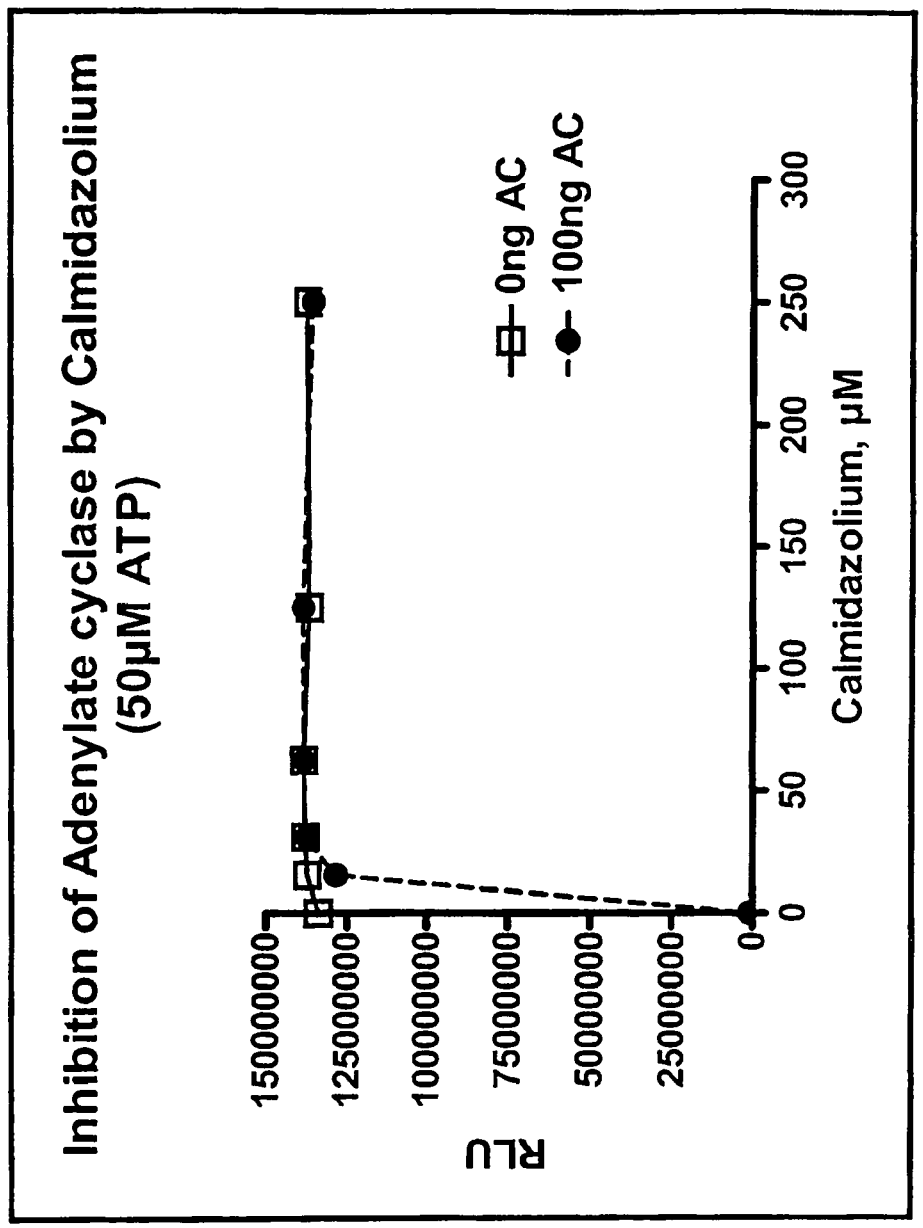
FIG. 6 illustrates the results of calmidazolium inhibition of AC.

FIG. 6 illustrates that AC is inhibited by the calmodulin antagonist calmidazolium. Pyruvate kinase was able to convert ADP to ATP without any significant interference from calmidazolium, even at high calmidozolium concentrations.

Figure 7:
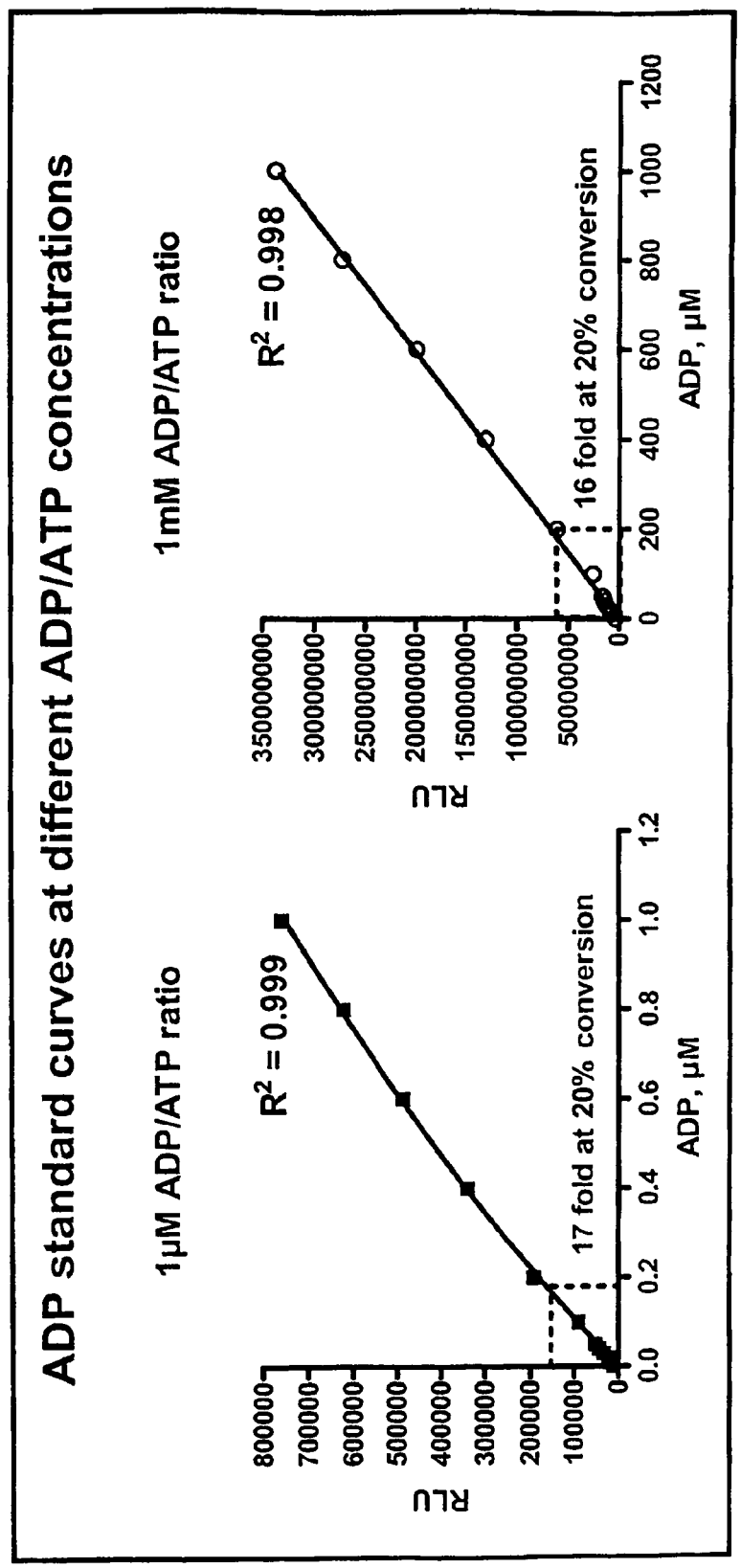
FIG. 7 illustrates the sensitivity of the assay to detect different concentrations of ADP in the presence of ATP.

FIG. 7 shows the sensitivity and linearity of the assay to detect different concentrations of ADP in the presence of ATP.

Figure 8:
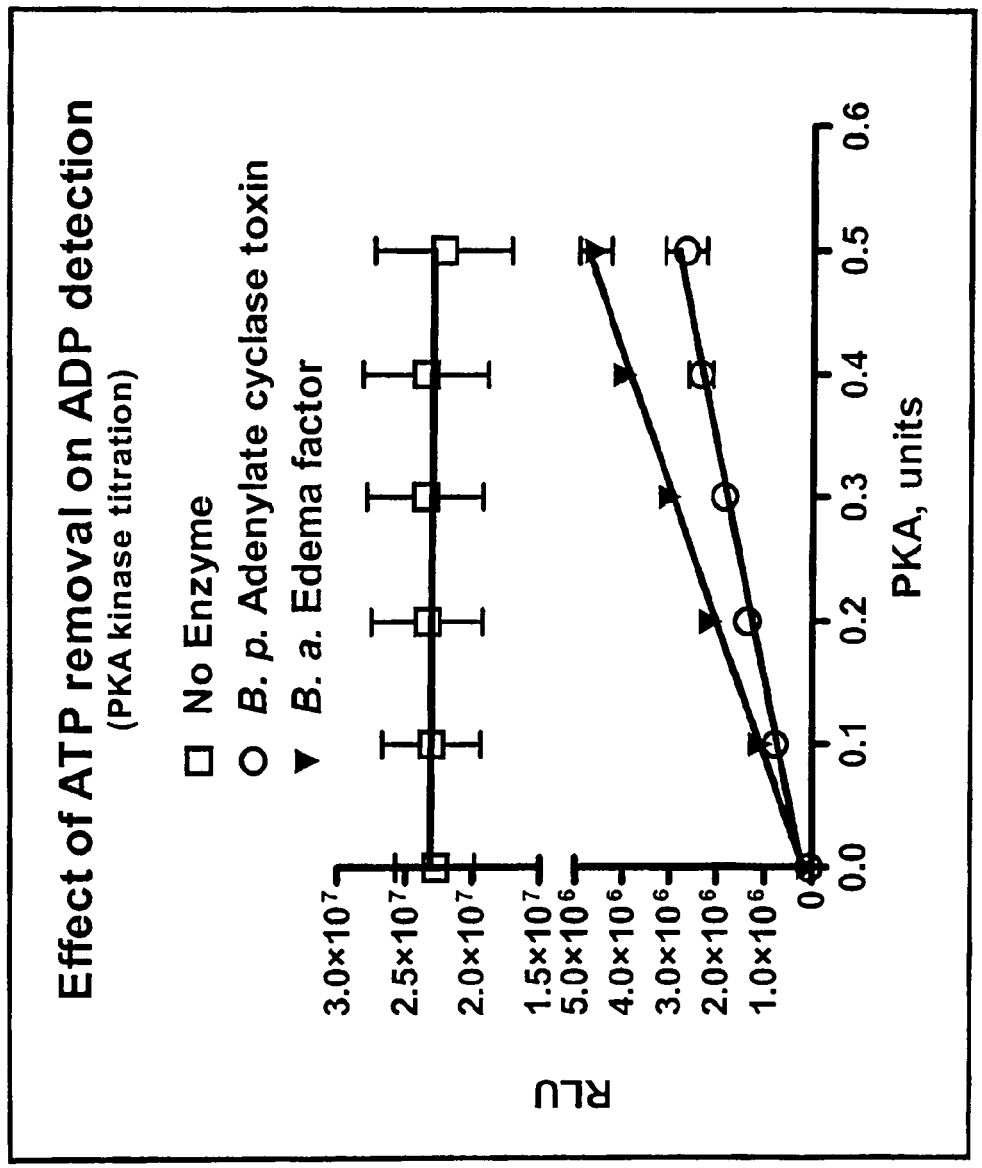
FIG. 8 illustrates the results obtained when AC from two different bacteria was used in the ADP detection assay after a PKA kinase reaction.

FIG. 8 shows that meaningful ADP detection using luminescence can be performed when ATP depletion using AC is performed after the kinase reaction prior to ADP conversion and detection.

Figure 9:
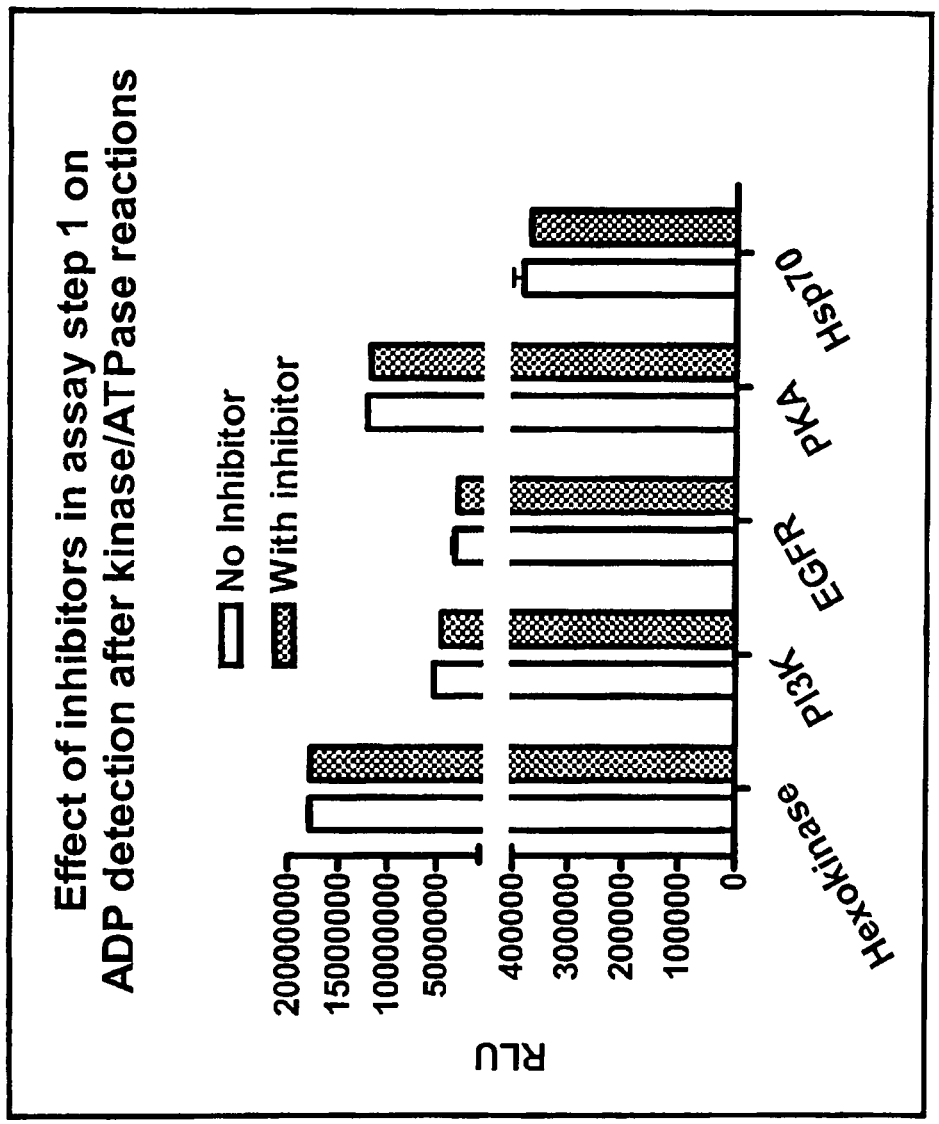
FIG. 9 illustrates the optional use of kinase or ATPase inhibitors to stop the kinase or ATPase reactions.

FIG. 9 shows that an inhibitor of kinase or ATPase can be used optionally to stop the reaction during ATP depletion with no effect on subsequent reactions.

FIGS. 9-22 demonstrate that the activity of a variety of kinase and ATPase enzymes can be detected using the compositions and methods of the present invention.

Figure 10:
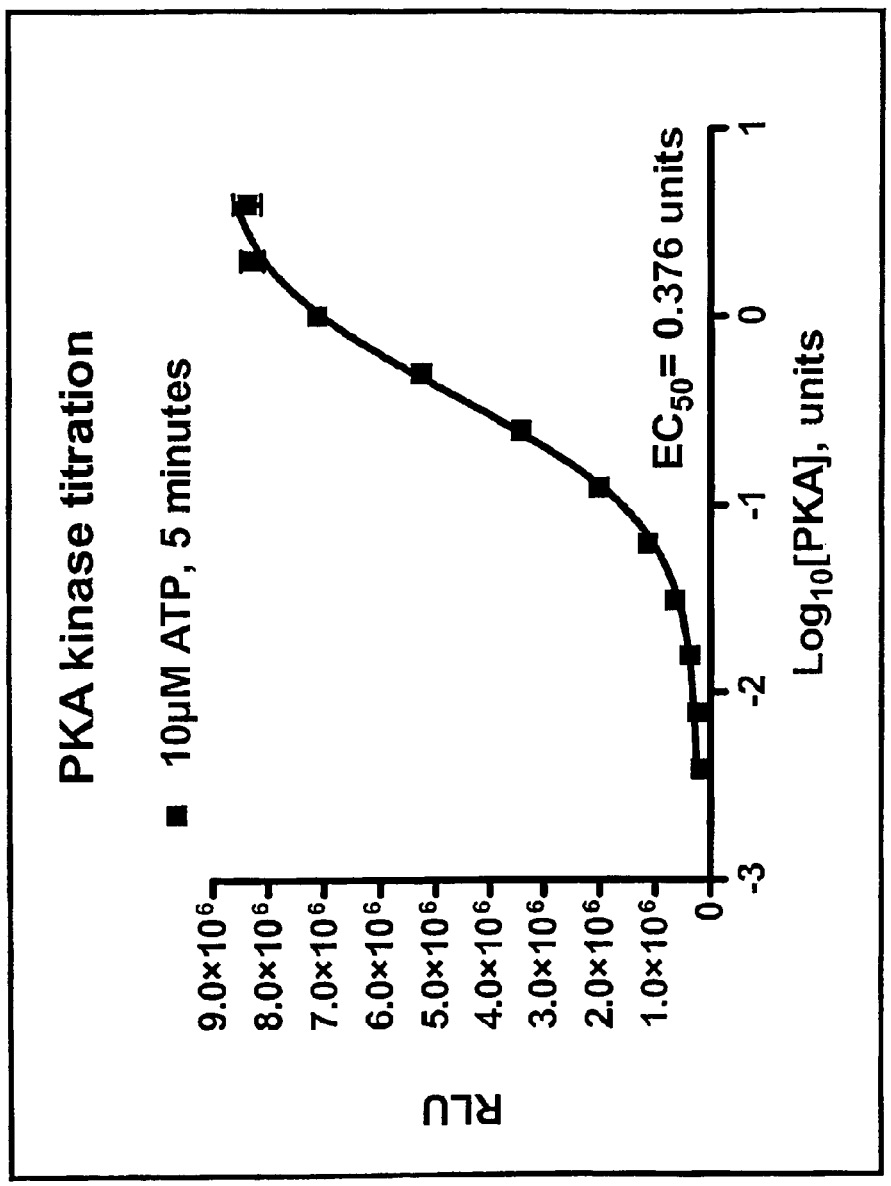
FIG. 10 illustrates the results of the protein kinase PKA titration which employed compositions of the invention.
Figure 11:
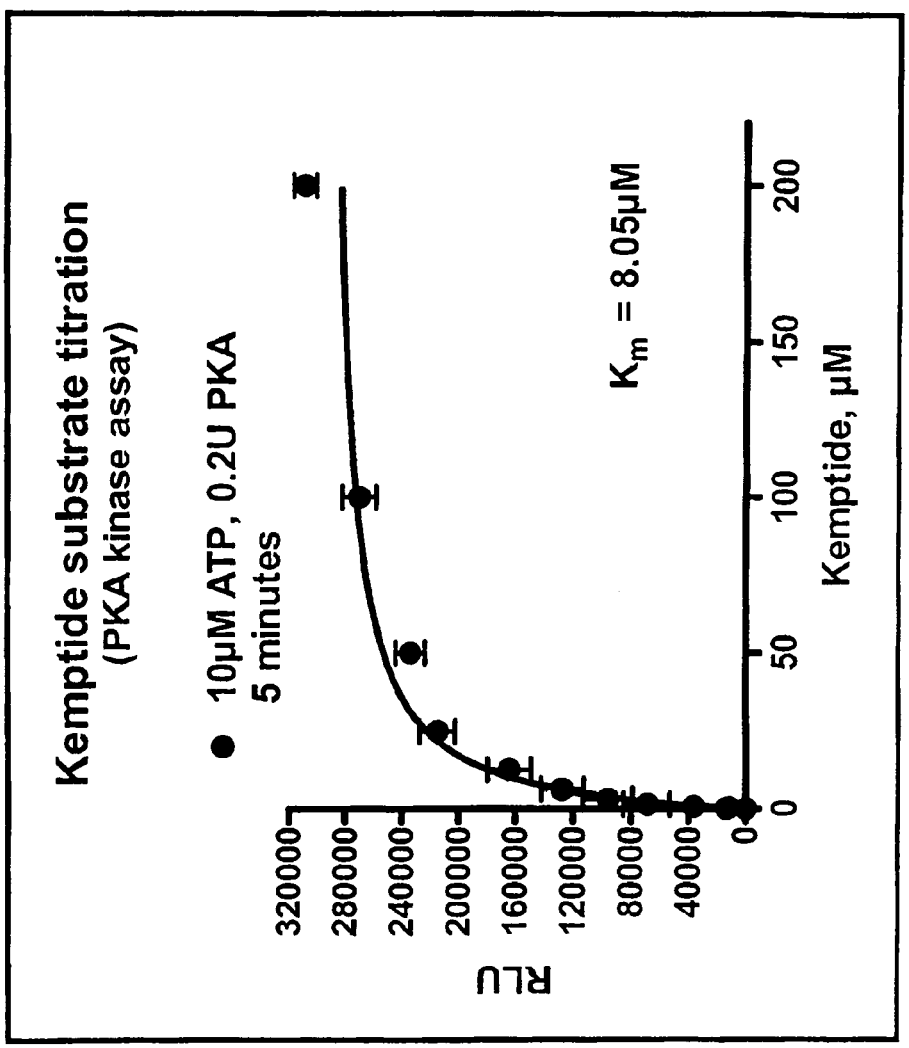
FIG. 11 illustrates the results of PKA substrate (kemptide) titration which employed compositions of the invention.
Figure 12:
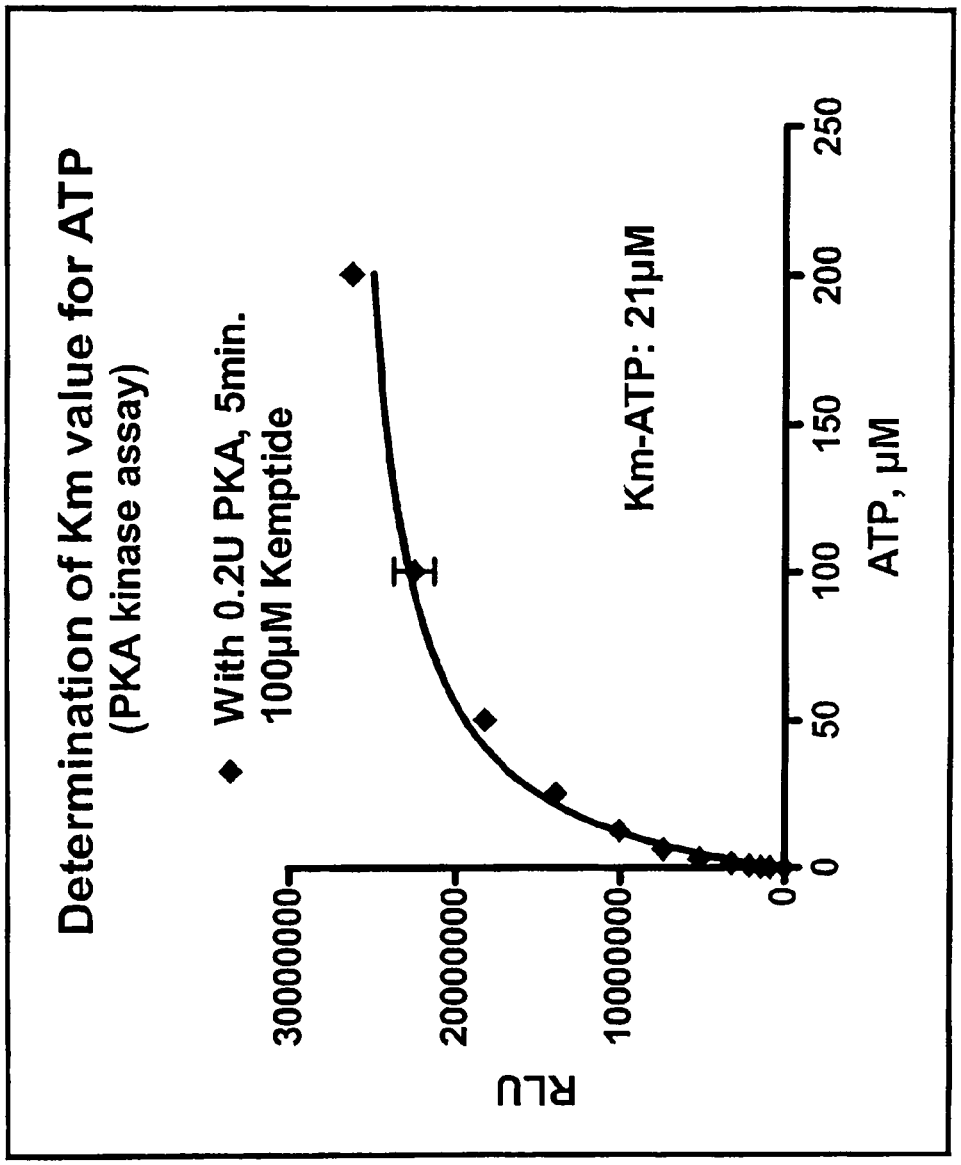
FIG. 12 illustrates the results of ATP titration in a PKA kinase reaction using compositions of the invention.

FIGS. 10-12 demonstrate that the present invention can be used to detect the activity of a protein kinase, PKA. The $K_M$ for ATP in the PKA kinase reaction resulted in a value similar to those previously reported.

Figure 13:
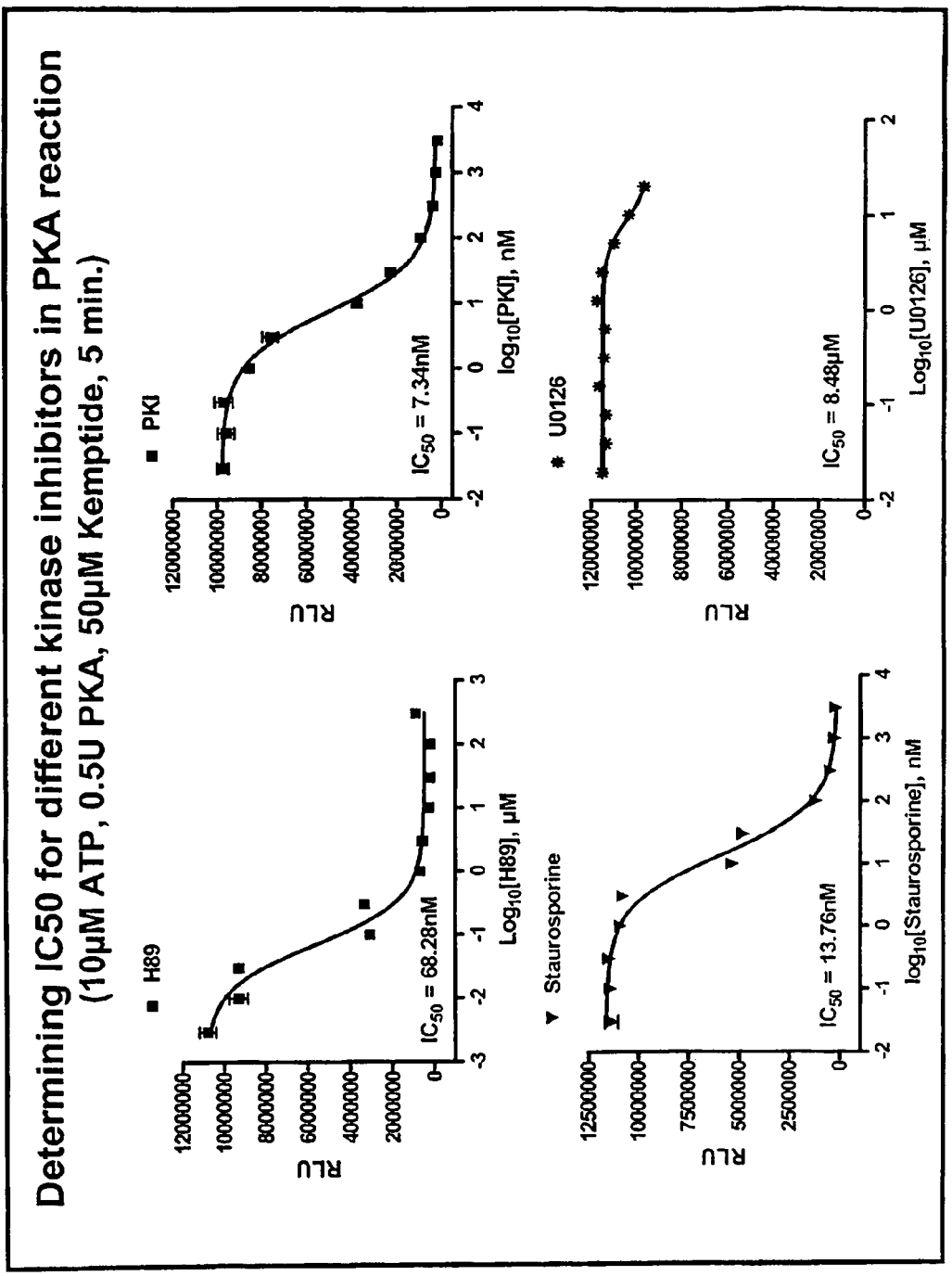
FIG. 13 illustrates the results of the effect of different inhibitors on PKA activity.
Figure 14:
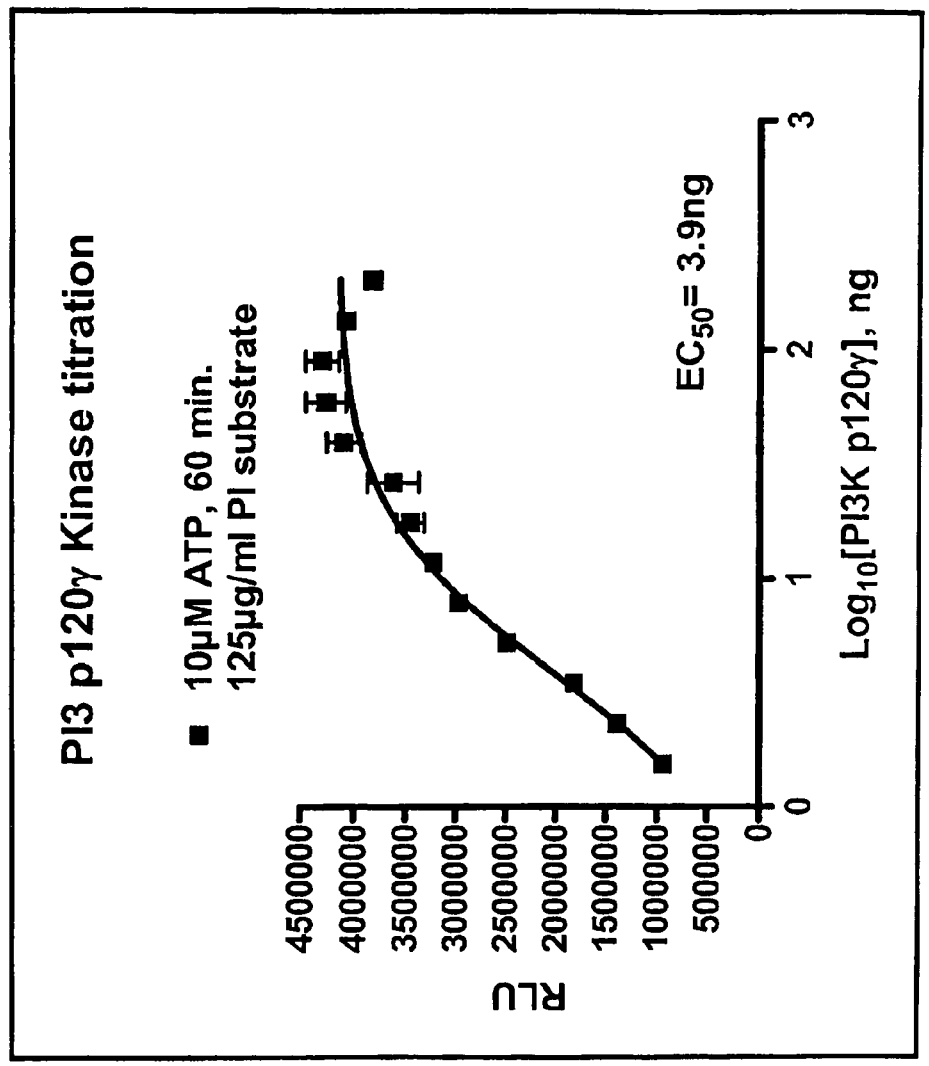
FIG. 14 illustrates the results of the lipid kinase PI3 titration which employed compositions of the invention.
Figure 15:
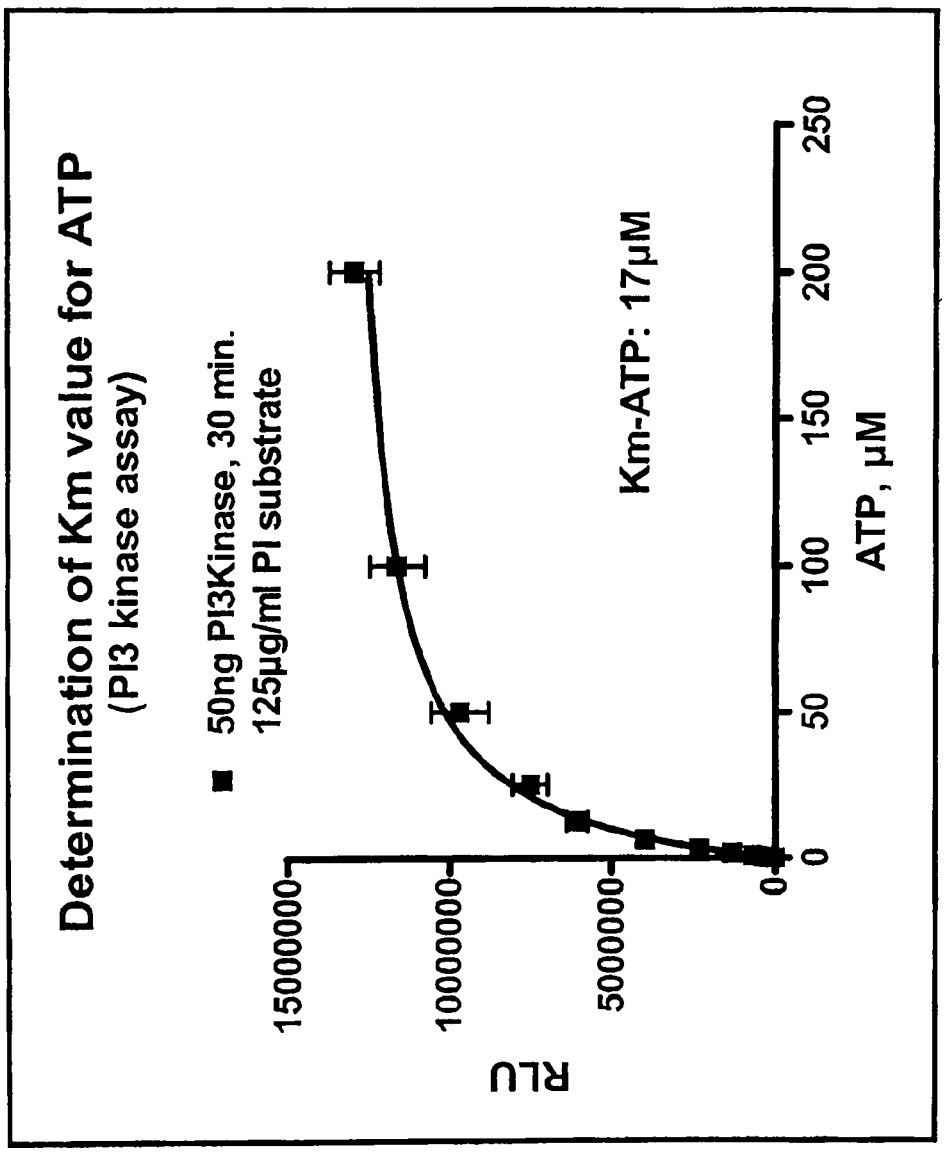
FIG. 15 illustrates the results of ATP titration in a PI3 lipid kinase reaction which used compositions of the invention.
Figure 16:
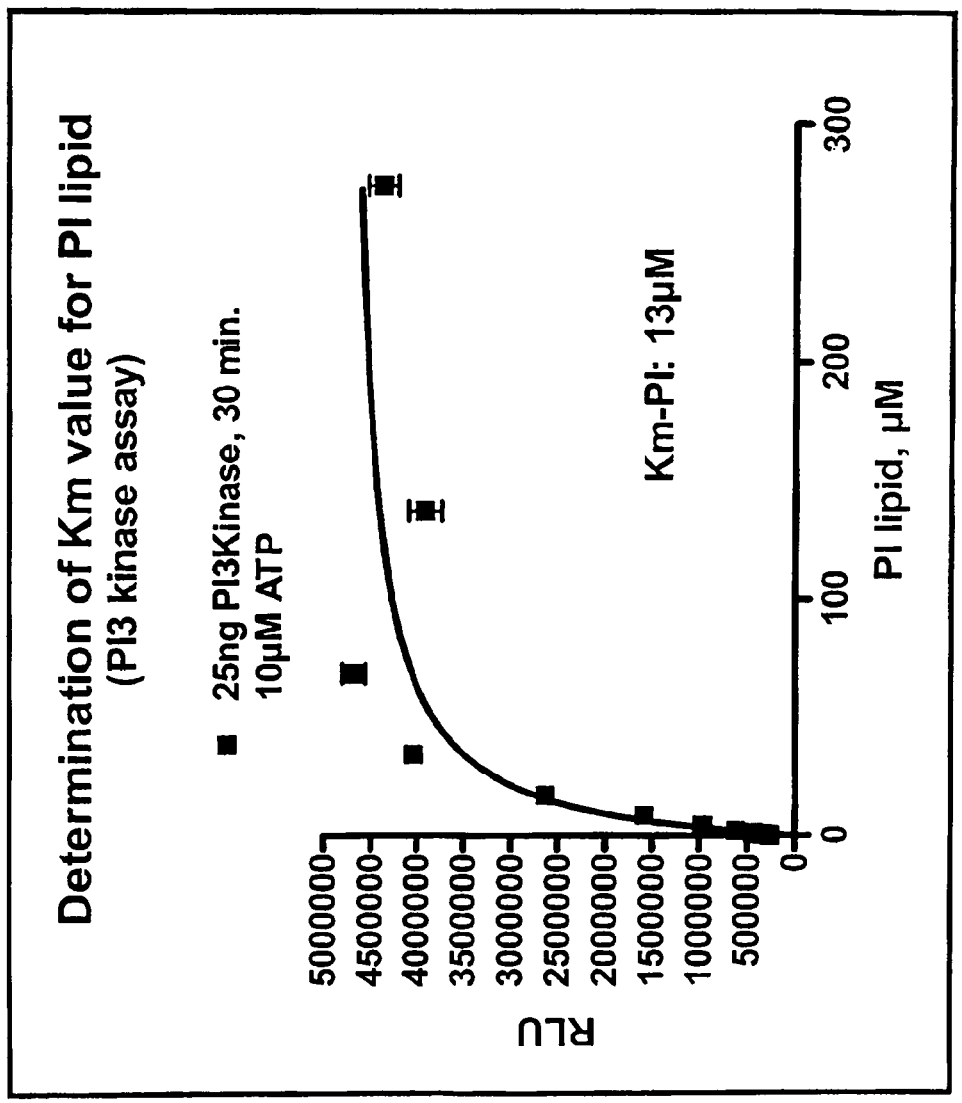
FIG. 16 illustrates the results of PI3 lipid kinase substrate (phosphatidylinositol) titration using compositions of the invention.
Figure 17:
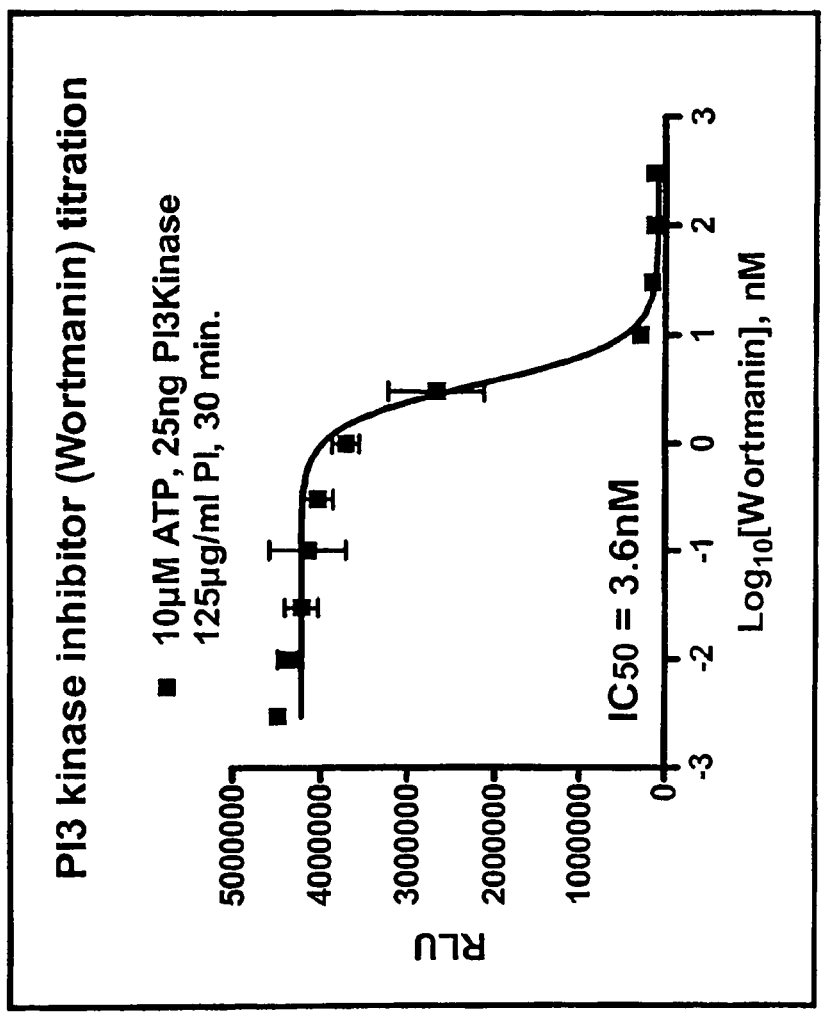
FIG. 17 illustrates the results of a wortmanin induced inhibition of PI3 lipid kinase using compositions of the invention.
Figure 18:
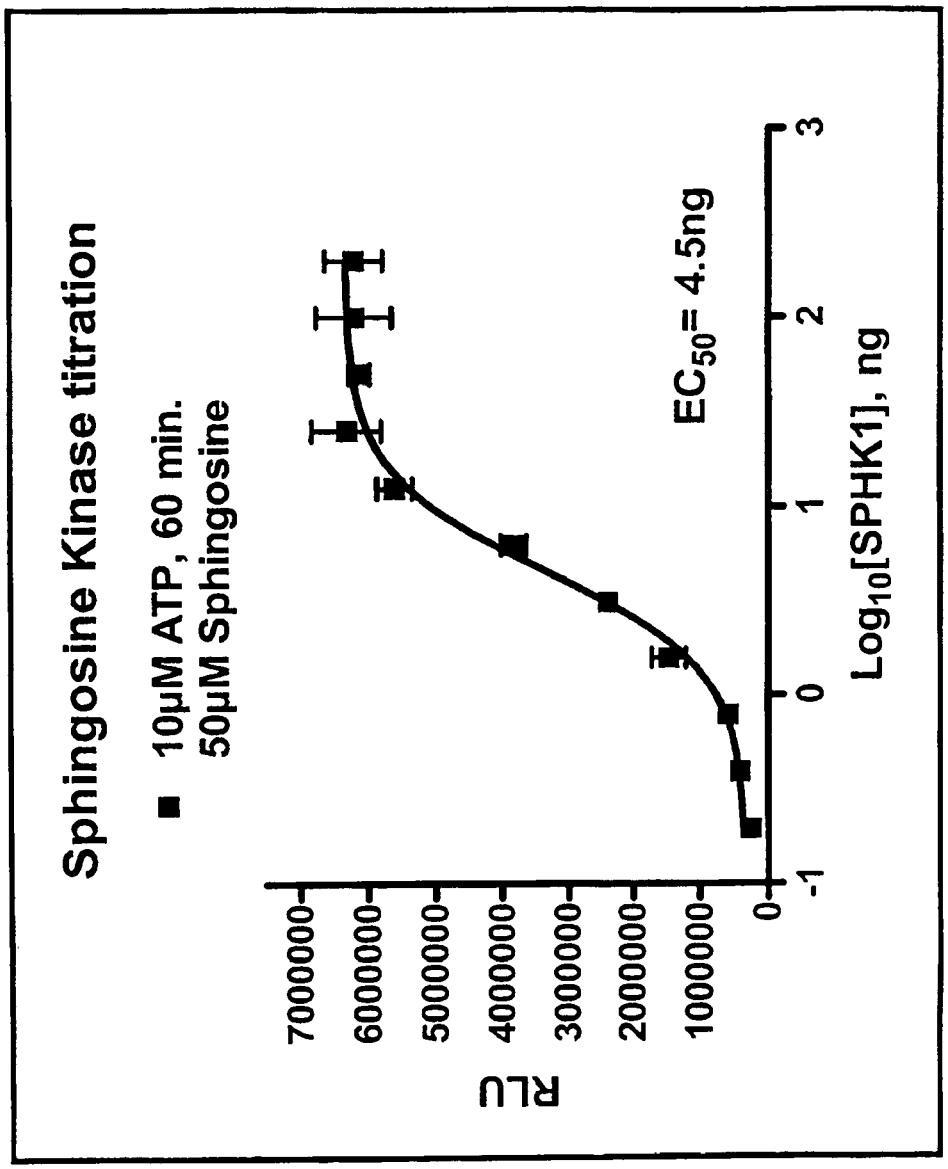
FIG. 18 illustrates the results of sphingosine kinase (SPHK) titration using compositions of the invention.

FIG. 13 demonstrates that the present invention can be used to determine the $IC_{50}$ values of various kinase inhibitors on the protein kinase, PKA. Moreover, in FIG. 13, the use of the staurosporine in the composition of the present invention to inhibit the kinase reaction did not interfere significantly with the pyruvate kinase reaction. Furthermore, in FIG. 13, the tested kinase inhibitors did not interfere with the adenylate cyclase, creatine phosphokinase, or pyruvate kinase reactions.

FIGS. 14-18 demonstrate that the present invention may be used to detect activity from lipid kinases (PI3 kinase and Sphingosine kinase).

Figure 19:
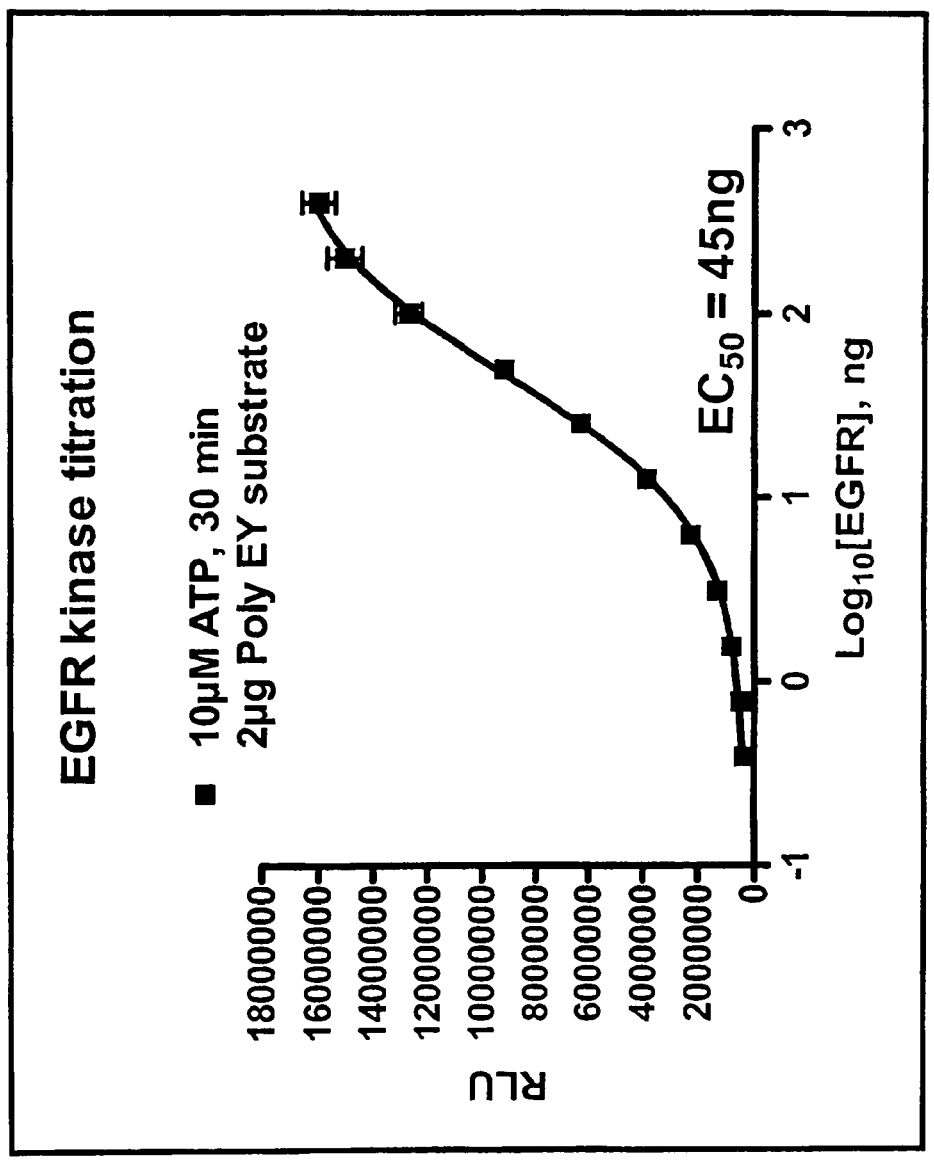
FIG. 19 illustrates the results of receptor tyrosine kinase EGFR titration using compositions of the invention.
Figure 20:
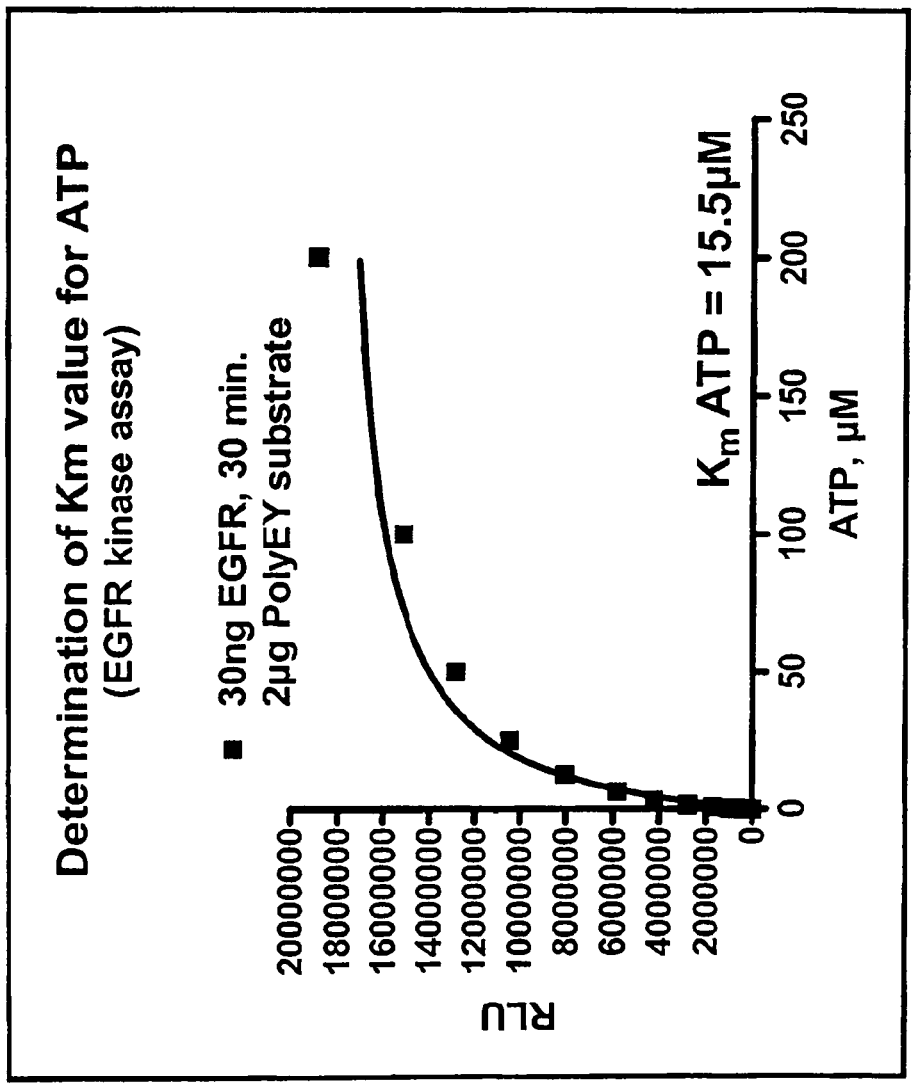
FIG. 20 illustrates the results of ATP titration in an EGFR kinase reaction using compositions of the invention.

FIGS. 19-20 demonstrate that the present invention may be used to detect activity from a receptor tyrosine kinase (EGFR).

Figure 21:
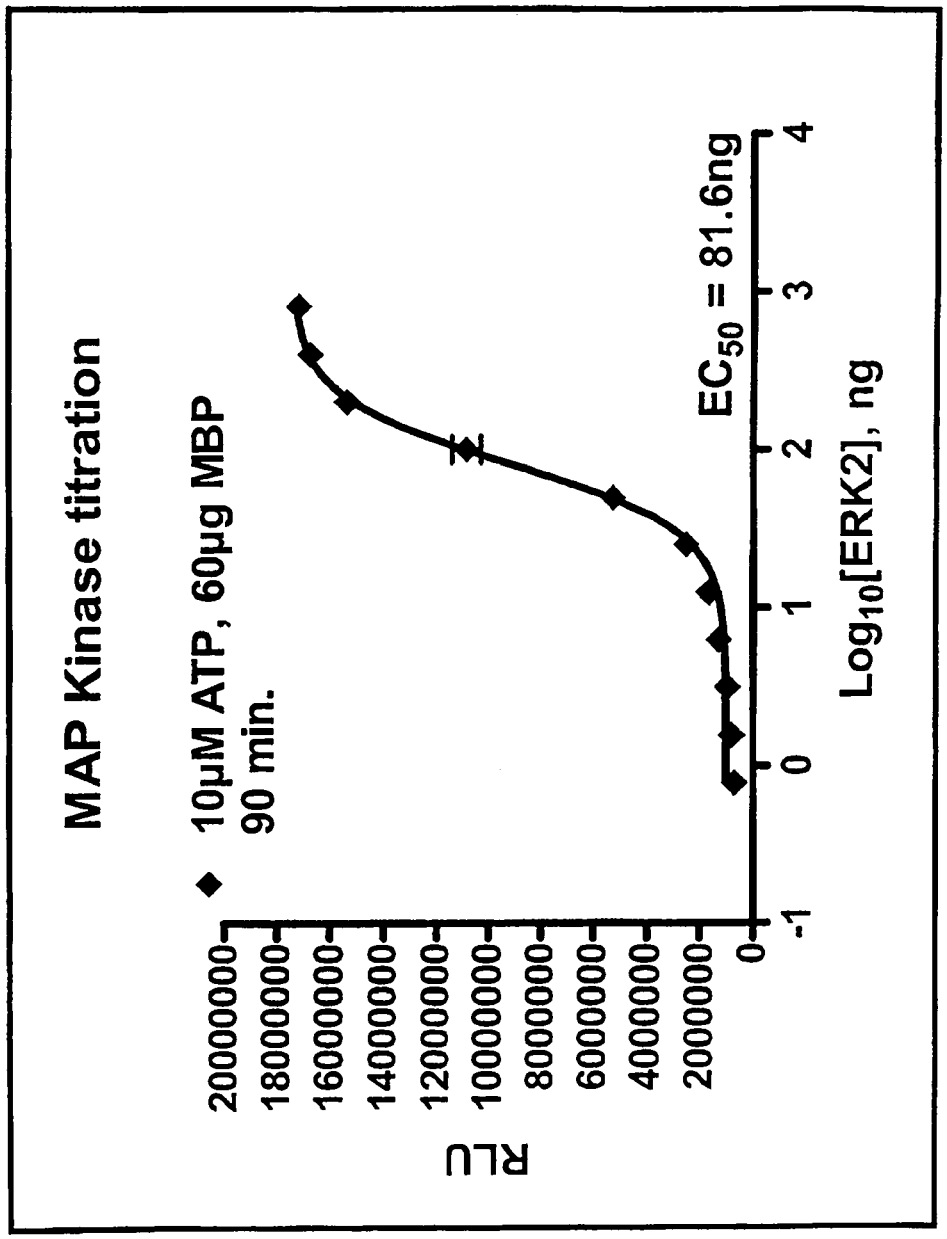
FIG. 21 illustrates the results of the MAP kinase ERK2 titration using a protein substrate (MBP) and compositions of the invention.

FIG. 21 illustrates the use of the present invention to detect activity from MAP kinase using a protein as a substrate (MBP).

Figure 22:
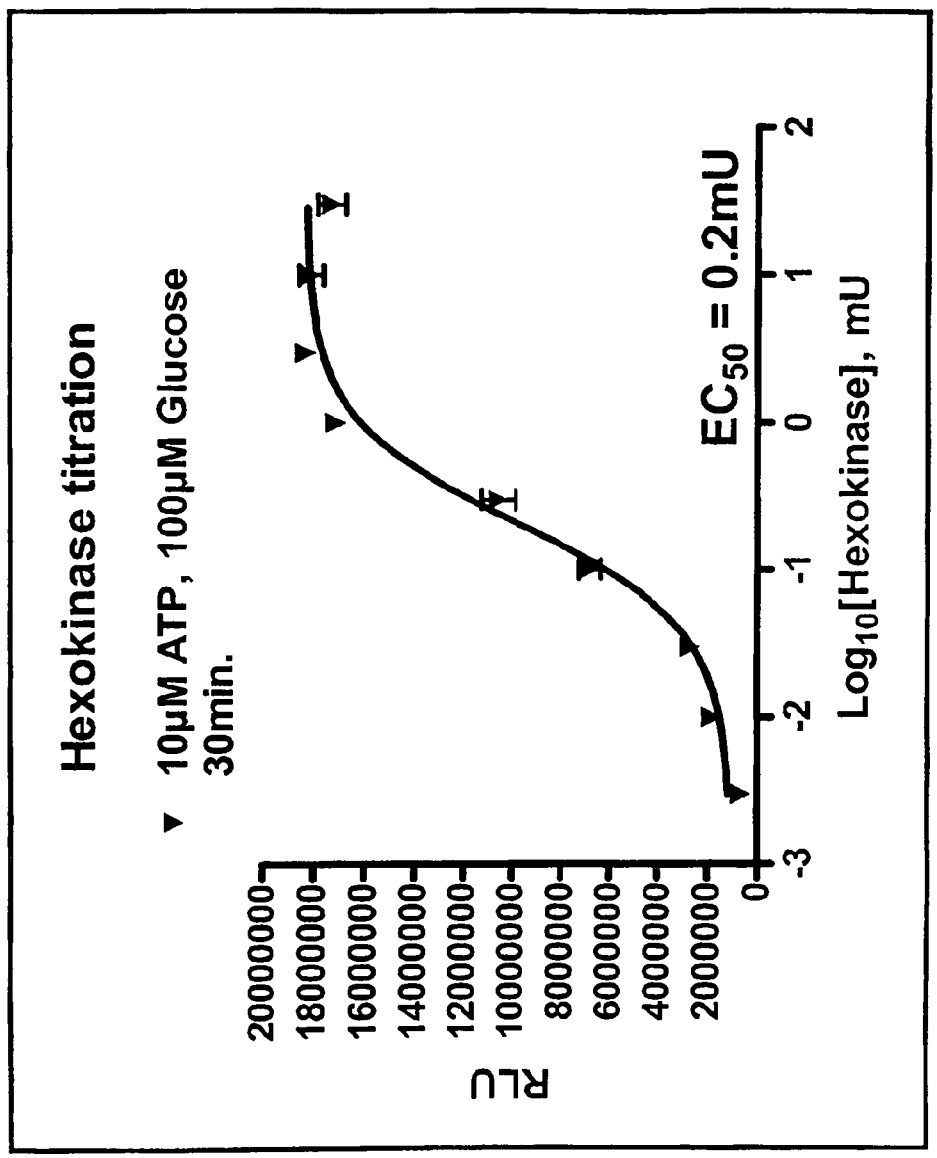
FIG. 22 illustrates the results of the sugar kinase hexokinase titration using glucose as a substrate and compositions of the invention.

FIG. 22 illustrates the use of the present invention to detect activity from a sugar kinase (hexokinase).

FIGS. 23-28 illustrate the use of the present invention to detect activity of enzymes containing an ATPase domain.

Figure 23:
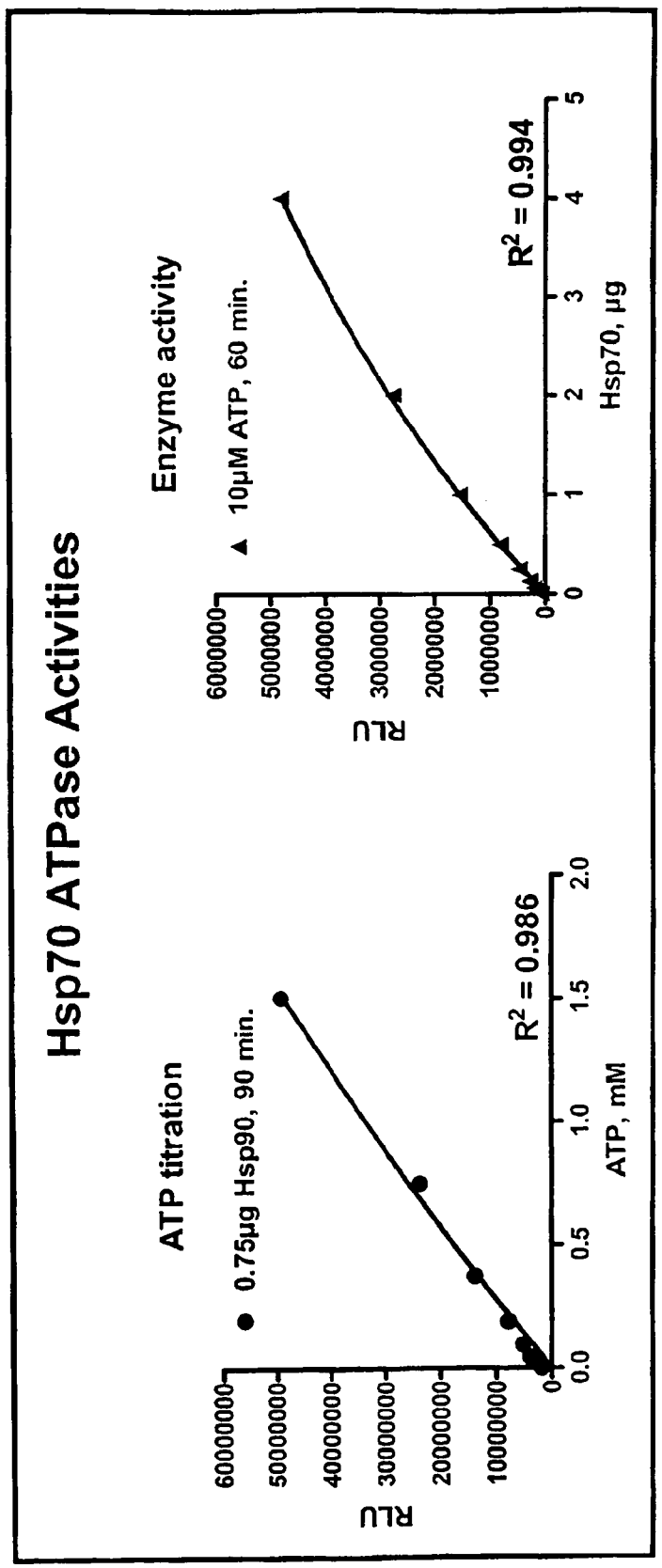
FIG. 23 illustrates the results of ATP and enzyme titration in an Hsp70 ATPase reaction employing compositions of the invention.

FIG. 23 illustrates the use of the present invention to detect ATPase activities of a Heat Shock Protein Hsp70.

Figure 24:
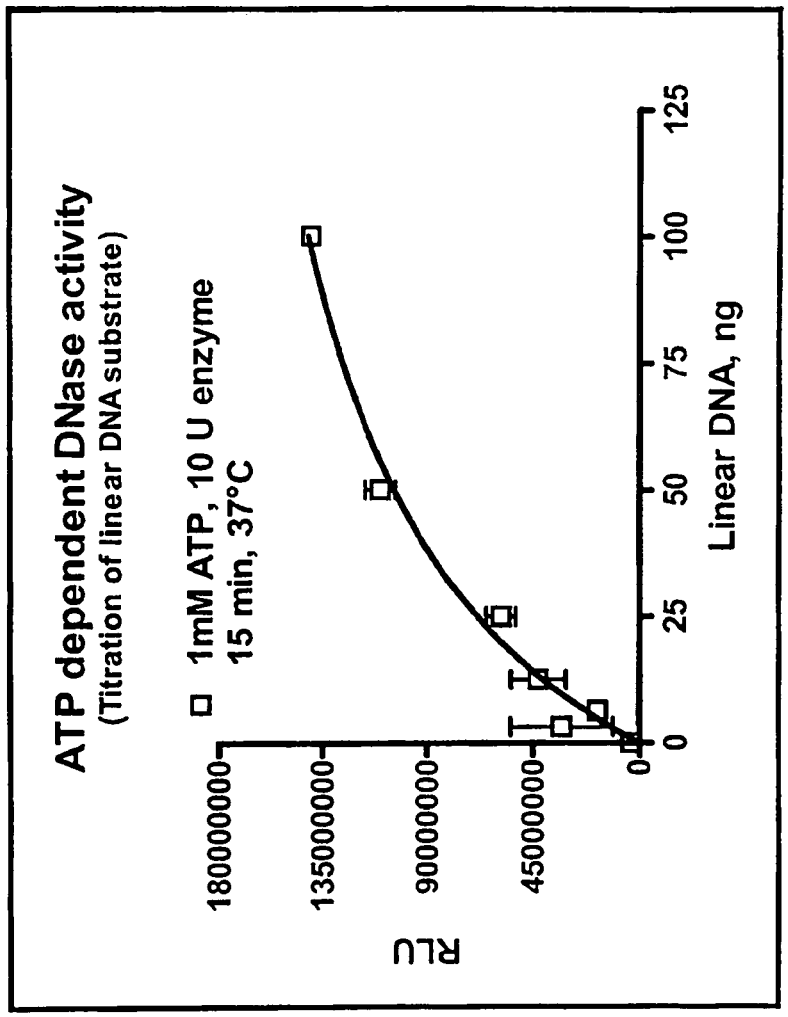
FIG. 24 illustrates the results of linear DNA substrate titration study in an ATP dependent DNase reaction using compositions of the invention.

FIG. 24 shows that the present invention is used to detect levels of linear DNA by monitoring the activity of an ATP dependent DNase. FIG. 24 shows that the present invention can be used for plasmid DNA-based vaccines where the monitoring of linear DNA contamination of plasmid preparations is needed.

Figure 25:
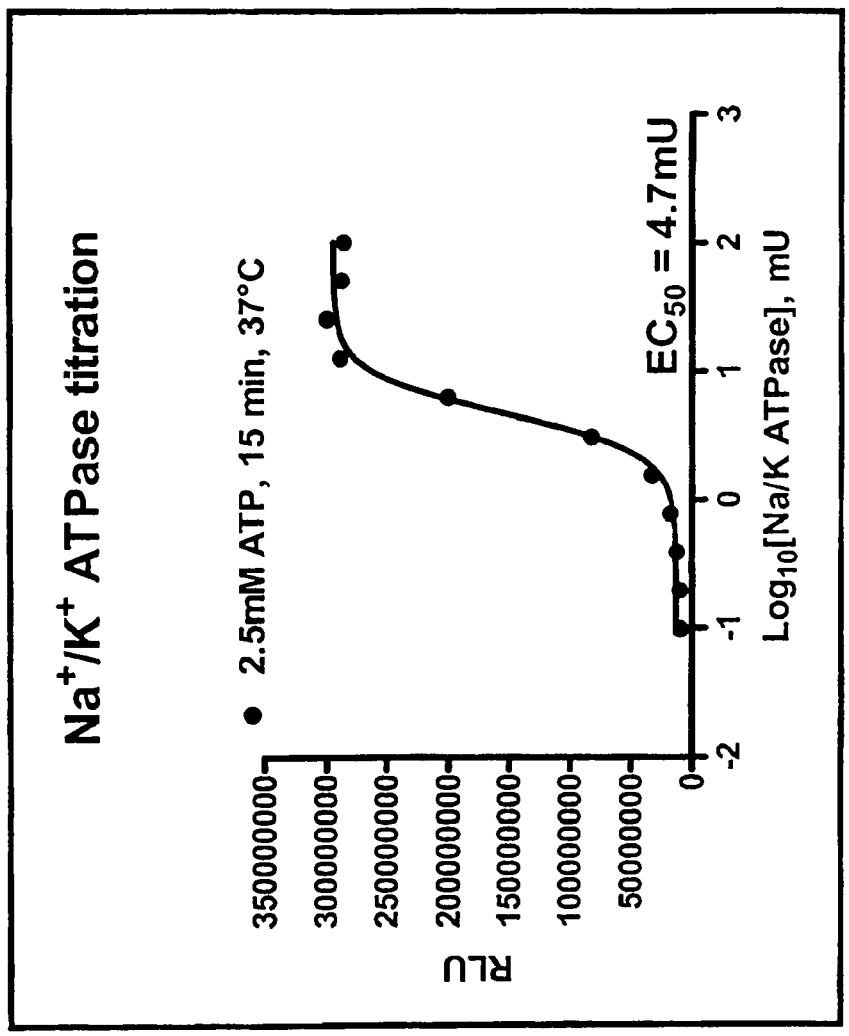
FIG. 25 illustrates the results of the Na+/K+ ATPase titration study using compositions of the invention.
Figure 26:
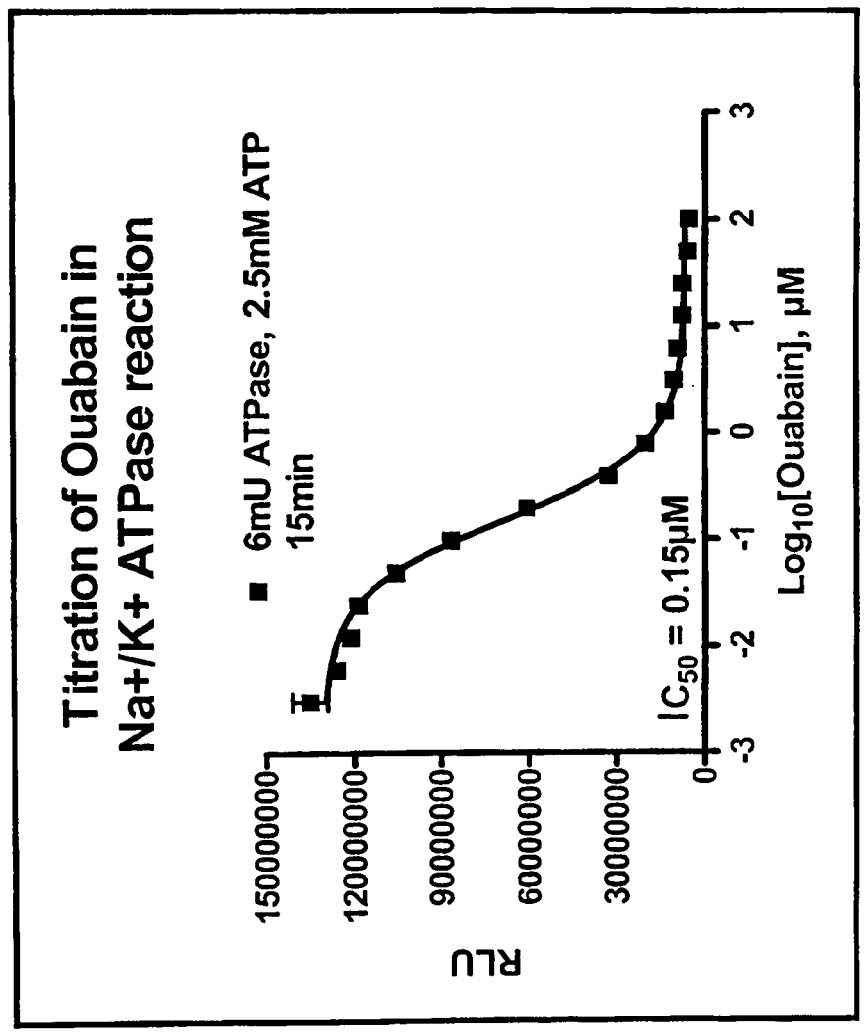
FIGS. 26-27 illustrate the results of the P-glycoprotein (Pgp) activity titration study in the presence of inhibitor and activator drugs using compositions of the invention.

FIGS. 25-26 illustrates the use of the present invention to detect activities of the Na+/K+ ATPase.

Figure 27:
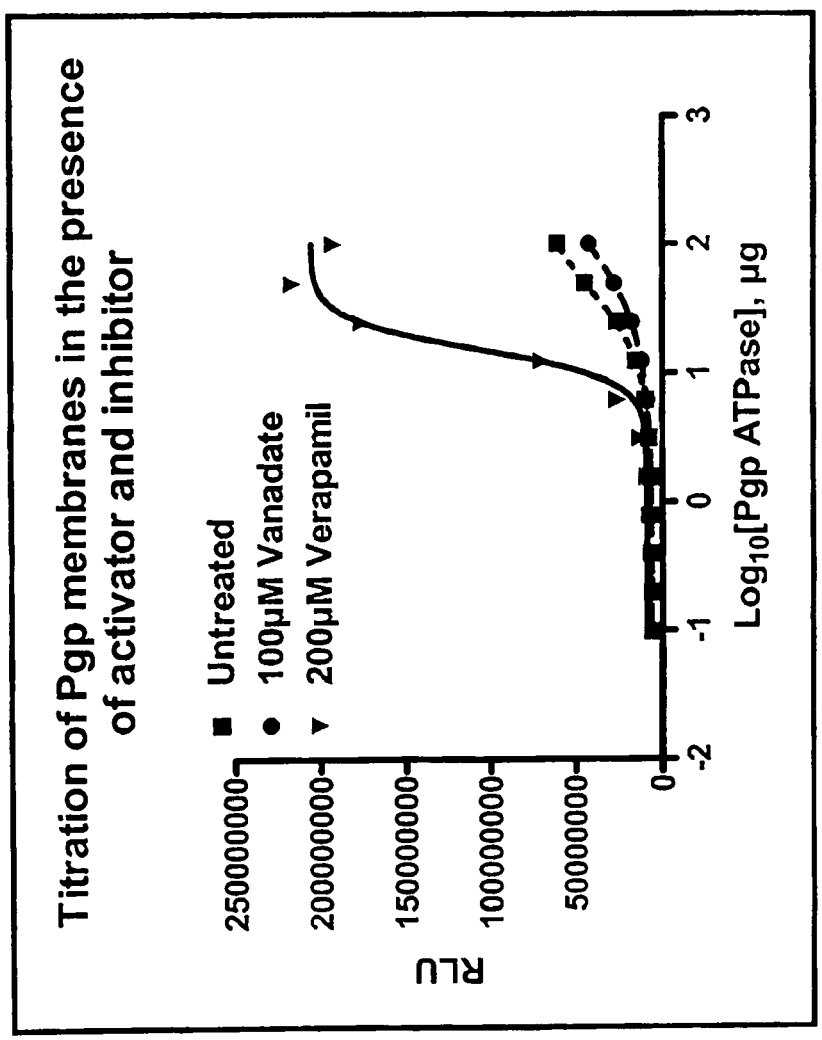

FIG. 27 shows that the present invention can be used to detect activity of a P-glycoprotein whose drug efflux pump activity is ATP dependent. This is important with regard to drug efficacy and multi-drug resistance during disease treatment.

Figure 28:
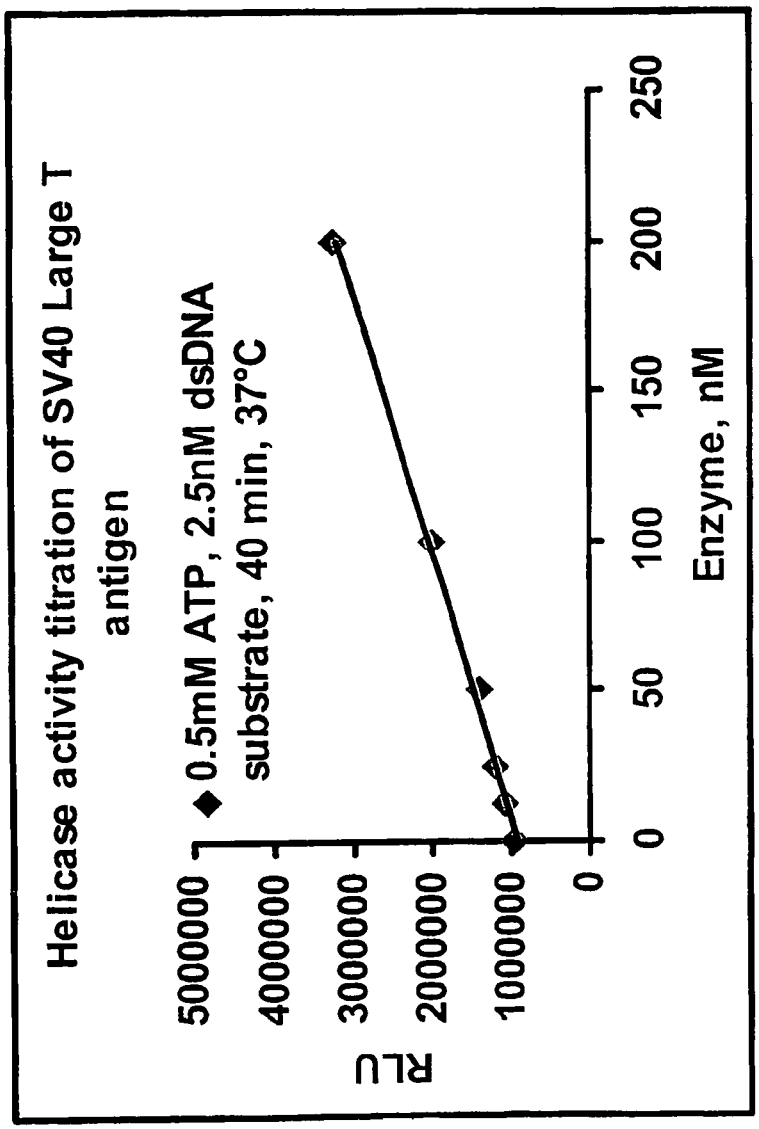
FIG. 28 illustrates the results of the SV40 Large T antigen intrinsic helicase activity titration using compositions of the invention.

FIG. 28 illustrates the use of the present invention to detect the intrinsic ATPase activity of a Helicase (SV40 Large T antigen). FIG. 28 shows that the present invention can be used in diagnostics of viral infections by monitoring viral helicase activities.

FIG. 29 illustrates that the present invention may be performed in two steps (ATP depletion reaction and ADP to ATP conversion/bioluminescent enzyme reaction) or three steps (ATP depletion reaction, ADP to ATP conversion reaction and bioluminescent enzyme reaction), and achieve similar results.

Figure 31:
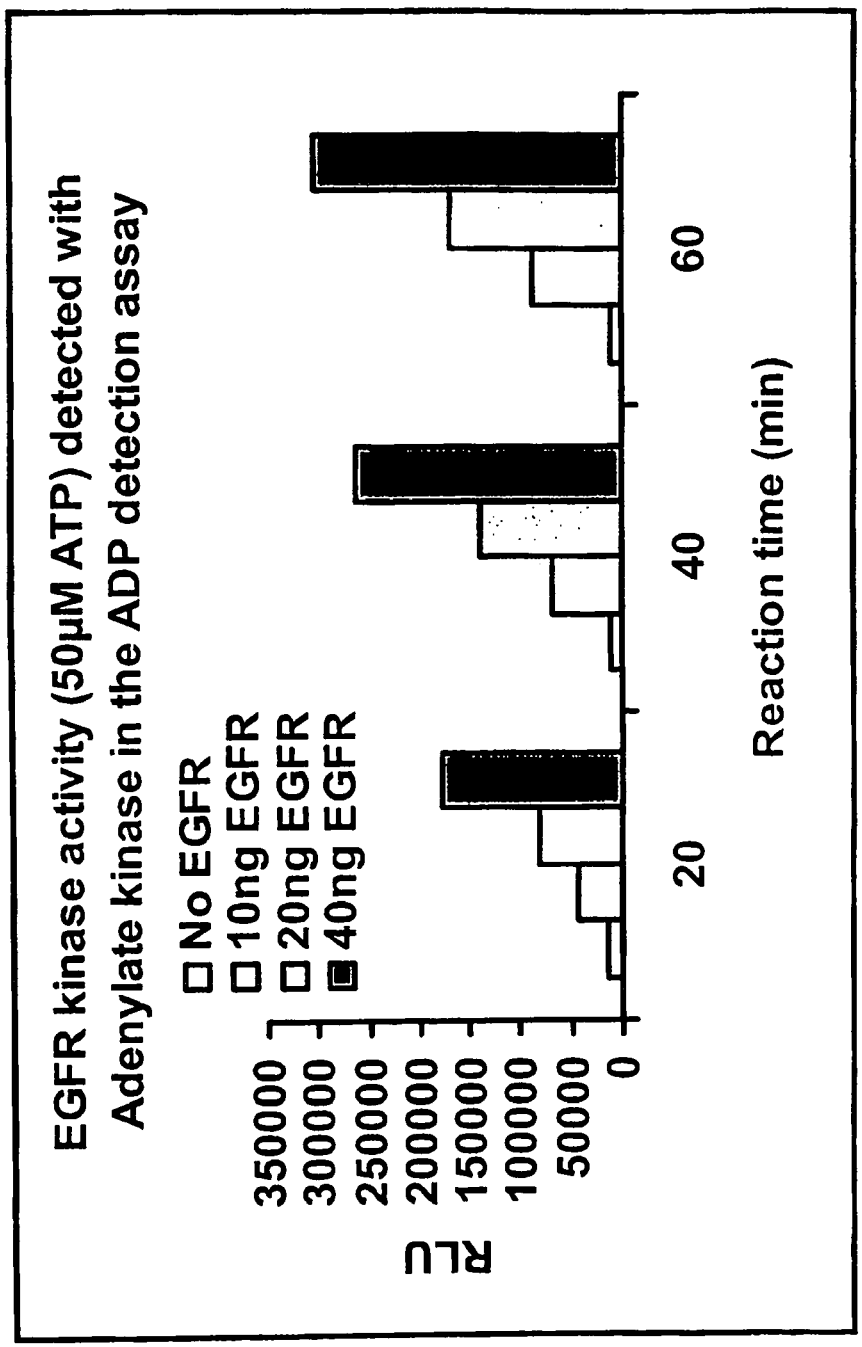
FIG. 31 illustrates the alternative use of adenylate kinase (myokinase) in the ADP to ATP conversion step.

FIGS. 30 and 31 illustrate that various ADP to ATP converting enzymes, creatine phosphokinase and adenylate kinase, respectively, can convert ADP to ATP and therefore may be used in the present invention. It further illustrates that any enzyme known in the art for converting ADP to ATP may be used in the present invention.

The activity of PKA kinase (a high ATP consuming enzyme) and EGFR kinase (a low ATP consuming enzyme) was detected using pyruvate kinase, adenylate kinase and creatine phosphokinase. This data illustrates that the present invention can be used to detect high or low levels of ADP.

Figure 32:
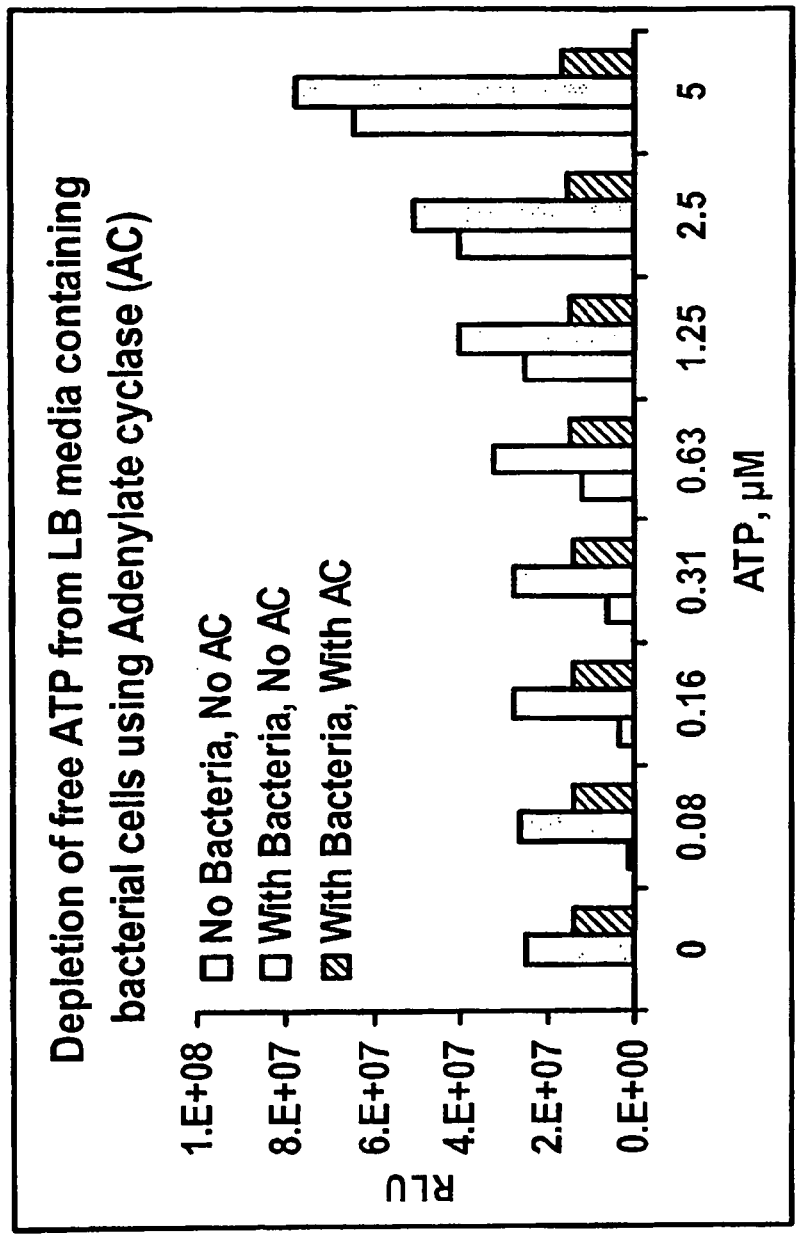
FIG. 32 illustrates the alternative use of the invention to deplete contaminating free ATP from a solution prior to the detection of cellular ATP content.

FIG. 32 shows that adenylate cyclase can be used in the decontamination of free ATP from a cell containing media prior to the detection of intracellular levels of ATP, e.g., after lysis and employing a luciferase-mediated reaction.

Any embodiment described herein can be combined with any other suitable embodiment described herein to provide additional embodiments.

As used herein, reference to "a" or "an" means "one or more." Throughout, the plural and singular should be treated as interchangeable, other than the indication of number.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non limiting example, each range discussed herein can be readily broken down into a lower third, middle third and upper third, etc. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Additionally, for all purposes, the present invention encompasses not only the main group, but also the main group absent one or more of the group members. The present invention also envisages the explicit exclusion of one or more of any of the group members in the claimed invention.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

Reference to a "step" or an indication by a letter or number in the application is used for convenience purposes only and does not categorize, define or limit the invention as set forth herein. All references disclosed herein are specifically incorporated by reference in their entirety.

REFERENCES

Branchini et al. (*Photchem. Photobiol.*, 49:689 (1989).
Branchini et al. (*J. Am. Chem Soc.*, 124:2112 (2002).
Branchini (*Meth. Enzymol.*, 305:188 (2000).
Gietzen et al. *IRCS Med. Sci.*, 8:396 (1980).
Gietzen et al., *Biochem. Biophys. Res. Commun.*, 94:674 (1980).
Gietzen et al. *Biochem. Biophys. Res. Commun.* 101:418 (1981).
Gietzen et al., *Biochem. J.*, 207:541 (1982a).
Gietzen et al., *Mol. Pharmacol.*, 22:413 (1982b).

Gietzen et al. *IRCS Med. Sci.*, 11:12 (1983).
Glaser et al., *Mol. Microbiol.*, 2:19 (1988).
Hong et al., *BBRC*, 335:850 (2005).
Kobayashi et al., *Biochem. Biophys. Res. Commun.*, 88, 1037 (1979).
Ladant et al., *J. Biol. Chem.* 264:4015 (1989).
Levin et al., *Mol. Pharmacol.* 12:581 (1976).
Sala-Newby et al., *FEBS Lett.*, 30:241 (1992).
Volpi et al., *Mol. Pharmacol.* 20:363 (1981).
Watanabe et al., *Experientia*, 35:1487 (1979).
Weiss et al., *Ann. N.Y. Acad. Sci.*, 356:319 (1980).
Wolff et al., *Arch. Biochem. Biophys.*, 173:720 (1976).

While specific embodiments have been described above with reference to the disclosed embodiments and examples, these embodiments and examples are only illustrative and do not limit the scope of the invention. Changes and modifications can be made in accordance with ordinary skill in the art without departing from the invention in its broader aspects as defined in the following claims.

```

The invention claimed is:

1. A kit for detecting ADP in a solution comprising:
   (i) an adenylate cyclase;
   (ii) an enzyme that is capable of catalyzing the conversion of ADP to ATP;
   (iii) a luciferase enzyme; and
   (iv) a substrate for the luciferase enzyme.

2. The kit of claim 1 further comprising one or more of:
   (v) a phosphate group donor;
   (vi) a pyrophosphatase enzyme;
   (vii) one or more detergents;
   (viii) one or more buffer solutions; and/or
   (ix) one or more salts.

3. The kit of claim 1 further comprising a phosphate group donor, wherein the enzyme that is capable of catalyzing the conversion of the ADP to ATP is a pyruvate kinase.

4. The kit of claim 3 wherein the phosphate donor group is phosphoenolpyruvate.

5. The kit of claim 1, wherein the adenylate cyclase is a bacterial adenylate cyclase, or a fragment of a full length bacterial adenylate cyclase with adenylate cyclase activity.

6. The kit of claim 5, wherein the bacterial adenylate cyclase or the fragment is from *Bordetella pertussis* or *Bacillus anthracis*.

7. The kit of claim 1, wherein the adenylate cyclase is a eukaryotic adenylate cyclase, an algal adenylate cyclase, a porcine, non-human primate, canine, bovine, rodent, or human adenylate cyclase, or a fragment thereof with adenylate cyclase activity.

8. The kit of claim 7, wherein the adenylate cyclase is selected from the group consisting of a calmodulin activated eukaryotic adenylate cyclase, a *Spirulina platenis* adenylate cyclase, ADCY1, ADCY2, ADCY3, ADCY4, ADCY5, ADCY6, ADCY7, ADCY8, ADCY9, ADCY10, adenylate cyclase isoform I, adenylate cyclase isoform III, adenylate cyclase isoform VIII, adenylate cyclase isoform V, adenylate cyclase isoform VI, and a fragment thereof with adenylate cyclase activity.

9. The kit of claim 8, wherein the adenylate cyclase is adenylate cyclase isoform I, adenylate cyclase isoform III or adenylate cyclase isoform VIII, and a fragment thereof with adenylate cyclase activity, wherein the adenylate cyclase is stimulated by $Ca^{2+}$/calmodulin.

10. The kit of claim 8, wherein the adenylate cyclase is isoform V, adenylate cyclase isoform VI, and a fragment thereof with adenylate cyclase activity, wherein the adenylate cyclase is inhibited by $Ca^{2+}$ in a calmodulin-independent manner.

11. The kit of claim 1 further comprising phosphoenolpyruvate.

* * * * *

                             SEQUENCE LISTING

<160> NUMBER OF SEQ ID NOS: 15

<210> SEQ ID NO 1
<211> LENGTH: 1706
<212> TYPE: PRT
<213> ORGANISM: Bordetella pertussis

<400> SEQUENCE: 1

Met Gln Gln Ser His Gln Ala Gly Tyr Ala Asn Ala Ala Asp Arg Glu
 1               5                  10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

```
Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
                340                 345                 350

Ala Gly Lys Ser Leu Phe Asp Asp Gly Leu Gly Ala Ala Pro Gly Val
                355                 360                 365

Pro Ser Gly Arg Ser Lys Phe Ser Pro Asp Val Leu Glu Thr Val Pro
370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
                420                 425                 430

Met Thr Arg Gln Val Leu His Ala Gly Ala Arg Gln Asp Asp Ala Glu
                435                 440                 445

Pro Gly Val Ser Gly Ala Ser Ala His Trp Gly Gln Arg Ala Leu Gln
    450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
                485                 490                 495

Ala Ala Ser Leu Ser Ala Ala Val Phe Gly Leu Gly Glu Ala Ser Ser
                500                 505                 510

Ala Val Ala Glu Thr Val Ser Gly Phe Phe Arg Gly Ser Ser Arg Trp
                515                 520                 525

Ala Gly Gly Phe Gly Val Ala Gly Gly Ala Met Ala Leu Gly Gly Gly
                530                 535                 540

Ile Ala Ala Val Gly Ala Gly Met Ser Leu Thr Asp Asp Ala Pro
545                 550                 555                 560

Ala Gly Gln Lys Ala Ala Ala Gly Ala Glu Ile Ala Leu Gln Leu Thr
                565                 570                 575

Gly Gly Thr Val Glu Leu Ala Ser Ser Ile Ala Leu Ala Leu Ala Ala
                580                 585                 590

Ala Arg Gly Val Thr Ser Gly Leu Gln Val Ala Gly Ala Ser Ala Gly
                595                 600                 605

Ala Ala Ala Gly Ala Leu Ala Ala Ala Leu Ser Pro Met Glu Ile Tyr
                610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Glu Gly Asp Ala Leu Leu Ala Gln
                645                 650                 655

Leu Tyr Arg Asp Lys Thr Ala Ala Glu Gly Ala Val Ala Gly Val Ser
                660                 665                 670

Ala Val Leu Ser Thr Val Gly Ala Ala Val Ser Ile Ala Ala Ala Ala
                675                 680                 685

Ser Val Val Gly Ala Pro Val Ala Val Thr Ser Leu Leu Thr Gly
                690                 695                 700

Ala Leu Asn Gly Ile Leu Arg Gly Val Gln Gln Pro Ile Ile Glu Lys
705                 710                 715                 720
```

```
Leu Ala Asn Asp Tyr Ala Arg Lys Ile Asp Glu Leu Gly Gly Pro Gln
                725                 730                 735

Ala Tyr Phe Glu Lys Asn Leu Gln Ala Arg His Glu Gln Leu Ala Asn
        740                 745                 750

Ser Asp Gly Leu Arg Lys Met Leu Ala Asp Leu Gln Ala Gly Trp Asn
            755                 760                 765

Ala Ser Ser Val Ile Gly Val Gln Thr Thr Glu Ile Ser Lys Ser Ala
770                 775                 780

Leu Glu Leu Ala Ala Ile Thr Gly Asn Ala Asp Asn Leu Lys Ser Val
785                 790                 795                 800

Asp Val Phe Val Asp Arg Phe Val Gln Gly Glu Arg Val Ala Gly Gln
                805                 810                 815

Pro Val Leu Asp Val Ala Ala Gly Gly Ile Asp Ile Ala Ser Arg
            820                 825                 830

Lys Gly Glu Arg Pro Ala Leu Thr Phe Ile Thr Pro Leu Ala Ala Pro
            835                 840                 845

Gly Glu Glu Gln Arg Arg Arg Thr Lys Thr Gly Lys Ser Glu Phe Thr
            850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
                885                 890                 895

Val Asp Ala Asn Gly Val Leu Lys His Ser Ile Lys Leu Asp Val Ile
                900                 905                 910

Gly Gly Asp Gly Asp Val Val Leu Ala Asn Ala Ser Arg Ile His
            915                 920                 925

Tyr Asp Gly Gly Ala Gly Thr Asn Thr Val Ser Tyr Ala Ala Leu Gly
    930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Thr Thr Ala Tyr Gly Lys Arg Thr Glu Asn Val Gln Tyr Arg His
            980                 985                 990

Val Glu Leu Ala Arg Val Gly Gln Val Val Glu Val Asp Thr Leu Glu
            995                 1000                1005

His Val Gln His Ile Ile Gly Gly Ala Gly Asn Asp Ser Ile Thr Gly
        1010                1015                1020

Asn Ala His Asp Asn Phe Leu Ala Gly Gly Ser Gly Asp Asp Arg Leu
1025                1030                1035                1040

Asp Gly Gly Ala Gly Asn Asp Thr Leu Val Gly Gly Glu Gly Gln Asn
                1045                1050                1055

Thr Val Ile Gly Gly Ala Gly Asp Asp Val Phe Leu Gln Asp Leu Gly
                1060                1065                1070

Val Trp Ser Asn Gln Leu Asp Gly Gly Ala Gly Val Asp Thr Val Lys
            1075                1080                1085

Tyr Asn Val His Gln Pro Ser Glu Glu Arg Leu Glu Arg Met Gly Asp
    1090                1095                1100

Thr Gly Ile His Ala Asp Leu Gln Lys Gly Thr Val Glu Lys Trp Pro
1105                1110                1115                1120

Ala Leu Asn Leu Phe Ser Val Asp His Val Lys Asn Ile Glu Asn Leu
                1125                1130                1135

His Gly Ser Arg Leu Asn Asp Arg Ile Ala Gly Asp Asp Gln Asp Asn
```

-continued

```
                1140                1145                1150
    Glu Leu Trp Gly His Asp Gly Asn Asp Thr Ile Arg Gly Arg Gly Gly
                    1155                1160                1165

Asp Asp Ile Leu Arg Gly Gly Leu Gly Leu Asp Thr Leu Tyr Gly Glu
    1170                1175                1180

Asp Gly Asn Asp Ile Phe Leu Gln Asp Glu Thr Val Ser Asp Asp
    1185                1190                1195                1200

Ile Asp Gly Gly Ala Gly Leu Asp Thr Val Asp Tyr Ser Ala Met Ile
                    1205                1210                1215

His Pro Gly Arg Ile Val Ala Pro His Glu Tyr Gly Phe Gly Ile Glu
                    1220                1225                1230

Ala Asp Leu Ser Arg Glu Trp Val Arg Lys Ala Ser Ala Leu Gly Val
                    1235                1240                1245

Asp Tyr Tyr Asp Asn Val Arg Asn Val Glu Asn Val Ile Gly Thr Ser
                    1250                1255                1260

Met Lys Asp Val Leu Ile Gly Asp Ala Gln Ala Asn Thr Leu Met Gly
    1265                1270                1275                1280

Gln Gly Gly Asp Asp Thr Val Arg Gly Gly Asp Gly Asp Leu Leu
                    1285                1290                1295

Phe Gly Gly Asp Gly Asn Asp Met Leu Tyr Gly Asp Ala Gly Asn Asp
                    1300                1305                1310

Thr Leu Tyr Gly Gly Leu Gly Asp Asp Thr Leu Glu Gly Gly Ala Gly
                    1315                1320                1325

Asn Asp Trp Phe Gly Gln Thr Gln Ala Arg Glu His Asp Val Leu Arg
                    1330                1335                1340

Gly Gly Asp Gly Val Asp Thr Val Asp Tyr Ser Gln Thr Gly Ala His
    1345                1350                1355                1360

Ala Gly Ile Ala Ala Gly Arg Ile Gly Leu Gly Ile Leu Ala Asp Leu
                    1365                1370                1375

Gly Ala Gly Arg Val Asp Lys Leu Gly Glu Ala Gly Ser Ser Ala Tyr
                    1380                1385                1390

Asp Thr Val Ser Gly Ile Glu Asn Val Val Gly Thr Glu Leu Ala Asp
                    1395                1400                1405

Arg Ile Thr Gly Asp Ala Gln Ala Asn Val Leu Arg Gly Ala Gly Gly
                    1410                1415                1420

Ala Asp Val Leu Ala Gly Gly Glu Gly Asp Asp Val Leu Leu Gly Gly
    1425                1430                1435                1440

Asp Gly Asp Asp Gln Leu Ser Gly Asp Ala Gly Arg Asp Arg Leu Tyr
                    1445                1450                1455

Gly Glu Ala Gly Asp Asp Trp Phe Phe Gln Asp Ala Ala Asn Ala Gly
                    1460                1465                1470

Asn Leu Leu Asp Gly Gly Asp Gly Arg Asp Thr Val Asp Phe Ser Gly
                    1475                1480                1485

Pro Gly Arg Gly Leu Asp Ala Gly Ala Lys Gly Val Phe Leu Ser Leu
                    1490                1495                1500

Gly Lys Gly Phe Ala Ser Leu Met Asp Glu Pro Glu Thr Ser Asn Val
    1505                1510                1515                1520

Leu Arg Asn Ile Glu Asn Ala Val Gly Ser Ala Arg Asp Asp Val Leu
                    1525                1530                1535

Ile Gly Asp Ala Gly Ala Asn Val Leu Asn Gly Leu Ala Gly Asn Asp
                    1540                1545                1550

Val Leu Ser Gly Gly Ala Gly Asp Asp Val Leu Leu Gly Asp Glu Gly
                    1555                1560                1565
```

```
Ser Asp Leu Leu Ser Gly Asp Ala Gly Asn Asp Asp Leu Phe Gly Gly
    1570            1575                1580

Gln Gly Asp Asp Thr Tyr Leu Phe Gly Val Gly Tyr Gly His Asp Thr
1585            1590                1595                1600

Ile Tyr Glu Ser Gly Gly His Asp Thr Ile Arg Ile Asn Ala Gly
                1605                1610                1615

Ala Asp Gln Leu Trp Phe Ala Arg Gln Gly Asn Asp Leu Glu Ile Arg
            1620                1625                1630

Ile Leu Gly Thr Asp Asp Ala Leu Thr Val His Asp Trp Tyr Arg Asp
        1635                1640                1645

Ala Asp His Arg Val Glu Ile Ile His Ala Ala Asn Gln Ala Val Asp
    1650                1655                1660

Gln Ala Gly Ile Glu Lys Leu Val Glu Ala Met Ala Gln Tyr Pro Asp
1665            1670                1675                1680

Pro Gly Ala Ala Ala Ala Pro Pro Ala Ala Arg Val Pro Asp Thr
                1685                1690                1695

Leu Met Gln Ser Leu Ala Val Asn Trp Arg
            1700                1705

<210> SEQ ID NO 2
<211> LENGTH: 800
<212> TYPE: PRT
<213> ORGANISM: Bacillus anthracis

<400> SEQUENCE: 2

Met Thr Arg Asn Lys Phe Ile Pro Asn Lys Phe Ser Ile Ile Ser Phe
1               5                   10                  15

Ser Val Leu Leu Phe Ala Ile Ser Ser Ser Gln Ala Ile Glu Val Asn
                20                  25                  30

Ala Met Asn Glu His Tyr Thr Glu Ser Asp Ile Lys Arg Asn His Lys
            35                  40                  45

Thr Glu Lys Asn Lys Thr Glu Lys Glu Lys Phe Lys Asp Ser Ile Asn
    50                  55                  60

Asn Leu Val Lys Thr Glu Phe Thr Asn Glu Thr Leu Asp Lys Ile Gln
65                  70                  75                  80

Gln Thr Gln Asp Leu Leu Lys Lys Ile Pro Lys Asp Val Leu Glu Ile
                85                  90                  95

Tyr Ser Glu Leu Gly Gly Glu Ile Tyr Phe Thr Asp Ile Asp Leu Val
                100                 105                 110

Glu His Lys Glu Leu Gln Asp Leu Ser Glu Glu Glu Lys Asn Ser Met
            115                 120                 125

Asn Ser Arg Gly Glu Lys Val Pro Phe Ala Ser Arg Phe Val Phe Glu
        130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
                165                 170                 175

Ile Ser Leu Asp Ile Ile Ser Lys Asp Lys Ser Leu Asp Pro Glu Phe
            180                 185                 190

Leu Asn Leu Ile Lys Ser Leu Ser Asp Ser Asp Ser Ser Asp Leu
        195                 200                 205

Leu Phe Ser Gln Lys Phe Lys Glu Lys Leu Glu Leu Asn Asn Lys Ser
    210                 215                 220

Ile Asp Ile Asn Phe Ile Lys Glu Asn Leu Thr Glu Phe Gln His Ala
```

```
                225                 230                 235                 240
            Phe Ser Leu Ala Phe Ser Tyr Tyr Phe Ala Pro Asp His Arg Thr Val
                            245                 250                 255

Leu Glu Leu Tyr Ala Pro Asp Met Phe Glu Tyr Met Asn Lys Leu Glu
                            260                 265                 270

Lys Gly Gly Phe Glu Lys Ile Ser Glu Ser Leu Lys Lys Glu Gly Val
                            275                 280                 285

Glu Lys Asp Arg Ile Asp Val Leu Lys Gly Lys Ala Leu Lys Ala
            290                 295                 300

Ser Gly Leu Val Pro Glu His Ala Asp Ala Phe Lys Lys Ile Ala Arg
            305                 310                 315                 320

Glu Leu Asn Thr Tyr Ile Leu Phe Arg Pro Val Asn Lys Leu Ala Thr
                            325                 330                 335

Asn Leu Ile Lys Ser Gly Val Ala Thr Lys Gly Leu Asn Glu His Gly
                            340                 345                 350

Lys Ser Ser Asp Trp Gly Pro Val Ala Gly Tyr Ile Pro Phe Asp Gln
                            355                 360                 365

Asp Leu Ser Lys Lys His Gly Gln Gln Leu Ala Val Glu Lys Gly Asn
                            370                 375                 380

Leu Glu Asn Lys Lys Ser Ile Thr Glu His Glu Gly Glu Ile Gly Lys
            385                 390                 395                 400

Ile Pro Leu Lys Leu Asp His Leu Arg Ile Glu Glu Leu Lys Glu Asn
                            405                 410                 415

Gly Ile Ile Leu Lys Gly Lys Lys Glu Ile Asp Asn Gly Lys Lys Tyr
                            420                 425                 430

Tyr Leu Leu Glu Ser Asn Asn Gln Val Tyr Glu Phe Arg Ile Ser Asp
                            435                 440                 445

Glu Asn Asn Glu Val Gln Tyr Lys Thr Lys Glu Gly Lys Ile Thr Val
                            450                 455                 460

Leu Gly Glu Lys Phe Asn Trp Arg Asn Ile Glu Val Met Ala Lys Asn
            465                 470                 475                 480

Val Glu Gly Val Leu Lys Pro Leu Thr Ala Asp Tyr Asp Leu Phe Ala
                            485                 490                 495

Leu Ala Pro Ser Leu Thr Glu Ile Lys Lys Gln Ile Pro Thr Lys Arg
                            500                 505                 510

Met Asp Lys Val Val Asn Thr Pro Asn Ser Leu Glu Lys Gln Lys Gly
                            515                 520                 525

Val Thr Asn Leu Leu Ile Lys Tyr Gly Ile Glu Arg Lys Pro Asp Ser
                            530                 535                 540

Thr Lys Gly Thr Leu Ser Asn Trp Gln Lys Gln Met Leu Asp Arg Leu
            545                 550                 555                 560

Asn Glu Ala Val Lys Tyr Thr Gly Tyr Thr Gly Gly Asp Val Val Asn
                            565                 570                 575

His Gly Thr Glu Gln Asp Asn Glu Glu Phe Pro Glu Lys Asp Asn Glu
                            580                 585                 590

Ile Phe Ile Ile Asn Pro Glu Gly Glu Phe Ile Leu Thr Lys Asn Trp
                            595                 600                 605

Glu Met Thr Gly Arg Phe Ile Glu Lys Asn Ile Thr Gly Lys Asp Tyr
                            610                 615                 620

Leu Tyr Tyr Phe Asn Arg Ser Tyr Asn Lys Ile Ala Pro Gly Asn Lys
            625                 630                 635                 640

Ala Tyr Ile Glu Trp Thr Asp Pro Ile Thr Lys Ala Lys Ile Asn Thr
                            645                 650                 655
```

-continued

```
Ile Pro Thr Ser Ala Glu Phe Ile Lys Asn Leu Ser Ser Ile Arg Arg
            660                 665                 670

Ser Ser Asn Val Gly Val Tyr Lys Asp Ser Gly Asp Lys Asp Glu Phe
        675                 680                 685

Ala Lys Lys Glu Ser Val Lys Lys Ile Ala Gly Tyr Leu Ser Asp Tyr
    690                 695                 700

Tyr Asn Ser Ala Asn His Ile Phe Ser Gln Glu Lys Lys Arg Lys Ile
705                 710                 715                 720

Ser Ile Phe Arg Gly Ile Gln Ala Tyr Asn Glu Ile Glu Asn Val Leu
                725                 730                 735

Lys Ser Lys Gln Ile Ala Pro Glu Tyr Lys Asn Tyr Phe Gln Tyr Leu
            740                 745                 750

Lys Glu Arg Ile Thr Asn Gln Val Gln Leu Leu Leu Thr His Gln Lys
        755                 760                 765

Ser Asn Ile Glu Phe Lys Leu Leu Tyr Lys Gln Leu Asn Phe Thr Glu
    770                 775                 780

Asn Glu Thr Asp Asn Phe Glu Val Phe Gln Lys Ile Ile Asp Glu Lys
785                 790                 795                 800

<210> SEQ ID NO 3
<211> LENGTH: 800
<212> TYPE: PRT
<213> ORGANISM: Artificial Sequence
<220> FEATURE:
<223> OTHER INFORMATION: A synthetic adenylate cyclase.

<400> SEQUENCE: 3

Met Thr Arg Asn Lys Phe Ile Pro Asn Lys Phe Ser Ile Ile Ser Phe
1               5                   10                  15

Ser Val Leu Leu Phe Ala Ile Ser Ser Gln Ala Ile Glu Val Asn
            20                  25                  30

Ala Met Asn Glu His Tyr Thr Glu Ser Asp Ile Lys Arg Asn His Lys
        35                  40                  45

Thr Glu Lys Asn Lys Thr Glu Lys Glu Lys Phe Lys Asp Ser Ile Asn
    50                  55                  60

Asn Leu Val Lys Thr Glu Phe Thr Asn Glu Thr Leu Asp Lys Ile Gln
65                  70                  75                  80

Gln Thr Gln Asp Leu Leu Lys Lys Ile Pro Lys Asp Val Leu Glu Ile
                85                  90                  95

Tyr Ser Glu Leu Gly Gly Glu Ile Tyr Phe Thr Asp Ile Asp Leu Val
            100                 105                 110

Glu His Lys Glu Leu Gln Asp Leu Ser Glu Glu Lys Asn Ser Met
        115                 120                 125

Asn Ser Arg Gly Glu Lys Val Pro Phe Ala Ser Arg Phe Val Phe Glu
    130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
                165                 170                 175

Ile Ser Leu Asp Ile Ile Ser Lys Asp Lys Ser Leu Asp Pro Glu Phe
            180                 185                 190

Leu Asn Leu Ile Lys Ser Leu Ser Asp Asp Ser Asp Ser Ser Asp Leu
        195                 200                 205

Leu Phe Ser Gln Lys Phe Lys Glu Lys Leu Glu Leu Asn Asn Lys Ser
    210                 215                 220
```

-continued

Ile Asp Ile Asn Phe Ile Lys Glu Asn Leu Thr Glu Phe Gln His Ala
225                 230                 235                 240

Phe Ser Leu Ala Phe Ser Tyr Tyr Phe Ala Pro Asp His Arg Thr Val
                245                 250                 255

Leu Glu Leu Tyr Ala Pro Asp Met Phe Glu Tyr Met Asn Lys Leu Glu
            260                 265                 270

Lys Gly Gly Phe Glu Lys Ile Ser Glu Ser Leu Lys Lys Glu Gly Val
        275                 280                 285

Glu Lys Asp Arg Ile Asp Val Leu Lys Gly Glu Lys Ala Leu Lys Ala
    290                 295                 300

Ser Gly Leu Val Pro Glu His Ala Asp Ala Phe Lys Lys Ile Ala Arg
305                 310                 315                 320

Glu Leu Asn Thr Tyr Ile Leu Phe Arg Pro Val Asn Lys Leu Ala Thr
                325                 330                 335

Asn Leu Ile Lys Ser Gly Val Ala Thr Lys Gly Leu Asn Val His Gly
            340                 345                 350

Lys Ser Ser Asp Trp Gly Pro Val Ala Gly Tyr Ile Pro Phe Asp Gln
        355                 360                 365

Asp Leu Ser Lys Lys His Gly Gln Gln Leu Ala Val Glu Lys Gly Asn
    370                 375                 380

Leu Glu Asn Lys Lys Ser Ile Thr Glu His Glu Gly Glu Ile Gly Lys
385                 390                 395                 400

Ile Pro Leu Lys Leu Asp His Leu Arg Ile Glu Glu Leu Lys Glu Asn
                405                 410                 415

Gly Ile Ile Leu Lys Gly Lys Lys Glu Ile Asp Asn Gly Lys Lys Tyr
            420                 425                 430

Tyr Leu Leu Glu Ser Asn Asn Gln Val Tyr Glu Phe Arg Ile Ser Asp
        435                 440                 445

Glu Asn Asn Glu Val Gln Tyr Lys Thr Lys Glu Gly Lys Ile Thr Val
    450                 455                 460

Leu Gly Glu Lys Phe Asn Trp Arg Asn Ile Glu Val Met Ala Lys Asn
465                 470                 475                 480

Val Glu Gly Val Leu Lys Pro Leu Thr Ala Asp Tyr Asp Leu Phe Ala
                485                 490                 495

Leu Ala Pro Ser Leu Thr Glu Ile Lys Lys Gln Ile Pro Gln Lys Glu
            500                 505                 510

Trp Asp Lys Val Val Asn Thr Pro Asn Ser Leu Glu Lys Gln Lys Gly
        515                 520                 525

Val Thr Asn Leu Leu Ile Lys Tyr Gly Ile Glu Arg Lys Pro Asp Ser
    530                 535                 540

Thr Lys Gly Thr Leu Ser Asn Trp Gln Lys Gln Met Leu Asp Arg Leu
545                 550                 555                 560

Asn Glu Ala Val Lys Tyr Thr Gly Tyr Thr Gly Gly Asp Val Val Asn
                565                 570                 575

His Gly Thr Glu Gln Asp Asn Glu Glu Phe Pro Glu Lys Asp Asn Glu
            580                 585                 590

Ile Phe Ile Ile Asn Pro Glu Gly Glu Phe Ile Leu Thr Lys Asn Trp
        595                 600                 605

Glu Met Thr Gly Arg Phe Ile Glu Lys Asn Ile Thr Gly Lys Asp Tyr
    610                 615                 620

Leu Tyr Tyr Phe Asn Arg Ser Tyr Asn Lys Ile Ala Pro Gly Asn Lys
625                 630                 635                 640

```
Ala Tyr Ile Glu Trp Thr Asp Pro Ile Thr Lys Ala Lys Ile Asn Thr
                645                 650                 655

Ile Pro Thr Ser Ala Glu Phe Ile Lys Asn Leu Ser Ser Ile Arg Arg
            660                 665                 670

Ser Ser Asn Val Gly Val Tyr Lys Asp Ser Gly Asp Lys Asp Glu Phe
            675                 680                 685

Ala Lys Lys Glu Ser Val Lys Lys Ile Ala Gly Tyr Leu Ser Asp Tyr
            690                 695                 700

Tyr Asn Ser Ala Asn His Ile Phe Ser Gln Glu Lys Lys Arg Lys Ile
705                 710                 715                 720

Ser Ile Phe Arg Gly Ile Gln Ala Tyr Asn Glu Ile Glu Asn Val Leu
                725                 730                 735

Lys Ser Lys Gln Ile Ala Pro Glu Tyr Lys Asn Tyr Phe Gln Tyr Leu
            740                 745                 750

Lys Glu Arg Ile Thr Asn Gln Val Gln Leu Leu Thr His Gln Lys
            755                 760                 765

Ser Asn Ile Glu Phe Lys Leu Leu Tyr Lys Gln Leu Asn Phe Thr Glu
770                 775                 780

Asn Glu Thr Asp Asn Phe Glu Val Phe Gln Lys Ile Ile Asp Glu Lys
785                 790                 795                 800

<210> SEQ ID NO 4
<211> LENGTH: 800
<212> TYPE: PRT
<213> ORGANISM: Artificial Sequence
<220> FEATURE:
<223> OTHER INFORMATION: A synthetic adenylate cyclase.

<400> SEQUENCE: 4

Met Thr Arg Asn Lys Phe Ile Pro Asn Lys Phe Ser Ile Ile Ser Phe
1               5                   10                  15

Ser Val Leu Leu Phe Ala Ile Ser Ser Ser Gln Ala Ile Glu Val Asn
            20                  25                  30

Ala Met Asn Glu His Tyr Thr Glu Ser Asp Ile Lys Arg Asn His Lys
            35                  40                  45

Thr Glu Lys Asn Lys Thr Glu Lys Glu Lys Phe Lys Asp Ser Ile Asn
    50                  55                  60

Asn Leu Val Lys Thr Glu Phe Thr Asn Glu Thr Leu Asp Lys Ile Gln
65                  70                  75                  80

Gln Thr Gln Asp Leu Leu Lys Lys Ile Pro Lys Asp Val Leu Glu Ile
                85                  90                  95

Tyr Ser Glu Leu Gly Gly Glu Ile Tyr Phe Thr Asp Ile Asp Leu Val
            100                 105                 110

Glu His Lys Glu Leu Gln Asp Leu Ser Glu Glu Lys Asn Ser Met
            115                 120                 125

Asn Ser Arg Gly Glu Lys Val Pro Phe Ala Ser Arg Phe Val Phe Glu
130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
                165                 170                 175

Ile Ser Leu Asp Ile Ile Ser Lys Asp Lys Ser Leu Asp Pro Glu Phe
            180                 185                 190

Leu Asn Leu Ile Lys Ser Leu Ser Asp Asp Ser Asp Ser Ser Asp Leu
            195                 200                 205
```

```
Leu Phe Ser Gln Lys Phe Lys Glu Lys Leu Glu Leu Asn Asn Lys Ser
    210                 215                 220

Ile Asp Ile Asn Phe Ile Lys Glu Asn Leu Thr Glu Phe Gln His Ala
225                 230                 235                 240

Phe Ser Leu Ala Phe Ser Tyr Tyr Phe Ala Pro Asp His Arg Thr Val
                245                 250                 255

Leu Glu Leu Tyr Ala Pro Asp Met Phe Glu Tyr Met Asn Lys Leu Glu
            260                 265                 270

Lys Gly Gly Phe Glu Lys Ile Ser Glu Ser Leu Lys Lys Glu Gly Val
        275                 280                 285

Glu Lys Asp Arg Ile Asp Val Leu Lys Gly Lys Ala Leu Lys Ala
    290                 295                 300

Ser Gly Leu Val Pro Glu His Ala Asp Ala Phe Lys Lys Ile Ala Arg
305                 310                 315                 320

Glu Leu Asn Thr Tyr Ile Leu Phe Arg Pro Val Asn Lys Leu Ala Thr
                325                 330                 335

Asn Leu Ile Lys Ser Gly Val Ala Thr Lys Gly Leu Asn Val His Gly
            340                 345                 350

Lys Ser Ser Asp Trp Gly Pro Val Ala Gly Tyr Ile Pro Phe Asp Gln
        355                 360                 365

Asp Leu Ser Lys Lys His Gly Gln Gln Leu Ala Val Glu Lys Gly Asn
    370                 375                 380

Leu Glu Asn Lys Lys Ser Ile Thr Glu His Glu Gly Glu Ile Gly Lys
385                 390                 395                 400

Ile Pro Leu Lys Leu Asp His Leu Arg Ile Glu Glu Leu Lys Glu Asn
                405                 410                 415

Gly Ile Ile Leu Lys Gly Lys Lys Glu Ile Asp Asn Gly Lys Lys Tyr
            420                 425                 430

Tyr Leu Leu Glu Ser Asn Asn Gln Val Tyr Glu Phe Arg Ile Ser Asp
        435                 440                 445

Glu Asn Asn Glu Val Gln Tyr Lys Thr Lys Glu Gly Lys Ile Thr Val
    450                 455                 460

Leu Gly Glu Lys Phe Asn Trp Arg Asn Ile Glu Val Met Ala Lys Asn
465                 470                 475                 480

Val Glu Gly Val Leu Lys Pro Leu Thr Ala Asp Tyr Asp Leu Phe Ala
                485                 490                 495

Leu Ala Pro Ser Leu Thr Glu Ile Lys Lys Gln Ile Pro Gln Lys Glu
            500                 505                 510

Trp Asp Lys Val Val Asn Thr Pro Asn Ser Leu Glu Lys Gln Lys Gly
        515                 520                 525

Val Thr Asn Leu Leu Ile Lys Tyr Gly Ile Glu Arg Lys Pro Asp Ser
    530                 535                 540

Thr Lys Gly Thr Leu Ser Asn Trp Gln Lys Gln Met Leu Asp Arg Leu
545                 550                 555                 560

Asn Glu Ala Val Lys Tyr Thr Gly Tyr Thr Gly Gly Asp Val Val Asn
                565                 570                 575

His Gly Thr Glu Gln Asp Asn Glu Glu Phe Pro Glu Lys Asp Asn Glu
            580                 585                 590

Ile Phe Ile Ile Asn Pro Glu Gly Glu Phe Ile Leu Thr Lys Asn Trp
        595                 600                 605

Glu Met Thr Gly Arg Phe Ile Glu Lys Asn Ile Thr Gly Lys Asp Tyr
    610                 615                 620

Leu Tyr Tyr Phe Asn Arg Ser Tyr Asn Lys Ile Ala Pro Gly Asn Lys
```

```
            625                 630                 635                 640
Ala Tyr Ile Glu Trp Thr Asp Pro Ile Thr Lys Ala Lys Ile Asn Thr
                        645                 650                 655

Ile Pro Thr Ser Ala Glu Phe Ile Lys Asn Leu Ser Ser Ile Arg Arg
                660                 665                 670

Ser Ser Asn Val Gly Val Tyr Lys Asp Ser Gly Asp Lys Asp Glu Phe
            675                 680                 685

Ala Lys Lys Glu Ser Val Lys Lys Ile Ala Gly Tyr Leu Ser Asp Tyr
        690                 695                 700

Tyr Asn Ser Ala Asn His Ile Phe Ser Gln Glu Lys Lys Arg Lys Ile
705                 710                 715                 720

Ser Ile Phe Arg Gly Ile Gln Ala Tyr Asn Glu Ile Glu Asn Val Leu
                725                 730                 735

Lys Ser Lys Gln Ile Ala Pro Glu Tyr Lys Asn Tyr Phe Gln Tyr Leu
                740                 745                 750

Lys Glu Arg Ile Thr Asn Gln Val Gln Leu Leu Thr His Gln Lys
            755                 760                 765

Ser Asn Ile Glu Phe Lys Leu Leu Tyr Lys Gln Leu Asn Phe Thr Glu
        770                 775                 780

Asn Glu Thr Asp Asn Phe Glu Val Phe Gln Lys Ile Ile Asp Glu Lys
785                 790                 795                 800

<210> SEQ ID NO 5
<211> LENGTH: 433
<212> TYPE: PRT
<213> ORGANISM: Artificial Sequence
<220> FEATURE:
<223> OTHER INFORMATION: A synthetic adenylate cyclase.

<400> SEQUENCE: 5

Met Ala Gln Glu Ile Glu Leu Lys Phe Ile Val Asn His Ser Ala Val
1               5                   10                  15

Glu Ala Leu Arg Asp His Leu Asn Thr Leu Gly Gly Glu His His Asp
            20                  25                  30

Pro Val Gln Leu Leu Asn Ile Tyr Tyr Glu Thr Pro Asp Asn Trp Leu
        35                  40                  45

Arg Gly His Asp Met Gly Leu Arg Ile Arg Gly Glu Asn Gly Arg Tyr
    50                  55                  60

Glu Met Thr Met Lys Val Ala Gly Arg Val Thr Gly Gly Leu His Gln
65                  70                  75                  80

Arg Pro Glu Tyr Asn Val Ala Leu Ser Glu Pro Thr Leu Asp Leu Ala
                85                  90                  95

Gln Leu Pro Thr Glu Val Trp Pro Asn Gly Glu Leu Pro Ala Asp Leu
            100                 105                 110

Ala Ser Arg Val Gln Pro Leu Phe Ser Thr Asp Phe Tyr Arg Glu Lys
        115                 120                 125

Trp Leu Val Ala Val Asp Gly Ser Gln Ile Glu Ile Ala Leu Asp Gln
    130                 135                 140

Gly Glu Val Lys Ala Gly Glu Phe Ala Glu Pro Ile Cys Glu Leu Glu
145                 150                 155                 160

Leu Glu Leu Leu Ser Gly Asp Thr Arg Ala Val Leu Lys Leu Ala Asn
                165                 170                 175

Gln Leu Val Ser Gln Thr Gly Leu Arg Gln Gly Ser Leu Ser Lys Ala
            180                 185                 190

Ala Arg Gly Tyr His Leu Ala Gln Gly Asn Pro Ala Arg Glu Ile Lys
```

```
                195                 200                 205
Pro Thr Thr Ile Leu His Val Ala Ala Lys Ala Asp Val Glu Gln Gly
210                 215                 220

Leu Glu Ala Ala Leu Glu Leu Ala Leu Ala Gln Trp Gln Tyr His Glu
225                 230                 235                 240

Glu Leu Trp Val Arg Gly Asn Asp Ala Lys Glu Gln Val Leu Ala
            245                 250                 255

Ala Ile Ser Leu Val Arg His Thr Leu Met Leu Phe Gly Gly Ile Val
            260                 265                 270

Pro Arg Lys Ala Ser Thr His Leu Arg Asp Leu Leu Thr Gln Cys Glu
            275                 280                 285

Ala Thr Ile Ala Ser Ala Val Ser Ala Val Thr Ala Val Tyr Ser Thr
290                 295                 300

Glu Thr Ala Met Ala Lys Leu Ala Leu Thr Glu Trp Leu Val Ser Lys
305                 310                 315                 320

Ala Trp Gln Pro Phe Leu Asp Ala Lys Ala Gln Gly Lys Ile Ser Asp
            325                 330                 335

Ser Phe Lys Arg Phe Ala Asp Ile His Leu Ser Arg His Ala Ala Glu
            340                 345                 350

Leu Lys Ser Val Phe Cys Gln Pro Leu Gly Asp Arg Tyr Arg Asp Gln
            355                 360                 365

Leu Pro Arg Leu Thr Arg Asp Ile Asp Ser Ile Leu Leu Leu Ala Gly
            370                 375                 380

Tyr Tyr Asp Pro Val Val Ala Gln Ala Trp Leu Glu Asn Trp Gln Gly
385                 390                 395                 400

Leu His His Ala Ile Ala Thr Gly Gln Arg Ile Glu Ile Glu His Phe
            405                 410                 415

Arg Asn Glu Ala Asn Asn Gln Glu Pro Phe Trp Leu His Ser Gly Lys
            420                 425                 430

Arg

<210> SEQ ID NO 6
<211> LENGTH: 1706
<212> TYPE: PRT
<213> ORGANISM: Bordetella pertussis

<400> SEQUENCE: 6

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
```

```
              130                 135                 140
Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
            195                 200                 205

Val Thr Ser Gly Asp Ser Val Thr Asp Tyr Leu Ala Arg Thr Arg Arg
        210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Gln His Gly Thr Glu Gln Asn Asn
        290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
        370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
        435                 440                 445

Pro Gly Val Ser Gly Ala Ser His Trp Gly Gln Arg Ala Leu Gln
        450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
                485                 490                 495

Ala Ala Ser Leu Ser Ala Ala Val Phe Gly Leu Gly Glu Ala Ser Ser
            500                 505                 510

Ala Val Ala Glu Thr Val Ser Gly Phe Arg Gly Ser Ser Arg Trp
        515                 520                 525

Ala Gly Gly Phe Gly Val Ala Gly Gly Ala Met Ala Leu Gly Gly
        530                 535                 540

Ile Ala Ala Ala Val Gly Ala Gly Met Ser Leu Thr Asp Asp Ala Pro
545                 550                 555                 560
```

```
Ala Gly Gln Lys Ala Ala Gly Ala Glu Ile Ala Leu Gln Leu Thr
            565                 570                 575
Gly Gly Thr Val Glu Leu Ala Ser Ser Ile Ala Leu Ala Leu Ala Ala
        580                 585                 590
Ala Arg Gly Val Thr Ser Gly Leu Gln Val Ala Gly Ala Ser Ala Gly
        595                 600                 605
Ala Ala Ala Gly Ala Leu Ala Ala Leu Ser Pro Met Glu Ile Tyr
610                 615                 620
Gly Leu Val Gln Gln Ser His Tyr Ala Asp Gln Leu Asp Lys Leu Ala
625                 630                 635                 640
Gln Glu Ser Ser Ala Tyr Gly Tyr Glu Gly Asp Ala Leu Leu Ala Gln
                645                 650                 655
Leu Tyr Arg Asp Lys Thr Ala Ala Glu Gly Ala Val Ala Gly Val Ser
            660                 665                 670
Ala Val Leu Ser Thr Val Gly Ala Ala Val Ser Ile Ala Ala Ala Ala
        675                 680                 685
Ser Val Val Gly Ala Pro Val Ala Val Thr Ser Leu Leu Thr Gly
    690                 695                 700
Ala Leu Asn Gly Ile Leu Arg Gly Val Gln Gln Pro Ile Ile Glu Lys
705                 710                 715                 720
Leu Ala Asn Asp Tyr Ala Arg Lys Ile Asp Glu Leu Gly Gly Pro Gln
                725                 730                 735
Ala Tyr Phe Glu Lys Asn Leu Gln Ala Arg His Glu Gln Leu Ala Asn
            740                 745                 750
Ser Asp Gly Leu Arg Lys Met Leu Ala Asp Leu Gln Ala Gly Trp Asn
        755                 760                 765
Ala Ser Ser Val Ile Gly Val Gln Thr Thr Glu Ile Ser Lys Ser Ala
    770                 775                 780
Leu Glu Leu Ala Ala Ile Thr Gly Asn Ala Asp Asn Leu Lys Ser Val
785                 790                 795                 800
Asp Val Phe Val Asp Arg Phe Val Gln Gly Glu Arg Val Ala Gly Gln
                805                 810                 815
Pro Val Val Leu Asp Val Ala Ala Gly Gly Ile Asp Ile Ala Ser Arg
            820                 825                 830
Lys Gly Glu Arg Pro Ala Leu Thr Phe Ile Thr Pro Leu Ala Ala Pro
        835                 840                 845
Gly Glu Glu Gln Arg Arg Thr Lys Thr Gly Lys Ser Glu Phe Thr
    850                 855                 860
Thr Phe Val Glu Ile Val Gly Lys Gln Asp Arg Trp Arg Ile Arg Asp
865                 870                 875                 880
Gly Ala Ala Asp Thr Thr Ile Asp Leu Ala Lys Val Val Ser Gln Leu
                885                 890                 895
Val Asp Ala Asn Gly Val Leu Lys His Ser Ile Lys Leu Asp Val Ile
            900                 905                 910
Gly Gly Asp Gly Asp Val Leu Ala Asn Ala Ser Arg Ile His
        915                 920                 925
Tyr Asp Gly Gly Ala Gly Thr Asn Thr Val Ser Tyr Ala Ala Leu Gly
    930                 935                 940
Arg Gln Asp Ser Ile Thr Val Ser Ala Asp Gly Glu Arg Phe Asn Val
945                 950                 955                 960
Arg Lys Gln Leu Asn Asn Ala Asn Val Tyr Arg Glu Gly Val Ala Thr
                965                 970                 975
```

-continued

Gln Thr Thr Ala Tyr Gly Lys Arg Thr Glu Asn Val Gln Tyr Arg His
              980                 985                 990

Val Glu Leu Ala Arg Val Gly Gln Leu Val Glu Val Asp Thr Leu Glu
        995                1000                1005

His Val Gln His Ile Ile Gly Gly Ala Gly Asn Asp Ser Ile Thr Gly
    1010                1015                1020

Asn Ala His Asp Asn Phe Leu Ala Gly Gly Ser Gly Asp Asp Arg Leu
1025                1030                1035                1040

Asp Gly Gly Ala Gly Asn Asp Thr Leu Val Gly Gly Glu Gly Gln Asn
                1045                1050                1055

Thr Val Ile Gly Gly Ala Gly Asp Asp Val Phe Leu Gln Asp Leu Gly
            1060                1065                1070

Val Trp Ser Asn Gln Leu Asp Gly Gly Ala Gly Val Asp Thr Val Lys
        1075                1080                1085

Tyr Asn Val His Gln Pro Ser Glu Glu Arg Leu Glu Arg Met Gly Asp
    1090                1095                1100

Thr Gly Ile His Ala Asp Leu Gln Lys Gly Thr Val Glu Lys Trp Pro
1105                1110                1115                1120

Ala Leu Asn Leu Phe Ser Val Asp His Val Lys Asn Ile Glu Asn Leu
                1125                1130                1135

His Gly Ser Arg Leu Asn Asp Arg Ile Ala Gly Asp Asp Gln Asp Asn
            1140                1145                1150

Glu Leu Trp Gly His Asp Gly Asn Asp Thr Ile Arg Gly Arg Gly Gly
        1155                1160                1165

Asp Asp Ile Leu Arg Gly Gly Leu Gly Leu Asp Thr Leu Tyr Gly Glu
    1170                1175                1180

Asp Gly Asn Asp Ile Phe Leu Gln Asp Asp Glu Thr Val Ser Asp Asp
1185                1190                1195                1200

Ile Asp Gly Gly Ala Gly Leu Asp Thr Val Asp Tyr Ser Ala Met Ile
                1205                1210                1215

His Pro Gly Arg Ile Val Ala Pro His Glu Tyr Gly Phe Gly Ile Glu
            1220                1225                1230

Ala Asp Leu Ser Arg Glu Trp Val Arg Lys Ala Ser Ala Leu Gly Val
        1235                1240                1245

Asp Tyr Tyr Asp Asn Val Arg Asn Val Glu Asn Val Ile Gly Thr Ser
    1250                1255                1260

Met Lys Asp Val Leu Ile Gly Asp Ala Gln Ala Asn Thr Leu Met Gly
1265                1270                1275                1280

Gln Gly Gly Asp Asp Thr Val Arg Gly Gly Asp Gly Asp Asp Leu Leu
                1285                1290                1295

Phe Gly Gly Asp Gly Asn Asp Met Leu Tyr Gly Asp Ala Gly Asn Asp
            1300                1305                1310

Thr Leu Tyr Gly Gly Leu Gly Asp Asp Thr Leu Glu Gly Gly Ala Gly
        1315                1320                1325

Asn Asp Trp Phe Gly Gln Thr Gln Ala Arg Glu His Asp Val Leu Arg
    1330                1335                1340

Gly Gly Asp Gly Val Asp Thr Val Asp Tyr Ser Gln Thr Gly Ala His
1345                1350                1355                1360

Ala Gly Ile Ala Ala Gly Arg Ile Gly Leu Gly Ile Leu Ala Asp Leu
                1365                1370                1375

Gly Ala Gly Arg Val Asp Lys Leu Gly Glu Ala Gly Ser Ser Ala Tyr
            1380                1385                1390

Asp Thr Val Ser Gly Ile Glu Asn Val Val Gly Thr Glu Leu Ala Asp

```
                1395                1400                1405
Arg Ile Thr Gly Asp Ala Gln Ala Asn Val Leu Arg Gly Ala Gly Gly
            1410                1415                1420

Ala Asp Val Leu Ala Gly Gly Glu Gly Asp Asp Val Leu Leu Gly Gly
1425                1430                1435                1440

Asp Gly Asp Asp Gln Leu Ser Gly Asp Ala Gly Arg Asp Arg Leu Tyr
                1445                1450                1455

Gly Glu Ala Gly Asp Asp Trp Phe Phe Gln Asp Ala Asn Ala Gly
1460                1465                1470

Asn Leu Leu Asp Gly Gly Asp Gly Arg Asp Thr Val Asp Phe Ser Gly
                1475                1480                1485

Pro Gly Arg Gly Leu Asp Ala Gly Ala Lys Gly Val Phe Leu Ser Leu
            1490                1495                1500

Gly Lys Gly Phe Ala Ser Leu Met Asp Glu Pro Glu Thr Ser Asn Val
1505                1510                1515                1520

Leu Arg Asn Ile Glu Asn Ala Val Gly Ser Ala Arg Asp Asp Val Leu
                1525                1530                1535

Ile Gly Asp Ala Gly Ala Asn Val Leu Asn Gly Leu Ala Gly Asn Asp
            1540                1545                1550

Val Leu Ser Gly Gly Ala Gly Asp Asp Val Leu Leu Gly Asp Glu Gly
            1555                1560                1565

Ser Asp Leu Leu Ser Gly Asp Ala Gly Asn Asp Asp Leu Phe Gly Gly
            1570                1575                1580

Gln Gly Asp Asp Thr Tyr Leu Phe Gly Val Gly Tyr Gly His Asp Thr
1585                1590                1595                1600

Ile Tyr Glu Ser Gly Gly Gly His Asp Thr Ile Arg Ile Asn Ala Gly
                1605                1610                1615

Ala Asp Gln Leu Trp Phe Ala Arg Gln Gly Asn Asp Leu Glu Ile Arg
            1620                1625                1630

Ile Leu Gly Thr Asp Asp Ala Leu Thr Val His Asp Trp Tyr Arg Asp
            1635                1640                1645

Ala Asp His Arg Val Glu Ile Ile His Ala Ala Asn Gln Ala Val Asp
            1650                1655                1660

Gln Ala Gly Ile Glu Lys Leu Val Glu Ala Met Ala Gln Tyr Pro Asp
1665                1670                1675                1680

Pro Gly Ala Ala Ala Ala Pro Pro Ala Ala Arg Val Pro Asp Thr
                1685                1690                1695

Leu Met Gln Ser Leu Ala Val Asn Trp Arg
            1700                1705

<210> SEQ ID NO 7
<211> LENGTH: 1706
<212> TYPE: PRT
<213> ORGANISM: Bordetella bronchiseptica

<400> SEQUENCE: 7

Met Gln Gln Ser His Gln Ala Gly Tyr Ala Asn Ala Ala Asp Arg Glu
 1               5                  10                  15

Ser Gly Ile Pro Ala Ala Val Leu Asp Gly Ile Lys Ala Val Ala Lys
                20                  25                  30

Glu Lys Asn Ala Thr Leu Met Phe Arg Leu Val Asn Pro His Ser Thr
            35                  40                  45

Ser Leu Ile Ala Glu Gly Val Ala Thr Lys Gly Leu Gly Val His Ala
        50                  55                  60
```

```
Lys Ser Ser Asp Trp Gly Leu Gln Ala Gly Tyr Ile Pro Val Asn Pro
 65                  70                  75                  80

Asn Leu Ser Lys Leu Phe Gly Arg Ala Pro Glu Val Ile Ala Arg Ala
             85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
        130                 135                 140

Glu Gln Phe Glu Phe Arg Val Lys Thr Ser Asp Gly Arg Tyr Ala
145                 150                 155                 160

Val Gln Tyr Arg Arg Lys Gly Gly Asp Phe Glu Ala Val Lys Val
            165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
            245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
            325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Gly Gly Arg Ser Lys Ser Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
            405                 410                 415

Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
        435                 440                 445

Pro Gly Val Ser Gly Ala Ser Ala His Trp Gly Gln Arg Ala Leu Gln
    450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
```

```
                    485             490              495
Ala Ala Ser Leu Ser Ala Ala Val Phe Gly Leu Gly Glu Ala Ser Ser
                500             505             510

Ala Val Ala Glu Thr Val Ser Gly Phe Phe Arg Gly Ser Ser Arg Trp
                515             520             525

Ala Gly Gly Phe Gly Val Ala Gly Gly Ala Met Ala Leu Gly Gly Gly
                530             535             540

Ile Ala Ala Ala Val Gly Ala Gly Met Ser Leu Thr Asp Asp Ala Pro
545                 550             555             560

Ala Gly Gln Lys Ala Ala Gly Ala Glu Ile Ala Leu Gln Leu Thr
                565             570             575

Gly Gly Thr Val Glu Leu Ala Ser Ser Ile Ala Leu Ala Leu Ala Ala
                580             585             590

Ala Arg Gly Val Thr Ser Gly Leu Gln Val Ala Gly Ala Ser Ala Gly
                595             600             605

Ala Ala Ala Gly Ala Leu Ala Ala Leu Ser Pro Met Glu Ile Tyr
                610             615             620

Gly Leu Val Gln Gln Ser His Tyr Ala Asp Gln Leu Asp Lys Leu Ala
625                 630             635             640

Gln Glu Ser Ser Ala Tyr Gly Tyr Glu Gly Asp Ala Leu Leu Ala Gln
                645             650             655

Leu Tyr Arg Asp Lys Thr Ala Ala Glu Gly Ala Val Ala Gly Val Ser
                660             665             670

Ala Val Leu Ser Thr Val Gly Ala Ala Val Ser Ile Ala Ala Ala Ala
                675             680             685

Ser Val Val Gly Ala Pro Val Ala Val Thr Ser Leu Leu Thr Gly
                690             695             700

Ala Leu Asn Gly Ile Leu Arg Gly Val Gln Gln Pro Ile Ile Glu Lys
705                 710             715             720

Leu Ala Asn Asp Tyr Ala Arg Lys Ile Asp Glu Leu Gly Gly Pro Gln
                725             730             735

Ala Tyr Phe Glu Lys Asn Leu Gln Ala Arg His Glu Gln Leu Ala Asn
                740             745             750

Ser Asp Gly Leu Arg Lys Met Leu Ala Asp Leu Gln Ala Gly Trp Asn
                755             760             765

Ala Ser Ser Val Ile Gly Val Gln Thr Thr Glu Ile Ser Lys Ser Ala
                770             775             780

Leu Glu Leu Ala Ala Ile Thr Gly Asn Ala Asp Asn Leu Lys Ser Ala
785                 790             795             800

Asp Val Phe Val Asp Arg Phe Ile Gln Gly Glu Arg Val Ala Gly Gln
                805             810             815

Pro Val Val Leu Asp Val Ala Ala Gly Gly Ile Asp Ile Ala Ser Arg
                820             825             830

Lys Gly Glu Arg Pro Ala Leu Thr Phe Ile Thr Pro Leu Ala Ala Pro
                835             840             845

Gly Glu Glu Gln Arg Arg Thr Lys Thr Gly Lys Ser Glu Phe Thr
                850             855             860

Thr Phe Val Glu Ile Val Gly Lys Gln Asp Arg Trp Arg Ile Arg Asp
865                 870             875             880

Gly Ala Ala Asp Thr Thr Ile Asp Leu Ala Lys Val Val Ser Gln Leu
                885             890             895

Val Asp Ala Asn Gly Val Leu Lys His Ser Ile Lys Leu Glu Val Ile
                900             905             910
```

```
Gly Gly Asp Gly Asp Val Val Leu Ala Asn Ala Ser Arg Ile His
        915                 920                 925

Tyr Asp Gly Gly Ala Gly Thr Asn Thr Val Ser Tyr Ala Ala Leu Gly
    930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Lys Thr Ala Tyr Gly Lys Arg Thr Glu Asn Val Gln Tyr Arg His
                980                 985                 990

Val Glu Leu Ala Arg Val Gly Gln Leu Val Gln Val Asp Thr Leu Glu
                995                1000                1005

His Val Gln His Ile Ile Gly Gly Ala Gly Asn Asp Ser Ile Thr Gly
        1010                1015                1020

Asn Ala His Asp Asn Phe Leu Ala Gly Gly Ala Gly Asp Asp Arg Leu
1025                1030                1035                1040

Asp Gly Gly Ala Gly Asn Asp Thr Leu Val Gly Gly Glu Gly His Asn
            1045                1050                1055

Thr Val Val Gly Gly Ala Gly Asp Asp Val Phe Leu Gly Asp Leu Gly
        1060                1065                1070

Val Trp Ser Asn Gln Leu Asp Gly Gly Ala Gly Val Asp Thr Val Lys
        1075                1080                1085

Tyr Asn Val His Gln Pro Ser Glu Glu Arg Leu Glu Arg Met Gly Asp
    1090                1095                1100

Thr Gly Ile His Ala Asp Leu Gln Lys Gly Thr Val Glu Lys Trp Pro
1105                1110                1115                1120

Ala Leu Asn Leu Phe Ser Val Asp His Val Lys Asn Ile Glu Asn Leu
                1125                1130                1135

His Gly Ser Ser Leu Asn Asp Ser Ile Ala Gly Asp Asp Arg Asp Asn
                1140                1145                1150

Glu Leu Trp Gly Asp Asp Gly Asn Asp Thr Ile His Gly Arg Gly Gly
            1155                1160                1165

Asp Asp Ile Leu Arg Gly Gly Leu Gly Leu Asp Thr Leu Tyr Gly Glu
    1170                1175                1180

Asp Gly Asn Asp Ile Phe Leu Gln Asp Asp Glu Thr Val Ser Asp Asp
1185                1190                1195                1200

Ile Asp Gly Gly Ala Gly Leu Asp Thr Val Asp Tyr Ser Ala Met Ile
            1205                1210                1215

His Ala Gly Lys Ile Val Ala Pro His Glu Tyr Gly Phe Gly Ile Glu
            1220                1225                1230

Ala Asp Leu Ser Glu Gly Trp Val Arg Lys Ala Ala Arg Arg Gly Met
            1235                1240                1245

Asp Tyr Tyr Asp Ser Val Arg Ser Val Glu Asn Val Ile Gly Thr Ser
    1250                1255                1260

Met Lys Asp Val Leu Ile Gly Asp Ala Gln Ala Asn Thr Leu Met Gly
1265                1270                1275                1280

Gln Gly Gly Asp Asp Thr Val Arg Gly Gly Asp Gly Asp Asp Leu Leu
            1285                1290                1295

Phe Gly Gly Asp Gly Asn Asp Met Leu Tyr Gly Asp Ala Gly Asn Asp
                1300                1305                1310

Thr Leu Tyr Gly Gly Leu Gly Asp Asp Thr Leu Glu Gly Gly Ala Gly
            1315                1320                1325
```

Asn Asp Trp Phe Gly Gln Thr Pro Ala Arg Glu His Asp Val Leu Arg
    1330                1335                1340

Gly Gly Ala Gly Val Asp Thr Val Asp Tyr Ser Gln Ala Gly Ala His
1345                1350                1355                1360

Ala Gly Val Ala Thr Gly Arg Ile Gly Leu Gly Ile Leu Ala Asp Leu
            1365                1370                1375

Gly Ala Gly Arg Val Asp Lys Leu Gly Glu Ala Gly Ser Ser Ala Tyr
        1380                1385                1390

Asp Thr Val Ser Gly Ile Glu Asn Val Val Gly Thr Glu Leu Ala Asp
    1395                1400                1405

Arg Ile Thr Gly Asp Ala Gln Ala Asn Val Leu Arg Gly Ala Gly Gly
1410                1415                1420

Ala Asp Val Leu Ala Gly Gly Glu Gly Asp Asp Val Leu Leu Gly Gly
1425                1430                1435                1440

Asp Gly Asp Asp Gln Leu Ser Gly Asp Ala Gly Arg Asp Arg Leu Tyr
            1445                1450                1455

Gly Glu Ala Gly Asp Asp Trp Phe Phe Gln Asp Ala Ala Asn Ala Gly
        1460                1465                1470

Asn Leu Leu Asp Gly Gly Asp Gly Asn Asp Thr Val Asp Phe Ser Gly
    1475                1480                1485

Pro Gly Arg Gly Leu Asp Ala Gly Ala Lys Gly Val Phe Leu Ser Leu
1490                1495                1500

Gly Lys Gly Phe Ala Ser Leu Met Asp Glu Pro Glu Thr Ser Asn Val
1505                1510                1515                1520

Leu Arg His Ile Glu Asn Ala Val Gly Ser Val Arg Asp Asp Val Leu
            1525                1530                1535

Ile Gly Asp Ala Gly Ala Asn Val Leu Asn Gly Leu Ala Gly Asn Asp
        1540                1545                1550

Val Leu Ser Gly Gly Ala Gly Asp Asp Val Leu Leu Gly Asp Glu Gly
    1555                1560                1565

Ser Asp Leu Leu Ser Gly Asp Ala Gly Asn Asp Leu Phe Gly Gly
1570                1575                1580

Gln Gly Asp Asp Thr Tyr Leu Phe Gly Ala Gly Tyr Gly His Asp Thr
1585                1590                1595                1600

Ile Tyr Glu Ser Gly Gly Gly His Asp Thr Ile Arg Ile Asn Ala Gly
            1605                1610                1615

Ala Asp Gln Leu Trp Phe Ala Arg Gln Gly Asn Asp Leu Glu Ile Arg
        1620                1625                1630

Ile Leu Gly Thr Asp Asp Ala Leu Thr Val His Asp Trp Tyr Arg Asp
    1635                1640                1645

Ala Asp His Arg Val Glu Ala Ile His Ala Ala Asn Gln Ala Ile Asp
1650                1655                1660

Pro Ala Gly Ile Glu Lys Leu Val Glu Ala Met Ala Gln Tyr Pro Asp
1665                1670                1675                1680

Pro Gly Ala Ala Ala Ala Pro Pro Ala Ala Arg Val Pro Asp Thr
            1685                1690                1695

Leu Met Gln Ser Leu Ala Val Asn Trp Arg
        1700                1705

<210> SEQ ID NO 8
<211> LENGTH: 381
<212> TYPE: PRT
<213> ORGANISM: Mus musculus

<400> SEQUENCE: 8

```
Met Pro Phe Ser Asn Ser His Asn Thr Gln Lys Leu Arg Phe Pro Ala
 1               5                  10                  15

Glu Asp Glu Phe Pro Asp Leu Ser Ser His Asn Asn His Met Ala Lys
                20                  25                  30

Val Leu Thr Pro Glu Leu Tyr Ala Glu Leu Arg Ala Lys Cys Thr Pro
            35                  40                  45

Ser Gly Phe Thr Leu Asp Asp Ala Ile Gln Thr Gly Val Asp Asn Pro
 50                  55                  60

Gly His Pro Tyr Ile Met Thr Val Gly Ala Val Ala Gly Asp Glu Glu
 65                  70                  75                  80

Ser Tyr Asp Val Phe Lys Asp Leu Phe Asp Pro Ile Ile Glu Glu Arg
                85                  90                  95

His Gly Gly Tyr Gln Pro Ser Asp Glu His Lys Thr Asp Leu Asn Pro
                100                 105                 110

Asp Asn Leu Gln Gly Gly Asp Leu Asp Pro Asn Tyr Val Leu Ser
            115                 120                 125

Ser Arg Val Arg Thr Gly Arg Ser Ile Arg Gly Phe Cys Leu Pro Pro
            130                 135                 140

His Cys Ser Arg Gly Glu Arg Ala Ile Glu Lys Leu Ala Val Glu
145                 150                 155                 160

Ala Leu Ser Ser Leu Asp Gly Asp Leu Ser Gly Arg Tyr Tyr Ala Leu
                165                 170                 175

Lys Ser Met Thr Glu Ala Glu Gln Gln Gln Leu Ile Asp Asp His Phe
                180                 185                 190

Leu Phe Asp Lys Pro Val Ser Pro Leu Leu Leu Ala Ser Gly Met Ala
            195                 200                 205

Arg Asp Trp Pro Asp Ala Arg Gly Ile Trp His Asn Asp Asn Lys Thr
210                 215                 220

Phe Leu Val Trp Ile Asn Glu Glu Asp His Leu Arg Val Ile Ser Met
225                 230                 235                 240

Gln Lys Gly Gly Asn Met Lys Glu Val Phe Thr Arg Phe Cys Thr Gly
                245                 250                 255

Leu Thr Gln Ile Glu Thr Leu Phe Lys Ser Lys Asn Tyr Glu Phe Met
                260                 265                 270

Trp Asn Pro His Leu Gly Tyr Ile Leu Thr Cys Pro Ser Asn Leu Gly
                275                 280                 285

Thr Gly Leu Arg Ala Gly Val His Ile Lys Leu Pro His Leu Gly Lys
290                 295                 300

His Glu Lys Phe Ser Glu Val Leu Lys Arg Leu Arg Leu Gln Lys Arg
305                 310                 315                 320

Gly Thr Gly Gly Val Asp Thr Ala Ala Val Gly Gly Val Phe Asp Val
                325                 330                 335

Ser Asn Ala Asp Arg Leu Gly Phe Ser Glu Val Glu Leu Val Gln Met
                340                 345                 350

Val Val Asp Gly Val Lys Leu Leu Ile Glu Met Glu Gln Arg Leu Glu
            355                 360                 365

Gln Gly Gln Ala Ile Asp Asp Leu Met Pro Ala Gln Lys
370                 375                 380

<210> SEQ ID NO 9
<211> LENGTH: 381
<212> TYPE: PRT
<213> ORGANISM: Mus musculus
```

<400> SEQUENCE: 9

| | | | | | | | | | | | | | | |
|---|---|---|---|---|---|---|---|---|---|---|---|---|---|---|
| Met | Pro | Phe | Gly | Asn | Thr | His | Asn | Lys | Phe | Lys | Leu | Asn | Tyr | Lys | Pro |
| 1 | | | | 5 | | | | | 10 | | | | | 15 | |
| Gln | Glu | Glu | Tyr | Pro | Asp | Leu | Ser | Lys | His | Asn | Asn | His | Met | Ala | Lys |
| | | | | 20 | | | | | 25 | | | | | 30 | |
| Val | Leu | Thr | Pro | Asp | Leu | Tyr | Asn | Lys | Leu | Arg | Asp | Lys | Glu | Thr | Pro |
| | | | 35 | | | | | 40 | | | | | 45 | | |
| Ser | Gly | Phe | Thr | Leu | Asp | Asp | Val | Ile | Gln | Thr | Gly | Val | Asp | Asn | Pro |
| | 50 | | | | | 55 | | | | | 60 | | | | |
| Gly | His | Pro | Phe | Ile | Met | Thr | Val | Gly | Cys | Val | Ala | Gly | Asp | Glu | Glu |
| 65 | | | | | 70 | | | | | 75 | | | | | 80 |
| Ser | Tyr | Thr | Val | Phe | Lys | Asp | Leu | Phe | Asp | Pro | Ile | Ile | Gln | Asp | Arg |
| | | | | 85 | | | | | 90 | | | | | 95 | |
| His | Gly | Gly | Tyr | Lys | Pro | Thr | Asp | Lys | His | Lys | Thr | Asp | Leu | Asn | His |
| | | | | 100 | | | | | 105 | | | | | 110 | |
| Glu | Asn | Leu | Lys | Gly | Gly | Asp | Asp | Leu | Asp | Pro | Asn | Tyr | Val | Leu | Ser |
| | | | 115 | | | | | 120 | | | | | 125 | | |
| Ser | Arg | Val | Arg | Thr | Gly | Arg | Ser | Ile | Lys | Gly | Tyr | Thr | Leu | Pro | Pro |
| | 130 | | | | | 135 | | | | | 140 | | | | |
| His | Cys | Ser | Arg | Gly | Glu | Arg | Arg | Ala | Val | Glu | Lys | Leu | Ser | Val | Glu |
| 145 | | | | | 150 | | | | | 155 | | | | | 160 |
| Ala | Leu | Asn | Ser | Leu | Thr | Gly | Glu | Phe | Lys | Gly | Lys | Tyr | Tyr | Pro | Leu |
| | | | | 165 | | | | | 170 | | | | | 175 | |
| Lys | Ser | Met | Thr | Glu | Gln | Glu | Gln | Gln | Leu | Ile | Asp | Asp | His | Phe |
| | | | 180 | | | | | 185 | | | | | 190 | | |
| Leu | Phe | Asp | Lys | Pro | Val | Ser | Pro | Leu | Leu | Leu | Ala | Ser | Gly | Met | Ala |
| | | 195 | | | | | 200 | | | | | 205 | | | |
| Arg | Asp | Trp | Pro | Asp | Ala | Arg | Gly | Ile | Trp | His | Asn | Asp | Asn | Lys | Ser |
| | 210 | | | | | 215 | | | | | 220 | | | | |
| Phe | Leu | Val | Trp | Val | Asn | Glu | Glu | Asp | His | Leu | Arg | Val | Ile | Ser | Met |
| 225 | | | | | 230 | | | | | 235 | | | | | 240 |
| Glu | Lys | Gly | Gly | Asn | Met | Lys | Glu | Val | Phe | Arg | Arg | Phe | Cys | Val | Gly |
| | | | | 245 | | | | | 250 | | | | | 255 | |
| Leu | Gln | Lys | Ile | Glu | Glu | Ile | Phe | Lys | Lys | Ala | Gly | His | Pro | Phe | Met |
| | | | 260 | | | | | 265 | | | | | 270 | | |
| Trp | Asn | Glu | His | Leu | Gly | Tyr | Val | Leu | Thr | Cys | Pro | Ser | Asn | Leu | Gly |
| | 275 | | | | | 280 | | | | | 285 | | | | |
| Thr | Gly | Leu | Arg | Gly | Gly | Val | His | Val | Lys | Leu | Ala | Asn | Leu | Ser | Lys |
| | 290 | | | | | 295 | | | | | 300 | | | | |
| His | Pro | Lys | Phe | Glu | Glu | Ile | Leu | Thr | Arg | Leu | Arg | Leu | Gln | Lys | Arg |
| 305 | | | | | 310 | | | | | 315 | | | | | 320 |
| Gly | Thr | Gly | Gly | Val | Asp | Thr | Ala | Ala | Val | Gly | Ala | Val | Phe | Asp | Ile |
| | | | | 325 | | | | | 330 | | | | | 335 | |
| Ser | Asn | Ala | Asp | Arg | Leu | Gly | Ser | Ser | Glu | Val | Glu | Gln | Val | Gln | Leu |
| | | | 340 | | | | | 345 | | | | | 350 | | |
| Val | Val | Asp | Gly | Val | Lys | Leu | Met | Val | Glu | Met | Glu | Lys | Lys | Leu | Glu |
| | | 355 | | | | | 360 | | | | | 365 | | | |
| Lys | Gly | Gln | Ser | Ile | Asp | Asp | Met | Ile | Pro | Ala | Gln | Lys | | | |
| | 370 | | | | | 375 | | | | | 380 | | | | |

<210> SEQ ID NO 10
<211> LENGTH: 381
<212> TYPE: PRT
<213> ORGANISM: Homo sapiens

<400> SEQUENCE: 10

```
Met Pro Phe Ser Asn Ser His Asn Ala Leu Lys Leu Arg Phe Pro Ala
 1               5                  10                  15
Glu Asp Glu Phe Pro Asp Leu Ser Ala His Asn Asn His Met Ala Lys
            20                  25                  30
Val Leu Thr Pro Glu Leu Tyr Ala Glu Leu Arg Ala Lys Ser Thr Pro
        35                  40                  45
Ser Gly Phe Thr Leu Asp Asp Val Ile Gln Thr Gly Val Asp Asn Pro
    50                  55                  60
Gly His Pro Tyr Ile Met Thr Val Gly Cys Val Ala Gly Asp Glu Glu
65                  70                  75                  80
Ser Tyr Glu Val Phe Lys Asp Leu Phe Asp Pro Ile Ile Glu Asp Arg
                85                  90                  95
His Gly Gly Tyr Lys Pro Ser Asp Glu His Lys Thr Asp Leu Asn Pro
            100                 105                 110
Asp Asn Leu Gln Gly Gly Asp Asp Leu Asp Pro Asn Tyr Val Leu Ser
        115                 120                 125
Ser Arg Val Arg Thr Gly Arg Ser Ile Arg Gly Phe Cys Leu Pro Pro
    130                 135                 140
His Cys Ser Arg Gly Glu Arg Arg Ala Ile Glu Lys Leu Ala Val Glu
145                 150                 155                 160
Ala Leu Ser Ser Leu Asp Gly Asp Leu Ala Gly Arg Tyr Tyr Ala Leu
                165                 170                 175
Lys Ser Met Thr Glu Ala Glu Gln Gln Gln Leu Ile Asp Asp His Phe
            180                 185                 190
Leu Phe Asp Lys Pro Val Ser Pro Leu Leu Ser Ala Ser Gly Met Ala
        195                 200                 205
Arg Asp Trp Pro Asp Ala Arg Gly Ile Trp His Asn Asp Asn Lys Thr
    210                 215                 220
Phe Leu Val Trp Val Asn Glu Glu Asp His Leu Arg Val Ile Ser Met
225                 230                 235                 240
Gln Lys Gly Gly Asn Met Lys Glu Val Phe Thr Arg Phe Cys Thr Gly
                245                 250                 255
Leu Thr Gln Ile Glu Thr Leu Phe Lys Ser Lys Asp Tyr Glu Phe Met
            260                 265                 270
Trp Asn Pro His Leu Gly Tyr Ile Leu Thr Cys Pro Ser Asn Leu Gly
        275                 280                 285
Thr Gly Leu Arg Ala Gly Val His Ile Lys Leu Pro Asn Leu Gly Lys
    290                 295                 300
His Glu Lys Phe Ser Glu Val Leu Lys Arg Leu Arg Leu Gln Lys Arg
305                 310                 315                 320
Gly Thr Gly Gly Val Asp Thr Ala Ala Val Gly Val Phe Asp Val
                325                 330                 335
Ser Asn Ala Asp Arg Leu Gly Phe Ser Glu Val Glu Leu Val Gln Met
            340                 345                 350
Val Val Asp Gly Val Lys Leu Leu Ile Glu Met Glu Gln Arg Leu Glu
        355                 360                 365
Gln Gly Gln Ala Ile Asp Asp Leu Met Pro Ala Gln Lys
    370                 375                 380
```

<210> SEQ ID NO 11
<211> LENGTH: 446
<212> TYPE: PRT

<213> ORGANISM: Thermoproteus tenax

<400> SEQUENCE: 11

```
Met Phe Thr Lys Ile Val Ala Thr Leu Gly Pro Ser Thr Asp Arg Leu
  1               5                  10                  15

Pro Asp Ile Thr Ala Leu Leu Ser Lys Val His Gly Val Arg Ile Asn
             20                  25                  30

Met Ser His Ala Ser Pro Ser Glu Val Glu Ala Arg Val Asn Ala Val
         35                  40                  45

Arg Lys Tyr Glu Glu Thr Ser Gly Arg Tyr Ile Ala Ile Ile Ala Asp
     50                  55                  60

Leu Arg Gly Pro Ser Val Arg Thr Gly Leu Met Arg Pro Leu Gln Ile
 65                  70                  75                  80

Thr Ala Gly Ala Arg Val Ser Phe Lys Leu Ala Glu Lys Gly Asp Gly
                 85                  90                  95

Phe Val Pro Val Pro Arg Arg Glu Phe Phe Glu Val Ile Glu Glu Gly
                100                 105                 110

Asp Glu Val Leu Met Leu Asp Gly Lys Leu Val Leu Arg Ile Ile Ser
            115                 120                 125

Ala Ala Gln Thr Ser Ala Glu Ala Glu Ser Leu Ser Ser Gly Val Ile
        130                 135                 140

Ser Ser Asn Lys Ala Ile Val Val Lys Gly Lys Glu Tyr His Ile Glu
145                 150                 155                 160

Gln Pro Val Glu Glu Asp Ile Arg Ala Leu Gln Thr Leu Ser Arg Phe
                165                 170                 175

Arg Asp Asp Val Asp Tyr Val Ala Leu Ser Leu Val Arg Asp Gly Ala
            180                 185                 190

Asp Val Arg Lys Met Arg Ser Val Val Glu Glu Ala Gly Leu Thr Ser
        195                 200                 205

Gly Ile Met Ala Lys Ile Glu Thr Lys Ser Ala Val Asp Lys Ile Glu
    210                 215                 220

Glu Ile Ile Asn Ala Ala Asp Tyr Ile Val Ile Ala Arg Gly Asp Leu
225                 230                 235                 240

Ala Leu His Tyr Gly Leu Glu Tyr Ile Pro Lys Val Gln Arg Leu Leu
                245                 250                 255

Val Glu Arg Ser Leu Ser Ala Gly Arg Pro Val Ala Val Ala Thr Gln
            260                 265                 270

Leu Leu Asp Ser Met Gln Thr Asn Thr Thr Pro Thr Arg Ala Glu Val
        275                 280                 285

Asn Asp Val Tyr Thr Thr Ala Ser Leu Gly Val Asp Ser Leu Trp Leu
    290                 295                 300

Thr Asn Glu Thr Ala Ser Gly Glu His Pro Leu Glu Ala Val Asp Trp
305                 310                 315                 320

Leu Arg Arg Ile Val Ser Gln Val Glu Phe Gly Arg Leu Lys Ala Ala
                325                 330                 335

Ser Pro Ala Asp Ala Arg Asp Arg Phe Ala Lys Ala Val Val Asp Met
            340                 345                 350

Ala Glu Asp Met Gly Gly Glu Ile Ala Val Tyr Ser Met Thr Gly Thr
        355                 360                 365

Leu Ala Lys Arg Ile Ala Lys Phe Arg Pro Met Thr Thr Val Tyr Val
    370                 375                 380

Gly Val Asn Glu Arg Arg Leu Ala Arg Met Leu Glu Leu Arg Glu Asp
385                 390                 395                 400
```

-continued

Val Gly Ala His Met Gly Pro Arg Ala Cys Gly Arg Ala Gly Ala Tyr
                405                 410                 415

Leu Arg Gly Gly Pro Arg Glu Ala Pro Leu Gln Ile Leu Arg Gln Ser
            420                 425                 430

Leu Asp Ser His Val Trp Ala Gln Arg Arg His Thr Tyr Tyr
            435                 440                 445

<210> SEQ ID NO 12
<211> LENGTH: 531
<212> TYPE: PRT
<213> ORGANISM: Artificial Sequence
<220> FEATURE:
<223> OTHER INFORMATION: A synthetic ADP to ATP converting enzyme.

<400> SEQUENCE: 12

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

```
Gly Lys Pro Val Ile Cys Ala Thr Gln Met Leu Glu Ser Met Ile Lys
            325                 330                 335

Lys Pro Pro Thr Arg Ala Glu Gly Ser Asp Val Ala Asn Ala Val
        340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
    370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
            405                 410                 415

Val Glu Ala Ser Phe Lys Cys Cys Ser Gly Ala Ile Ile Val Leu Thr
                420                 425                 430

Lys Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
        450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
            485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
            515                 520                 525

Pro Val Pro
    530

<210> SEQ ID NO 13
<211> LENGTH: 194
<212> TYPE: PRT
<213> ORGANISM: Artificial Sequence
<220> FEATURE:
<223> OTHER INFORMATION: A synthetic ADP to ATP converting enzyme.

<400> SEQUENCE: 13

Met Glu Glu Lys Leu Lys Lys Thr Lys Ile Ile Phe Val Val Gly Gly
1               5                   10                  15

Pro Gly Ser Gly Lys Gly Thr Gln Cys Glu Lys Ile Val Gln Lys Tyr
            20                  25                  30

Gly Tyr Thr His Leu Ser Thr Gly Asp Leu Leu Arg Ser Glu Val Ser
        35                  40                  45

Ser Gly Ser Ala Arg Gly Lys Lys Leu Ser Glu Ile Met Glu Lys Gly
    50                  55                  60

Gln Leu Val Pro Leu Glu Thr Val Leu Asp Met Leu Arg Asp Ala Met
65                  70                  75                  80

Val Ala Lys Val Asn Thr Ser Lys Gly Phe Leu Ile Asp Gly Tyr Pro
                85                  90                  95

Arg Glu Val Gln Gln Gly Glu Glu Phe Glu Arg Arg Ile Gly Gln Pro
            100                 105                 110

Thr Leu Leu Leu Tyr Val Asp Ala Gly Pro Glu Thr Met Thr Gln Arg
        115                 120                 125

Leu Leu Lys Arg Gly Glu Thr Ser Gly Arg Val Asp Asp Asn Glu Glu
    130                 135                 140
```

Thr Ile Lys Lys Arg Leu Glu Thr Tyr Tyr Lys Ala Thr Glu Pro Val
145                 150                 155                 160

Ile Ala Phe Tyr Glu Lys Arg Gly Ile Val Arg Lys Val Asn Ala Glu
            165                 170                 175

Gly Ser Val Asp Ser Val Phe Ser Gln Val Cys Thr His Leu Asp Ala
            180                 185                 190

Leu Lys

<210> SEQ ID NO 14
<211> LENGTH: 6382
<212> TYPE: DNA
<213> ORGANISM: Bordetella pertussis

<400> SEQUENCE: 14

| | | | | | |
|---|---|---|---|---|---|
| tgcgatcatt | cggcatgtac | ggtccagctg | cgcgcgagcg | gcggccgcgt | ccagcgcgcg | 60 |
| gcctcggtac | tccttgacgc | gcgcggtgtc | gccgccgcgc | cgaacgcgca | gcgaacggcc | 120 |
| cacgctgtcg | gggtgccgtt | cggccagcgc | gcggcgcagc | gcacgattgt | cgtcgcgcga | 180 |
| gaatggcgcg | atccagtcga | tgatccacag | tcggtcgccg | cagttccagg | cattcccgcc | 240 |
| cagcgacgag | ggcgccatga | cataggagag | ttcggtgtcg | gcgtccatta | gggcccagct | 300 |
| gcagtatgca | accggcacgt | cattgcatcg | cagcagaatg | tattggccca | gttgaatcgg | 360 |
| cgcgagcgct | gttgcgtgcg | agcagatgca | ccggccagtc | gcggtgcatg | ggagagttca | 420 |
| tccacagcca | ggcaatattg | cccagtgccg | cgaagtcgtc | ggtgggattg | aggagggagg | 480 |
| gcgcttgggc | ggacggaagc | atgacatcgg | tgcatggtgg | agcgggggc | atattccgtg | 540 |
| ttgggtgcgc | gcatggcaag | ccgccggcgc | atcatggttg | cgccggaatg | gcttttctta | 600 |
| catgtttcca | ggatatgtcc | gtatttcggg | cgatgcctcg | gtcgcggcgc | ctgcttttgt | 660 |
| cgaacatgtg | caatgttgtt | gtcgcgatcg | cgttggcgct | tgctcgctta | tttatctccc | 720 |
| ttgaagcctt | gttcttcttt | tcattagaaa | gaaatatgcg | ctttgtgttt | aggatgattt | 780 |
| tcctgtccga | gtagggtgga | tccaaatttt | ccggattggt | gggaatttgt | gcattttcac | 840 |
| tgcgaatgtt | ggaataattt | cgcccatcgt | catacgacat | gctggatgtt | tggttcttgc | 900 |
| agaaggatga | ggttctgagc | gctacacacc | ggttgcgtcg | gtgcgaatcc | gttcaatcga | 960 |
| ctacttatcg | acagatccac | atgcagcaat | cgcatcaggc | tggttacgca | aacgccgccg | 1020 |
| accgggagtc | tggcatcccc | gcagccgtac | tcgatggcat | caaggccgtg | gcgaaggaaa | 1080 |
| aaaacgccac | attgatgttc | cgcctggtca | accccattc | caccagcctg | attgccgaag | 1140 |
| gggtggccac | caaaggattg | ggcgtgcacg | ccaagtcgtc | cgattggggg | ttgcaggcgg | 1200 |
| gctacattcc | cgtcaacccg | aatctttcca | aactgttcgg | ccgtgcgccc | gaggtgatcg | 1260 |
| cgcgggccga | caacgacgtc | aacagcagcc | tggcgcatgg | ccataccgcg | gtcgacctga | 1320 |
| cgctgtcgaa | agagcggctt | gactatctgc | ggcaagcggg | cctggtcacc | ggcatggccg | 1380 |
| atggcgtggt | cgcgagcaac | cacgcaggct | acgagcagtt | cgagtttcgc | gtgaaggaaa | 1440 |
| cctcggacgg | gcgctatgcc | gtgcagtatc | gccgcaaggg | cggcgacgat | ttcgaggcgg | 1500 |
| tcaaggtgat | cggcaatgcc | gccggtattc | cactgacggc | ggatatcgac | atgttcgcca | 1560 |
| ttatgccgca | tctgtccaac | ttcgcgcgact | cggcgcgcag | ttcggtgacc | agcggcgatt | 1620 |
| cggtgaccga | ttacctggcg | cgcacgcggc | gggccgccag | cgaggccacg | gcggcctgg | 1680 |
| atcgcgaacg | catcgacttg | ttgtggaaaa | tcgctcgcgc | cggcgcccgt | tccgcagtgg | 1740 |
| gcaccgaggc | gcgtcgccag | ttccgctacg | acggcgacat | gaatatcggc | gtgatcaccg | 1800 |

```
atttcgagct ggaagtgcgc aatgcgctga acaggcgggc gcacgccgtc ggcgcgcagg    1860
acgtggtcca gcatggcact gagcagaaca atcctttccc ggaggcagat gagaagattt    1920
tcgtcgtatc ggccaccggt gaaagccaga tgctcacgcg cgggcaactg aaggaataca    1980
ttggccagca gcgcggcgag ggctatgtct tctacgagaa ccgtgcatac ggcgtggcgg    2040
ggaaaagcct gttcgacgat gggctgggag ccgcgcccgg cgtgccgagc ggacgttcga    2100
agttctcgcc ggatgtactg gaaacggtgc cggcgtcacc cggattgcgg cggccgtcgc    2160
tgggcgcagt ggaacgccag gattccggct atgacagcct tgatggggtg ggatcgcgat    2220
cgttctcgtt gggcgaggtg tccgacatgg ccgccgtgga agcggcggaa ctggaaatga    2280
cccggcaagt cttgcacgcc ggggcgcggc aggacgatgc cgagccgggc gtgagcggtg    2340
cgtcggcgca ctgggggcag cgggcgctgc agggcgccca ggcggtggcg gcggcgcagc    2400
ggctggttca tgccattgcc ctgatgacgc aattcggccg ggccggttcc accaacacgc    2460
cgcaggaagc ggcctcgttg tcggcggccg tgttcggctt gggcgaggcc agcagcgccg    2520
tggccgaaac cgtgagcggt tttttccgcg ggtcttcgcg ctgggccggc ggtttcggcg    2580
tggctggcgg cgccgatggcg ctgggaggcg gcatcgccgc ggccgttggc gccgggatgt    2640
cgttgaccga tgacgcgccg ccggacagaa aggccgccgc cggcgccgag atcgcgctgc    2700
agttgacagg tggaacggtc gagctggctt cttccatcgc gttggcgctg ccgcggcgc    2760 gcggcgtgac cagcggcttg caggtggccg gggcgtcggc cggggcggct gccggcgcat    2820
tggccgcggc gctcagtccc atggagatct acggcctggt gcagcaatcg cactatgcgg    2880
tggcccagct gtatcgcgac aagacggccg ccgaggcgc cgtcgccggc gtctccgccg    2940
tcctgagcac ggtgggggcg gcggtgtcga tcgccgcggc ggccagcgtg gtaggggccc    3000
cggtggcggt ggtcacttcc ttgctgaccg gggctctcaa cggcatcctg cgcggcgtgc    3060
agcagcccat catcgaaaag ctggccaacg attacgctcg caagatcgac gagctgggcg    3120
ggccgcaagc gtacttcgag aaaaacctgc aggcgcgtca cgaacaactg gccaattcgg    3180
acggcctacg gaaaatgctg gccgacctgc aggccggttg gaacgccagc agcgtgatcg    3240
gggtgcagac gacagagatc tccaagtcgg cgctcgaact ggccgccatt accggcaacg    3300
cggacaacct gaaatccgtc gacgtgttcg tggaccgctt cgtccagggc gagcgggtgg    3360
ccggccagcc ggtggtcctc gacgtcgccg ccggcggcat cgatatcgcc agccgcaagg    3420
gcgagcggcc ggcgctgacg ttcatcacgc cgctggccgc gccaggagaa gagcagcgcc    3480
ggcgcacgaa aacgggcaag agcgaattca ccacattcgt cgagatcgtg ggcaagcagg    3540
accgctggcg catccgggac ggcgcggccg acaccaccat cgatctggcc aaggtggtgt    3600
cgcaactggt cgacgccaat ggcgtgctca agcacagcat caaactggat gtgatcggcg    3660
gagatggcga tgacgtcgtg cttgccaatg cttcgcgcat ccattatgac ggcggcgcgg    3720
gcaccaacac ggtcagctat gccgcccgtg gtcgacagga ttccattacc gtgtccgccg    3780
acggggaacg tttcaacgtg cgcaagcagt tgaacaacgc caacgtgtat cgcgaaggcg    3840
tggctaccca gacaaccgcc tacggcaagc gcacggagaa tgtccaatac cgccatgtcg    3900
agctggcccg tgtcgggcaa gtggtggagg tcgacacgct cgagcatgtg cagcacatca    3960
tcggcggggc cggcaacgat tcgatcaccg gcaatgcgca cgacaacttc ctagccggcg    4020
ggtcgggcga cgacaggctg gatgcggcgc ccggcaacga caccctggtt ggcggcgagg    4080
gccaaaacac ggtcatcggc ggccgccgcg acgacgtatt cctgcaggac ctgggggtat    4140
ggagcaacca gctcgatggc ggcgcggcgt cgataccgt gaagtacaac gtgcaccagc    4200
```

```
cttccgagga gcgcctcgaa cgcatgggcg acacgggcat ccatgccgat cttcaaaagg    4260
gcacggtcga gaagtggccg gccctgaacc tgttcagcgt cgaccatgtc aagaatatcg    4320
agaatctgca cggctcccgc ctaaacgacc gcatcgccgg cgacgaccag gacaacgagc    4380
tctggggcca cgatggcaac gacacggtac gcggccgggg cggcgacgac atcctgcgcg    4440
gcggcctggg cctggacacg ctgtatggcg aggacggcaa cgacatcttc ctgcaggacg    4500
acgagaccgt cagcgatgac atcgacgcg gcgcggggct ggacaccgtc gactactccg    4560
ccatgatcca tccaggcagg atcgttgcgc cgcatgaata cggcttcggg atcgaggcgg    4620
acctgtccag ggaatgggtg cgcaaggcgt ccgcgctggg cgtggactat tacgataatg    4680
tccgcaatgt cgaaaacgtc atcggtacga gcatgaagga tgtgctcatc ggcgacgcgc    4740
aagccaatac cctgatgggc cagggcgcg acgataccgt gcgcggcggc gacggcgatg    4800
atctgctgtt cggcggcgac ggcaacgaca tgctgtatgg cgacgccggc aacgacaccc    4860
tctacggggg gctgggcgac gatacccttg aaggcgcgc gggcaacgat tggttcggcc    4920
agacgcaggc gcgcgagcat gacgtgctgc gcggcggaga tggggtggat accgtcgatt    4980
acagccagac cggcgcgcat gccggcattg ccgcgggtcg catcgggctg gcatcctgg    5040 ctgacctggg cgccggccgc gtcgacaagc tgggcgaggc cggcagcagc gcctacgata    5100
cggtttccgg tatcgagaac gtggtgggca cggaactggc cgaccgcatc acgggcgatg    5160
cgcaggccaa cgtgctgcgc ggcgcgggtg gcgccgacgt gcttgcgggc ggcgagggcg    5220
acgatgtgct gctgggcggc gacggcgacg accagctgtc gggcgacgcc ggacgcgatc    5280
gcttgtacgg cgaagccggt gacgactggt tcttccagga tgccgccaat gccggcaatc    5340
tgctcgacgg cggcgacggc cgcgataccg tggatttcag cggcccgggc cggggcctcg    5400
acgccggcgc aaagggcgta ttcctgagct tgggcaaggg gttcgccagc ctgatggacg    5460
aacccgaaac cagcaacgtg ttgcgcaata tcgagaacgc cgtgggcagc gcgcgtgatg    5520
acgtgctgat cggcgacgca ggcgccaacg tcctcaatgg cctggcgggc aacgacgtgc    5580
tgtccggcgg cgctggcgac gatgtgctgc tgggcgacga gggctcggac ctgctcagcg    5640
gcgatgcggg caacgacgat ctgttcggcg ggcagggcga tgatacttat ctgttcgggg    5700
tcgggtacgg gcacgacacg atctacgaat cgggcggcgg ccatgacacc atccgcatca    5760
acgcgggggc ggaccagctg tggttcgcgc gccaggcaa cgacctggag atccgcattc    5820
tcggcaccga cgatgcactt accgtgcacg actggtatcg cgacgccgat caccgggtgg    5880
aaatcatcca tgccgccaac caggcggtag accaggcagg catcgaaaag ctggtcgagg    5940
caatggcgca gtatccggac cccggcgcgg cggcggctgc cccgccggcg gcgcgcgtgc    6000
cggacacgct gatgcagtcc ctggctgtca actggcgctg aagcgccgtg aatcacggcc    6060
cgcctgcctc gcgcggcggc gccgtctctt tgcgttcttc tccgaggtat ttcccatcat    6120
gacgtcgccc gcggcgcaat gcgccagcgt gcccgattcc gggttgctct gcctggtcat    6180
gctggctcgc tatcacggat tggcagccga tcccgagcag ttgcggcatg agttcgccga    6240
gaggcattct gtagcgaaac gatacagcct ggcggcgcgc gggtcggcc tgaaagtgcg    6300 gcggcaccga cccgcgccgg cgcggctgcc acgcgcgccg ctgccggcca tcgcgctgga    6360
ccggtagggc ggctactttg tt    6382
```

<210> SEQ ID NO 15
<211> LENGTH: 3420
<212> TYPE: DNA

<213> ORGANISM: Bacillus anthracis

<400> SEQUENCE: 15

```
ttactttttt atatactgaa ttaaaaagtc caagcactta tatcgtaata gatgctttct      60
attgacctta tagtccttga agttacgact gaccaattat gagacgtttg cgctaacctg     120
ctgaattcaa aatcggactt agaaatacac atatagaaat aaacaaccta atccatgtca     180
ctgtaccgtt tttttactaa ataaacgaaa tcagtgtaaa aatgaacagc tgaactttat     240
caacttagaa tctctttttt tactttaaat gcctagctgt tttttctaat gtttgtattt     300
ctaaatatat ttaaatatga attgtagctg tgtgccaaga gttataatta atttaaataa     360
gattatattt gtaaataaaa ttgtaattta acatgtagaa taaagagatt tttagtttta     420
ttaacaggat gaaaatccat aaaaccgtaa atgtgatttc taaattagtt taaaataaaa     480
aacaaggatt tgctcagact tgagatgaat atctaaatat caagaaccaa aggaggttta     540
agaatgacta gaaataaatt tatacctaat aagtttagta ttatatcctt ttcagtatta     600
ctatttgcta tatcctcctc acaggctata gaagtaaatg ctatgaatga acattacact     660
gagagtgata ttaaaagaaa ccataaaact gaaaaaaata aaactgaaaa agaaaaattt     720
aaagacagta ttaataactt agttaaaaca gaatttacca atgaaacttt agataaaata     780
cagcagacac aagacttatt aaaaagata cctaaggatg tacttgaaat ttatagtgaa     840
ttaggaggag aaatctattt tacagatata gatttagtag aacataagga gttacaagat     900
ttaagtgaag aagagaaaaa tagtatgaat agtagaggtg aaaaagttcc gtttgcatcc     960
cgttttgtat ttgaaaagaa aagggaaaca cctaaattaa ttataaatat caagagattat   1020
gcaattaata gtgaacaaag taagaagta tattatgaaa ttggaaaggg gatttctctt    1080
gatattataa gtaaggataa atctctagat ccagagtttt taaatttaat taagagttta   1140
agcgatgata gtgatagtag cgaccttta tttagtcaaa aatttaaaga gaagctagaa   1200
ttgaataata aaagtataga tataaatttt ataaagaaa atttaactga atttcagcat   1260
gcgttttctt tagcgttttc ttattatttt gcacctgacc atagaacggt attagagtta   1320
tatgcccccg acatgtttga gtatatgaat aagttagaaa aaggggatt tgagaaaata   1380
agtgaaagtt tgaagaaaga aggtgtggaa aaagatagga ttgatgtgct gaaaggagaa   1440
aaagcactta aagcttcagg tttagtacca gaacatgcag atgcttttaa aaaaattgct   1500
agagaattaa atacatatat tcttttttagg cctgttaata agttagctac aaaccttatt   1560
aaaagtggtg tggctacaaa gggattgaat gaacatggaa agagttcgga ttggggccct   1620
gtagctggat acataccatt tgatcaagat ttatctaaga agcatggtca acaattagct   1680
gtcgagaaag gaaatttaga aaataaaaaa tcaattacag agcatgaagg tgaaataggt   1740
aaaataccat taagttaga ccatttaaga atagaagagt taaggaaaa tgggataatt   1800
ttgaagggta aaaagaaat tgataatggt aaaaaatatt attttgttaga atcgaataat   1860
caggtatatg aatttagaat tagcgatgaa aacaacgaag tacaatacaa gacaaaagaa   1920
ggtaaaatta ctgtttttаgg ggaaaaattc aattggagaa atatagaagt gatggctaaa   1980
aatgtagaag gggtcttgaa gccgttaaca gctgactatg atttatttgc acttgcccca   2040
agtttaacag aaataaaaaa acaaataccc acaaaaagaa tggataaagt agttaacacc   2100
ccaaattcat tagaaaagca aaaggtgtt actaatttat tgattaaata tggaattgag   2160
aggaaaccgg attcaactaa gggaaccttta tcaaattggc aaaaacaaat gcttgatcgt   2220
ttgaatgaag cagtcaaata tacaggatat acagggggg atgtggttaa ccatggcaca   2280
```

-continued

```
gagcaagata atgaagagtt tcctgaaaaa gataacgaaa ttttttataat taatccagaa   2340 ggtgaattta tattaactaa aaattgggag atgacaggta gatttataga aaaaaacatt   2400
acgggaaaag attatttata ttattttaac cgttcttata ataaaatagc tcctggtaat   2460
aaagcttata ttgagtggac tgatccgatt acaaaagcca aaatataatac catccctacg   2520 tcagcagagt ttataaaaaa cttatccagt atcagaagat cttcaaatgt aggagtttat   2580
aaagatagtg gcgacaaaga cgaatttgca aaaaaagaaa gcgtgaaaaa aattgcagga   2640
tatttgtcag actattacaa ttcagcaaat catatttttt ctcaggaaaa aaagcgtaaa   2700
atatcaatat ttcgtggaat ccaagcctat aatgaaattg aaaatgttct aaaatctaaa   2760
caaatagcac cagaatacaa aaattatttt caatatttaa aggaaaggat taccaatcaa   2820
gttcaattgc ttctaacaca tcaaaaatct aatattgaat ttaaattatt gtataaacaa   2880
ttaaacttta cagaaaatga aacggataat tttgaggtct tccaaaaaat tattgatgaa   2940 aaataaaatat atataattgt ttttctgaaa attcatcatt ttaaagaaga cactaggaat   3000
taaatagatg tattgaatag ttatagtaat ggtcttgtat ggacataccg cttatacttt   3060
gggaggtagt agatattaaa caacatatag caaatgaact ggagtgtaga tcaaaagaaa   3120
tttttctaaa aaatatctca tctttaataa aaaatggcac tgtatataaa gcagcaacag   3180
ataaaattat tacctatatg caaaagattt aaatattgac cttgtaatag gcatggaatc   3240
tcgagggttt attttttggtt gcccagtttc atatgctttg ggaataggtt ttataccggt   3300
tcgtaaatta gggaccctgg ttggatttga taatgagaac gtaaaagata ttctaacaat   3360
aaataatgat gcgattaacc aggccacgtg tgttaatact gatgtatgtg taactactgg   3420
```